US009951164B2

(12) United States Patent
Ishimaru et al.

(10) Patent No.: US 9,951,164 B2
(45) Date of Patent: Apr. 24, 2018

(54) NON-IONIC ARYL KETONE BASED POLYMERIC PHOTO-ACID GENERATORS

(71) Applicants: International Business Machines Corporation, Armonk, NY (US); Central Glass Co., Ltd., Yamaguchi (JP)

(72) Inventors: Takehisa Ishimaru, Tokyo (JP); Satoru Narizuka, Kawagoe (JP); Daniel P. Sanders, San Jose, CA (US); Ratnam Sooriyakumaran, San Jose, CA (US); Hoa D. Truong, San Jose, CA (US); Rudy J. Wojtecki, San Jose, CA (US)

(73) Assignees: International Business Machines Corporation, Armonk, NY (US); Central Glass Co., Ltd., Ube-shi, Yamaguchi (JP)

( * ) Notice: Subject to any disclaimer, the term of this patent is extended or adjusted under 35 U.S.C. 154(b) by 0 days.

(21) Appl. No.: 15/235,673

(22) Filed: Aug. 12, 2016

(65) Prior Publication Data

US 2018/0044459 A1    Feb. 15, 2018

(51) Int. Cl.
| | |
|---|---|
| *G03F 7/004* | (2006.01) |
| *G03F 7/38* | (2006.01) |
| *C07C 317/04* | (2006.01) |
| *C07C 317/06* | (2006.01) |
| *C07C 317/08* | (2006.01) |
| *C07C 317/10* | (2006.01) |
| *C07C 317/14* | (2006.01) |
| *C07C 317/24* | (2006.01) |
| *C07C 317/26* | (2006.01) |
| *C07C 317/32* | (2006.01) |
| *C08F 212/04* | (2006.01) |
| *C08F 212/32* | (2006.01) |
| *C08F 220/24* | (2006.01) |
| *C08F 220/38* | (2006.01) |
| *C07C 309/69* | (2006.01) |
| *C07C 309/70* | (2006.01) |
| *C08F 220/68* | (2006.01) |
| *G03F 7/039* | (2006.01) |
| *G03F 7/038* | (2006.01) |
| *G03F 7/20* | (2006.01) |
| *G03F 7/32* | (2006.01) |
| *C07C 309/68* | (2006.01) |
| *C07C 309/77* | (2006.01) |

(52) U.S. Cl.
CPC .......... *C08F 220/68* (2013.01); *C07C 309/68* (2013.01); *C07C 309/69* (2013.01); *C07C 309/70* (2013.01); *C07C 309/77* (2013.01); *G03F 7/0046* (2013.01); *G03F 7/038* (2013.01); *G03F 7/039* (2013.01); *G03F 7/2004* (2013.01); *G03F 7/322* (2013.01); *G03F 7/325* (2013.01); *G03F 7/38* (2013.01)

(58) Field of Classification Search
CPC .... G03F 7/0045; G03F 7/0397; G03F 7/0046; C07C 317/04; C07C 317/06; C07C 317/08; C07C 317/10; C07C 317/14; C07C 317/24; C07C 317/26; C07C 317/32; C07C 309/69; C07C 309/70; C08F 212/04; C08F 212/32; C08F 220/24; C08F 220/38
USPC ....... 430/270.1, 919, 921, 325, 326; 568/28, 568/30, 31, 32, 33, 34, 35; 526/243, 245, 526/281, 282, 287, 288
See application file for complete search history.

(56) References Cited

U.S. PATENT DOCUMENTS

| | | | |
|---|---|---|---|
| 4,889,791 A | 12/1989 | Tsuchiya et al. | |
| 5,135,838 A | 8/1992 | Houlihan et al. | |
| 5,624,777 A | 4/1997 | Kato et al. | |
| 6,855,476 B2 * | 2/2005 | Ferreira ................ | C07C 309/10 430/270.1 |
| 7,402,626 B2 | 7/2008 | Maeda et al. | |
| 7,759,047 B2 | 7/2010 | Hatakeyama et al. | |
| 8,057,985 B2 | 11/2011 | Ohashi et al. | |
| 8,158,330 B2 | 4/2012 | Harada et al. | |
| 8,163,461 B2 | 4/2012 | Ober et al. | |
| 9,223,208 B2 * | 12/2015 | Tsuchimura .......... | C07C 317/44 |
| 9,223,209 B2 | 12/2015 | Sanders et al. | |
| 9,244,345 B1 | 1/2016 | Ishimaru et al. | |
| 9,249,248 B1 | 2/2016 | Brust et al. | |

(Continued)

FOREIGN PATENT DOCUMENTS

JP        H10221852 A     8/1998

OTHER PUBLICATIONS

Fielding et al., "Synthesis and reactions of 4-sulpho-2,3,5,6,-tetrafluorobenzoic acid", Journal of Fluorine Chemistry, 59, (1992), 15-31.

(Continued)

*Primary Examiner* — John S Chu
(74) *Attorney, Agent, or Firm* — Michael R. Roberts

(57) ABSTRACT

Non-ionic photo-acid generating (PAG) polymerizable monomers were prepared that contain a side chain sulfonate ester of an alpha-hydroxy aryl ketone. The aryl ketone group has a perfluorinated substituent alpha to the ketone carbonyl. The sulfur of the sulfonate ester is also directly linked to a fluorinated group. PAG polymers prepared from the PAG monomers release a strong sulfonic acid when exposed to high energy radiation such as deep UV or extreme UV light. The photo-generated sulfonic acid has a low diffusion rate in an exposed resist layer subjected to a post-exposure bake (PEB) at 100° C. to 150° C., resulting in formation of good line patterns after development.

25 Claims, 5 Drawing Sheets

(56) References Cited

U.S. PATENT DOCUMENTS

| 9,274,420 B2* | 3/2016 | Akiba | G03F 7/0045 |
| 2014/0065541 A1* | 3/2014 | Akiba | G03F 7/0045 430/283.1 |
| 2014/0093823 A1* | 4/2014 | Brainard | G03F 7/0045 430/283.1 |
| 2014/0193752 A1* | 7/2014 | Brainard | C07C 309/65 430/283.1 |

OTHER PUBLICATIONS

Hinsberg, et al., "Effect of Resist Components on Image Spreading During Postexposure Bake of Chemically Amplified Resists", Proceedings of SPIE vol. 3999 (2000), pp. 148-160.

* cited by examiner

NON-IONIC ARYL KETONE BASED POLYMERIC PHOTO-ACID GENERATORS

BACKGROUND

The present invention relates to non-ionic aryl ketone based polymeric photo-acid generators (PAGs), and more specifically to fluorinated PAG polymers comprising aryl ketone protected sulfonate ester groups that undergo photochemically induced deprotection, generating a fluorinated polysulfonic acid for lithographic applications.

Extreme ultraviolet (EUV) lithography, combined with multiple patterning enhancements, is expected to succeed current 193 nm immersion lithography as the next generation printing technique. EUV radiation, with a shorter wavelength of 13.5 nm, is expected to achieve sub-20 nm features in a single exposure process. However, more advances in efficient light sources, EUV masks, and resists are needed for EUV lithography to become a manufacturing process.

During the last few years, considerable effort has gone into the development of resists for EUV applications. However, the majority of the EUV resists have been modified from the resists developed for 193 nm and 248 nm applications.

The highest performing photoresists for 193 nm and 248 nm applications are all based on a chemical amplification mechanism. Chemically amplified photoresists utilize a catalytic mechanism to generate a relatively large number of chemical events (e.g., deprotection reactions in the case of positive tone photoresists, or crosslinking reactions in the case of negative tone photoresists). Application of a relatively low dose of radiation induces formation of the catalyst, often a strong acid, which then catalyzes the chemical events. The current positive resist compositions comprise aqueous base soluble functional groups that are sufficiently protected with acid-labile groups so that the resist initially will not dissolve in an aqueous base developer. During exposure to radiation, the photo-acid generator (PAG) present in the resist composition produces a strong acid, which then catalyzes the removal of the acid-labile groups upon heating the exposed resist layer in a post-exposure bake (PEB). This process produces aqueous base soluble material in the exposed area, which then is selectively removed with a basic aqueous developer to produce the images.

One phenomenon that limits the resolution potential of the resists developed for 248 nm, 193 nm and E-beam applications is referred to as "image blur" (see, e.g., Hinsberg et al., Proc. SPIE, (2000), 3999, 148). Image blur is generally thought to result from two contributing factors: gradient-driven acid diffusion and reaction propagation, the result being a distortion in the developable image compared to the projected aerial image transferred onto the film. This becomes critical in EUV applications because of the need for small features with low line edge roughness (LER). Therefore, a need exists to control the gradient driven acid-diffusion in the resist films.

Most widely reported PAG-bound polymers for EUV applications are ionic in nature, having a sulfonate anion attached to the polymer and a counter ion that is a sulfonium (e.g., triphenylsulfonium) or iodonium (e.g., diphenyliodonium) cation (see, for example, U.S. Pat. No. 8,057,985 B2). This type of polymer has limitations due to low incorporation of PAG 5 mol %), higher polydispersity, and poor solubility in casting solvents. These limitations prevent further improvements in resolution and LER.

Aryl ketone protecting groups have been used in organic synthesis as a photo-labile protecting group for carboxylic acids and in a few polymer-bound non-fluorinated photo-acid generators (e.g., U.S. Pat. No. 4,889,791, U.S. Pat. No. 5,624,777, JPA H10-221852).

A continuing need exists for non-ionic PAGs, which produce strong fluorinated sulfonic acids that remain attached to the polymer.

SUMMARY

Accordingly, a compound is disclosed of formula (1):

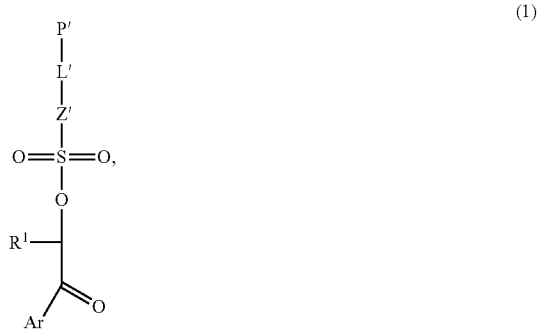

wherein
Ar is a monovalent radical comprising one or more aromatic rings,
L' is a single bond or a divalent $C_0$-$C_{10}$ linking group,
P' is a $C_2$-$C_{20}$ monovalent radical comprising a polymerizable carbon-carbon double bond,
$R^1$ is a monovalent perfluorinated $C_1$-$C_{10}$ radical, wherein $R^1$ has a molecular formula consisting of elements carbon and fluorine, and
Z' is a divalent $C_1$-$C_{10}$ radical having a molecular formula consisting of elements carbon, fluorine, and optionally hydrogen.

Further disclosed is a photo-acid generating polymer (PAG polymer), comprising a non-ionic PAG repeating unit of formula (8):

wherein
the PAG polymer has a polymer backbone,
A' is a trivalent radical comprising a pair of covalently linked carbons which are carbons of the polymer backbone,
Ar is a monovalent aryl radical comprising one or more aromatic rings,
L' is a single bond or a divalent $C_0$-$C_{10}$ linking group,
$R^1$ is a monovalent perfluorinated $C_1$-$C_{10}$ radical, wherein $R^1$ has a molecular formula consisting of elements carbon and fluorine, and Z' is a divalent $C_1-C_{10}$ radical consisting of elements carbon, fluorine, and optionally hydrogen.

Also disclosed is a resist composition, comprising:
an above-described PAG polymer; and
an organic solvent, wherein the PAG polymer is dissolved in the organic solvent, and the resist composition is suitable for forming a resist pattern in a lithographic process.

Further disclosed is a method, comprising:
providing a layered structure comprising a resist layer disposed on a surface of a substrate, the resist layer comprising an above-described PAG polymer;
pattern-wise exposing the resist layer to radiation, thereby forming an exposed resist layer;
baking the exposed resist layer at about 90° C. to about 130° C. for at least 1 second, thereby forming a treated resist layer; and
selectively removing a region of the treated resist layer using a developer, thereby forming a patterned resist layer.

The above-described and other features and advantages of the present invention will be appreciated and understood by those skilled in the art from the following detailed description, drawings, and appended claims.

DETAILED DESCRIPTION

Figure 1A:
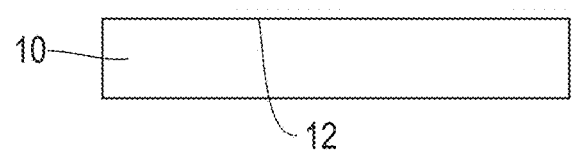
FIGS. 1A to 1E are schematic layer diagrams showing a method of forming a multi-layered structure that includes a topographical patterned layer formed with a resist composition comprising a disclosed PAG polymer.

Disclosed are fluorinated non-ionic photo-acid generators (PAGs) in the form of vinyl polymerizable compounds (PAG monomers), and PAG polymers formed therefrom. The PAG monomers and PAG polymers comprise a fluorinated sulfonate ester of an alpha-hydroxy aryl ketone. The latent sulfonic acid portion and the aryl ketone ester portion of the sulfonate ester group are both fluorinated. Thus, a lithographic exposure of the PAG polymer produces a fluorinated polysulfonic acid and an unbound fluorinated residue of the aryl ketone portion of the sulfonate ester group. Also disclosed are resist compositions comprising the PAG polymers and lithographic methods of forming resist patterns therefrom. Hereinafter, it should be understood that the PAG polymers and PAG monomers are non-ionic prior to a lithographic exposure unless otherwise stated.

The PAG monomers and PAG polymers are capable of forming a sulfonic acid when exposed to radiation of wavelength less than 300 nm (i.e., between 0 nm and 300 nm), including electron beam (E-beam), extreme ultraviolet radiation (EUV, herein ultraviolet wavelengths of about 4 nm to about 124 nm), soft x-ray, x-ray, y-ray, and/or deep ultraviolet radiation (DUV, herein ultraviolet wavelengths of 125 nm to 250 nm such as, for example, ArF excimer laser at 193 nm and KrF excimer laser at 248 nm). Preferably, the PAG monomers and PAG polymers are relatively insensitive to DUV compared to EUV. As a result, EUV exposures of resists layers comprising the PAG polymers can produce lithographic patterns having fewer defects associated with out-of-band (OOB) radiation. In an embodiment, the lithographic process utilizes an ultraviolet wavelength of 13.5 nm (EUV) to expose a resist film comprising the PAG polymer.

The PAG polymers are generally thermally stable up to at least 130° C. In an embodiment, the PAG polymers are thermally stable up to at least 160° C.

The PAG polymers can be used singularly or in combination to form a resist composition. A resist composition can comprise a PAG polymer as the sole photo-acid generating material.

The term "positive-tone development" means the exposed areas of the resist layer are selectively removed during development by a given developer. The exposed areas can become more soluble in a given developer (e.g., aqueous alkaline developer) by, for example, a non-crosslinking chemical reaction induced by the exposure that increases the polarity of the exposed areas.

The term "negative-tone development" means the non-exposed areas of the resist layer are selectively removed during development. In this instance, the exposed areas of the resist layer can become less soluble in a given developer (e.g., organic solvent developers) compared to the non-exposed areas by, for example, a crosslinking reaction or some other chemical change induced by the exposure that lowers the solubility of the exposed areas in the developer.

The term "positive-tone resist pattern" refers to the resist layer containing non-exposed resist that remains after positive-tone development. The examples further below illustrate formation of positive-tone resist patterns using the PAG polymers.

The term "negative-tone resist pattern" refers to the resist layer containing exposed resist that remains after negative tone development.

The PAG polymers can be used to form a positive-tone resist pattern or a negative tone resist pattern.

PAG Monomers

The PAG monomer has a structure according to formula (1):

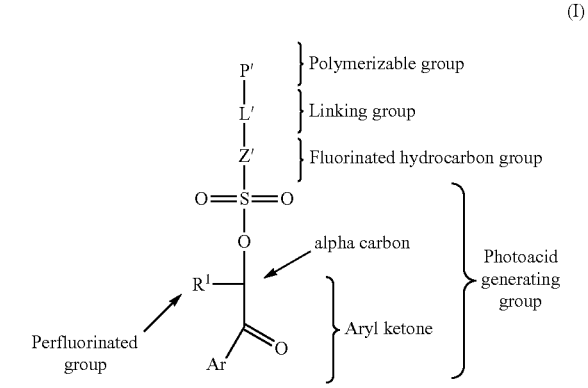

wherein
Ar is a monovalent radical comprising one or more aromatic rings,
L' is a single bond or a divalent $C_0-C_{10}$ linking group, P' is a $C_2$-$C_{20}$ monovalent radical comprising a polymerizable carbon-carbon double bond, $R^1$ is a monovalent perfluorinated $C_1$-$C_{10}$ radical, wherein $R^1$ has a molecular formula consisting of elements carbon and fluorine, and Z' is a divalent $C_1$-$C_{10}$ radical having a molecular formula consisting of elements carbon, fluorine, and optionally hydrogen.

Non-limiting $C_0$-$C_{10}$ linking groups include divalent heteroatoms divalent oxygen (*—O—*), divalent sulfur (*—S—*), secondary amine (*—N(H)—*), sulfoxide (*—S(=O)—*), sulfone (*—S(=O)$_2$—*), sulfonamide (*—NHS(=O)$_2$—*), ketone (*—C(=O)—*), carboxy (*—C(=O)O—*), carbonate (*—OC(=O)O—*), carbamate (*—N(H)C(=O)O—*), urea (*—N(H)C(=O)N(H)—*), tertiary amine groups (*—N(R)—*) wherein R is a $C_1$-$C_{10}$ alkyl or aryl group, and sulfonamide, carbamate and urea groups wherein the nitrogen is substituted with $C_1$-$C_{10}$ alkyl or aryl R groups.

No particular restriction is placed on polymerizable group P', with the proviso that the desirable properties (e.g., film-forming, thermal properties, photo-acid generating properties, and so on) of the PAG polymer formed by the polymerization of the P' group are not adversely affected. The polymerizable carbon-carbon double bond of P' can be present in a vinyl group of a ring structure (e.g., norbornenyl vinyl group, a maleimide vinyl group, and the like), a polymerizable non-cyclic group (e.g., vinyl group of a methacrylate ester, methacrylamide, vinyl sulfone, vinyl ether, vinyl ketone, and the like), or a vinyl group linked to a cyclic group (e.g., styrene, vinyl naphthalene, and the like).

Preferred P' groups include acrylates, methacrylates, acrylamide groups, methacrylamides, vinyl esters, vinyl amides, and vinyl aromatic groups (e.g., substituted and unsubstituted styrenes, vinyl naphthalenes, and the like). These groups are illustrated in Scheme 1, where $R^2$ is hydrogen, methyl, or trifluoromethyl.

Scheme 1

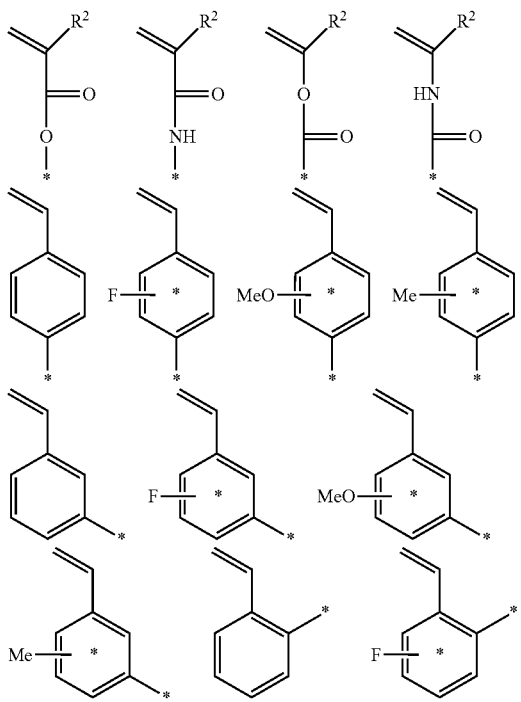

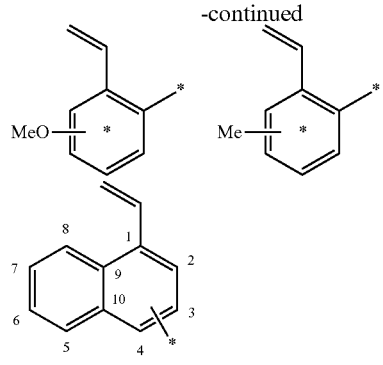

$R^2$ = H, Me, CF$_3$

Herein, an atomic center shown having a bond to an asterisk (also referred to herein as a "starred bond") indicates the atomic center is covalently linked to another unspecified atomic center of the chemical structure. The asterisk represents the unspecified atomic center. In Scheme 1, the aromatic carbon linked to the asterisk is covalently linked to an atomic center of L'. It should be understood that the fluorine, methoxy and methyl groups of the above structure can be linked to any one of the aromatic ring carbons that is not already linked to a vinyl group or to an asterisk. Likewise, the bond to an asterisk of the above vinyl naphthalene structure can emanate from (be linked to) any one of ring carbons 2-8.

In an embodiment, P' is selected from the group consisting of

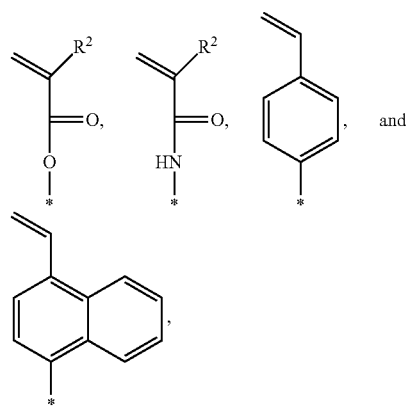

wherein $R^2$ is hydrogen, methyl, or trifluoromethyl.

P' is joined to a partially fluorinated or perfluorinated divalent hydrocarbon group Z' by way of a linking group L'. Herein, a perfluorinated group is a non-charged saturated or unsaturated hydrocarbon group in which each hydrogen has been replaced by fluorine. The molecular formula consists of the elements carbon and fluorine. A perfluorinated group contains no heteroatom (e.g., oxygen, nitrogen, sulfur, and so on). The perfluorinated group can be branched or unbranched, saturated or unsaturated, cyclic or acyclic, aromatic or non-aromatic, or combinations of the foregoing.

When not a single bond, L' can be any suitable divalent $C_0$-$C_{10}$ linking group while observing the above proviso. As non-limiting examples, L' groups include branched or unbranched alkylene groups, a substituted or unsubstituted divalent aromatic groups, ether groups, amide groups, ester groups, carbamate groups (urethane groups), urea groups, and carbonate groups. L' can comprise a combination of one or more of the foregoing functional groups. In the examples further below, L' is:

a single bond,

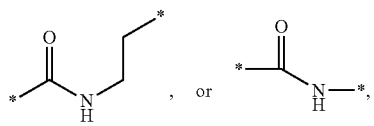

wherein the carbonyl carbon is linked to Z'.

Z' can be acyclic or cyclic, saturated or unsaturated, branched or unbranched, aromatic or non-aromatic, or combinations of any of the foregoing. Z' is linked to the sulfur of the photo-acid generating sulfonate ester group.

Z' can comprise one or more fluorines. As non-limiting examples, Z' can be a partially fluorinated or perfluorinated $C_1$-$C_{10}$ divalent group (e.g., monofluoromethylene (*—C(H)(F)—*), difluoromethylene (*—$CF_2$—*), 1,1-difluoroethane-1,2-diyl (*—$CH_2CF_2$—*), perfluoroethane-1,2-diyl (*—$CF_2CF_2$—*), perfluoropropane-1,3-diyl (*—$CF_2CF_2CF_2$—*)), or a partially fluorinated or perfluorinated aromatic group (e.g., 2-fluorobenzene-1,4-diyl, 3-fluorobenzene-1,4-diyl, 2,3-difluorobenzene-1,4-diyl, 2,5-difluorobenzene-1,4-diyl, 2,6-difluorobenzene-1,4-diyl, 3,5-difluorobenzene-1,4-diyl, 2,3,5-trifluorobenzene-1,4-diyl, 2,3,6-trifluorobenzene-1,4-diyl, 2-fluorobenzene-1,3-diyl, 4-fluorobenzene-1,3-diyl, 5-fluorobenzene-1,3-diyl, 6-fluorobenzene-1,3-diyl, 2,4-difluorobenzene-1,3-diyl, 2,5-difluorobenzene-1,3-diyl, 2,6-difluorobenzene-1,3-diyl, 4,5-difluorobenzene-1,3-diyl, 4,6-difluorobenzene-1,3-diyl, 5,6-difluorobenzene-1,3-diyl, 2,4,5-trifluorobenzene-1,3-diyl, 2,4,6-trifluorobenzene-1,3-diyl, 2,5,6-trifluorobenzene-1,3-diyl, 4,5,6-trifluorobenzene-1,3-diyl, tetrafluorobenzene-1,4-diyl, tetrafluorobenzene-1,3-diyl).

In the examples further below, Z' is:

(difluoromethylene)

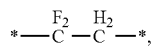

(1,1-difluoroethane-1,2-diyl group)

wherein the carbon bearing the fluorines is linked to the sulfonate sulfur, or

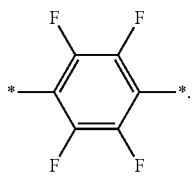

(tetrafluorobenzene-1,4-diyl)

The aryl ketone portion of the sulfonate ester group comprises a perfluorinated alkyl group $R^1$, which is linked to the same alpha carbon of the aryl ketone group as the oxygen of the sulfonate ester.

The perfluorinated group $R^1$ can be branched or unbranched, saturated or unsaturated, cyclic or acyclic, aromatic or non-aromatic, or combinations of the foregoing. Preferably, $R^1$ is a perfluorinated alkyl group, wherein each hydrogen of the corresponding hydrocarbon alkyl group is replaced by fluorine. Exemplary $R^1$ groups include trifluoromethyl (*—$CF_3$), perfluoroethyl (*—$CF_2CF_3$), perfluoro-n-propyl (*—$CF_2CF_2CF_3$), perfluoroisopropyl (*—$CF(CF_3)_2$), perfluoro-n-butyl (*—$CF_2CF_2CF_2CF_3$), perfluoroisobutyl (*—$CF_2CF(CF_3)_2$), perfluoro-n-pentyl (*—$CF_2(CF_2)_3CF_3$), and pentafluorophenyl. In an embodiment, $R^1$ is selected from the group consisting of trifluoromethyl and perfluoroethyl.

More specific aryl ketone groups have a structure according to formula (2):

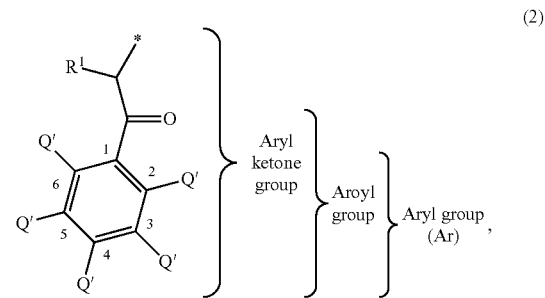

wherein carbons of the aromatic ring are numbered 1-6, each Q' is selected from the group consisting of hydrogen, halides, alkyl groups, fluoroalkyl groups, cycloalkyl groups, alkoxy groups, substituted and unsubstituted aryl groups, and substituted and unsubstituted aryloxy groups, $R^1$ is a monovalent perfluorinated $C_1$-$C_{10}$ radical, wherein $R^1$ has a molecular formula consisting of elements carbon and fluorine, and optionally, an adjacent pair of Q' groups completes a ring.

Exemplary non-limiting Q' groups include methyl, ethyl, isopropyl, t-butyl, hexyl, cyclohexyl, norbornyl, trifluoromethyl, trifluoroethyl, methoxy, ethoxy, propyloxy, butoxy, t-butoxy, phenyl, ortho-fluorophenyl, meta-fluorophenyl, para-fluorophenyl, pentafluorophenyl, and naphthyl.

Exemplary non-limiting aryl groups Ar include those of Scheme 2.

Scheme 2

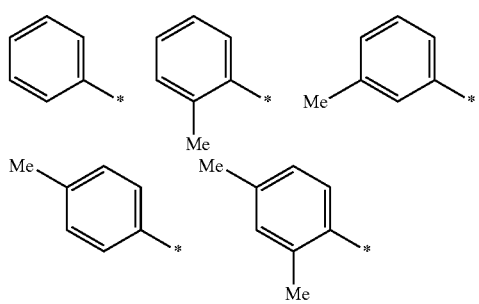

-continued
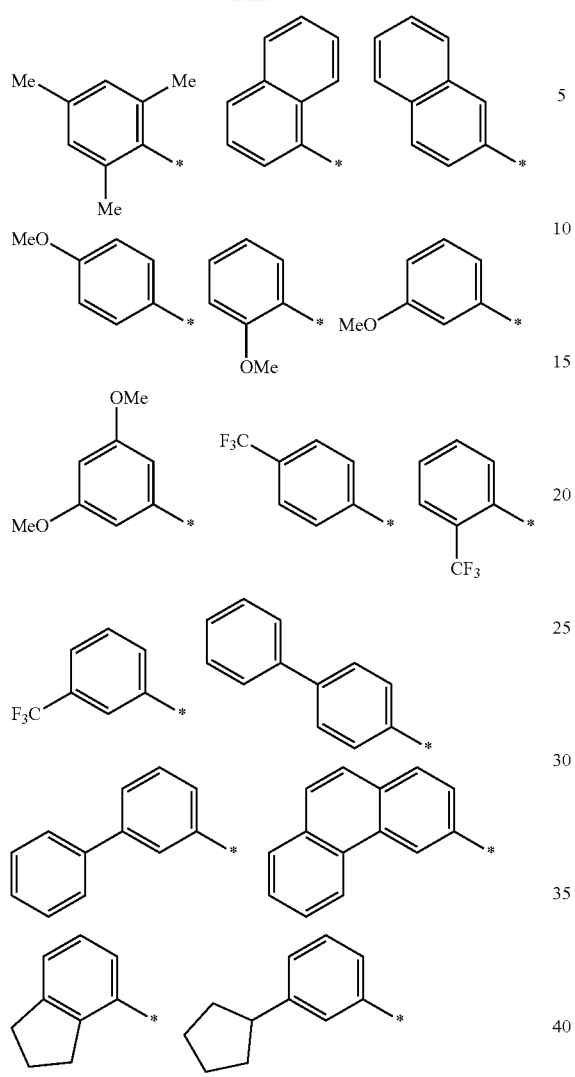
In an embodiment, Ar is selected from the group consisting of
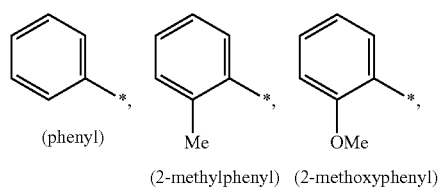
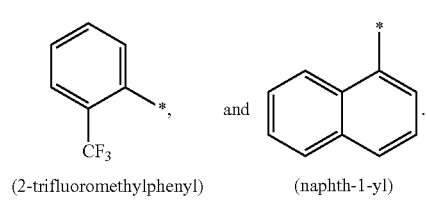
Exemplary non-limiting aroyl groups include those of Scheme 3.
Scheme 3
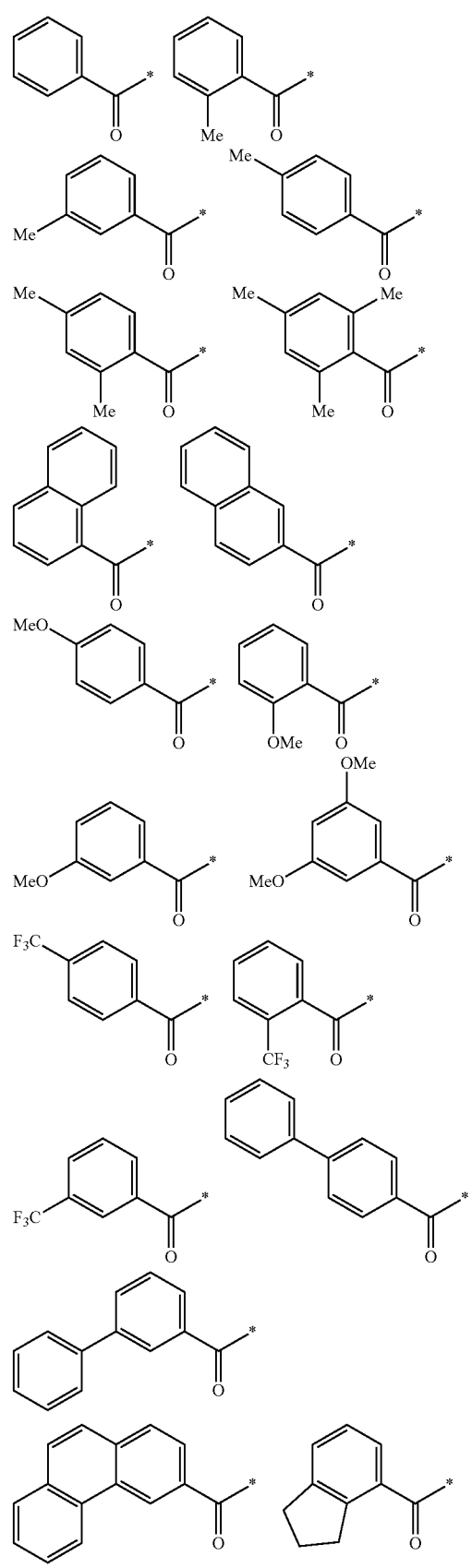

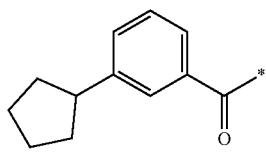
Exemplary non-limiting aryl ketone groups include those of Scheme 4.
Scheme 4
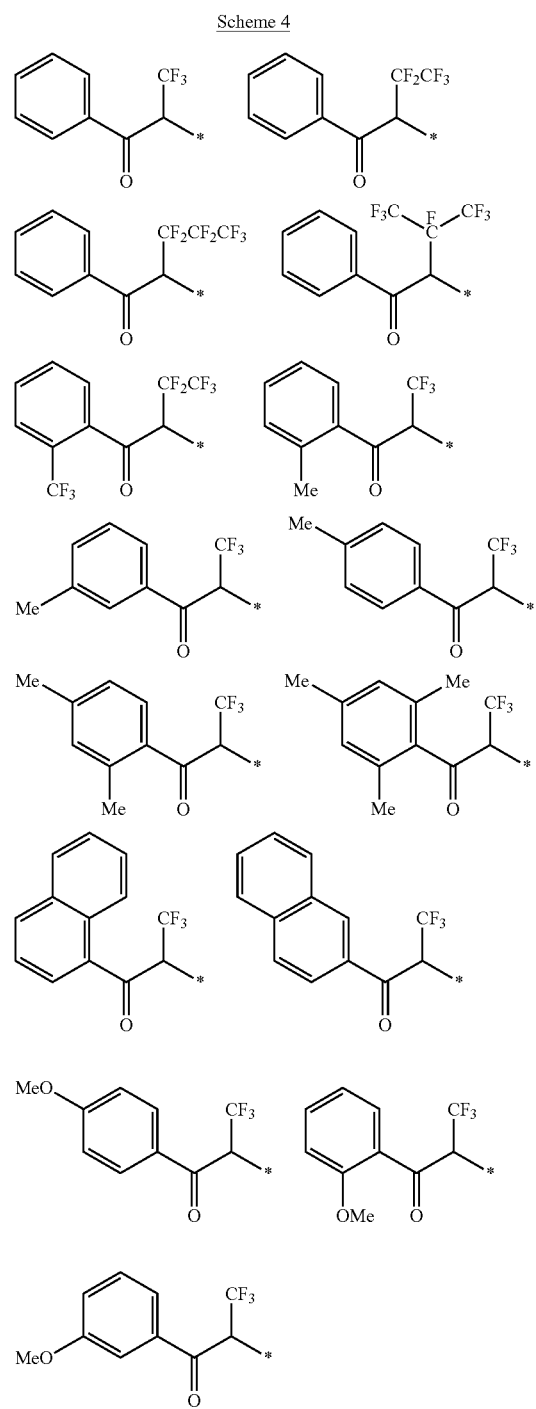
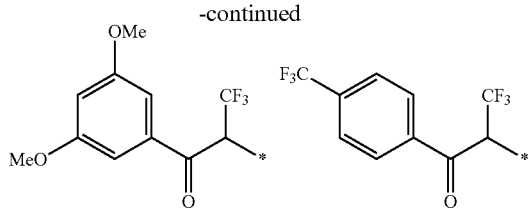
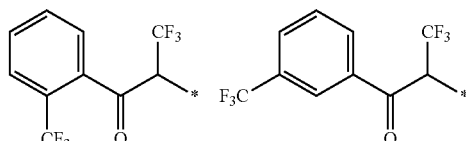
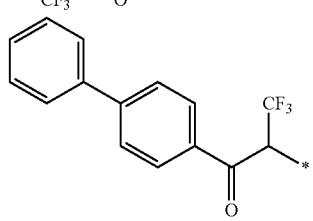
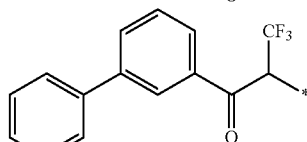
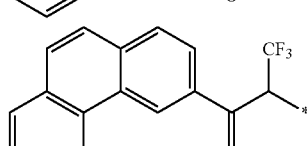
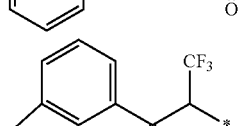
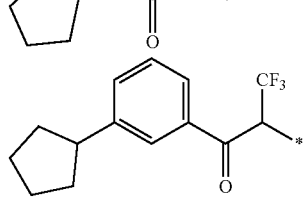
More specific PAG monomers have a structure according to formula (3):
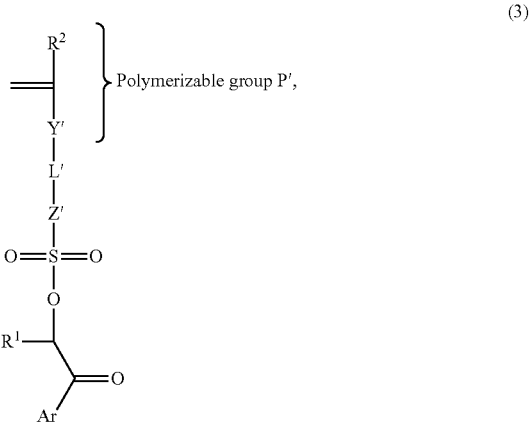

wherein

Ar is a monovalent radical comprising one or more aromatic rings,

L' is a single bond or a divalent $C_0$-$C_{10}$ linking group, $R^1$ is a monovalent perfluorinated $C_1$-$C_{10}$ radical, wherein $R^1$ has a molecular formula consisting of elements carbon and fluorine, $R^2$ is a monovalent radical selected from the group consisting of hydrogen, methyl, and trifluoromethyl, Y' is a divalent radical selected from the group consisting of

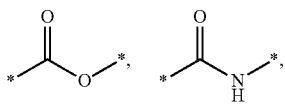

and aromatic groups comprising one or more aromatic rings, and

Z' is a divalent $C_1$-$C_{10}$ radical consisting of elements carbon, fluorine, and optionally hydrogen.

As shown above, the polymerizable group P' in formula (3) is the group

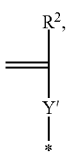

wherein $R^2$ is a monovalent radical selected from the group consisting of hydrogen, methyl, and trifluoromethyl, Y' is a divalent radical selected from the group consisting of

and aromatic groups comprising one or more aromatic rings, and

Y' is linked to L'.

More specific Y' aromatic groups include those of Scheme 5.

Scheme 5

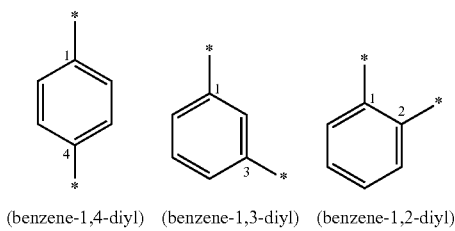

(benzene-1,4-diyl)    (benzene-1,3-diyl)    (benzene-1,2-diyl)

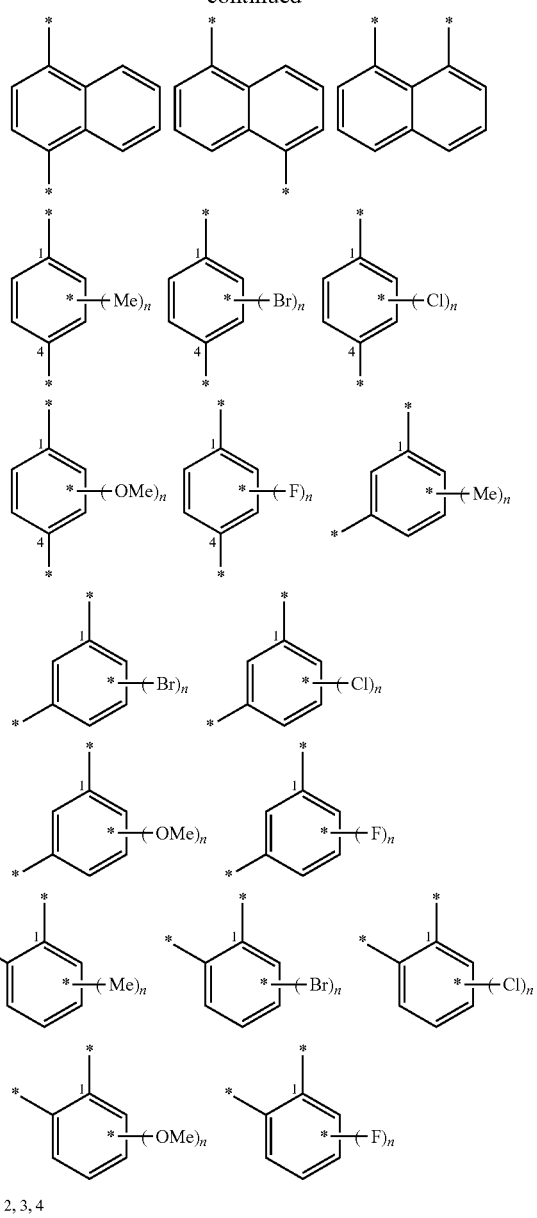

n = 1, 2, 3, 4

One of the aromatic carbons bearing a starred bond in Scheme 5 is linked to L' of formula (3). The remaining aromatic carbon bearing a starred bond is linked to the polymerizable group of formula (3).

In an embodiment, Y' is

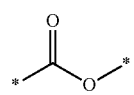

and the PAG monomer is a methacrylate ester compound. In another embodiment, Y' is benzene-1,4-diyl.

Non-limiting examples of PAG monomers include those of Scheme 6. For clarity, P', Y', L', and Z' of formula (3) are indicated.

Scheme 6
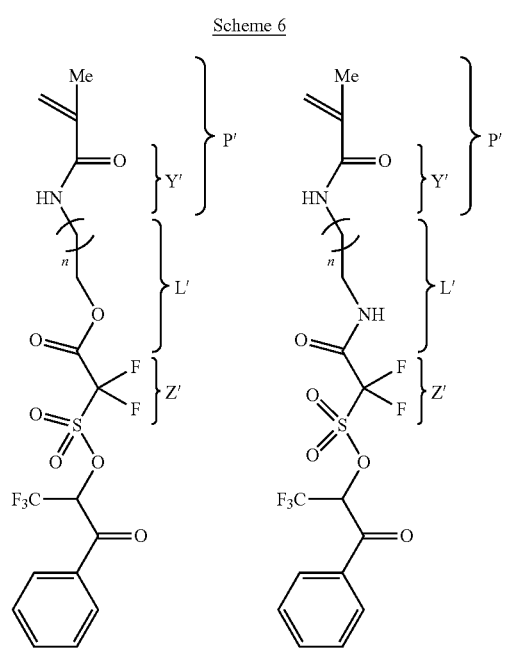
PAG-1
PAG-2
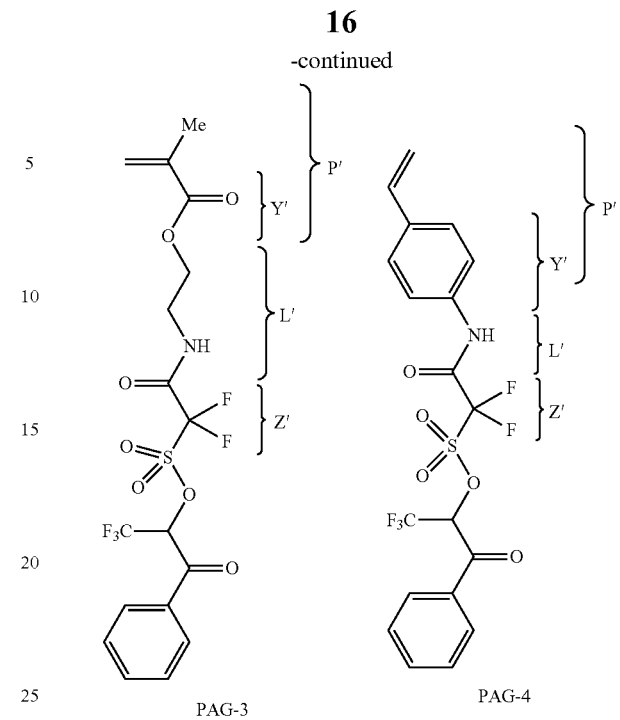
PAG-3
PAG-4
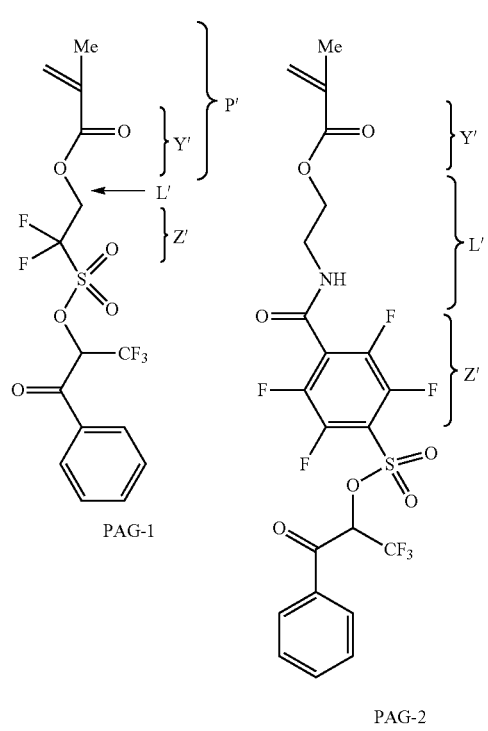
n = 1, 2, 3, 4, 5, 6, 7, 8, 9
The PAG monomers can be prepared according to the reaction sequences of Scheme 7 below using compounds of formulas (4), (5), (6), and (7), where R', Z', L', and P' have the meanings discussed above. X' is a leaving group (e.g., fluoride, chloride, bromide, iodide).
Scheme 7
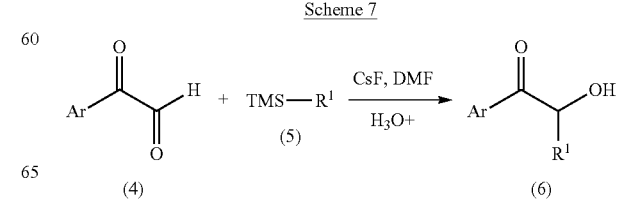

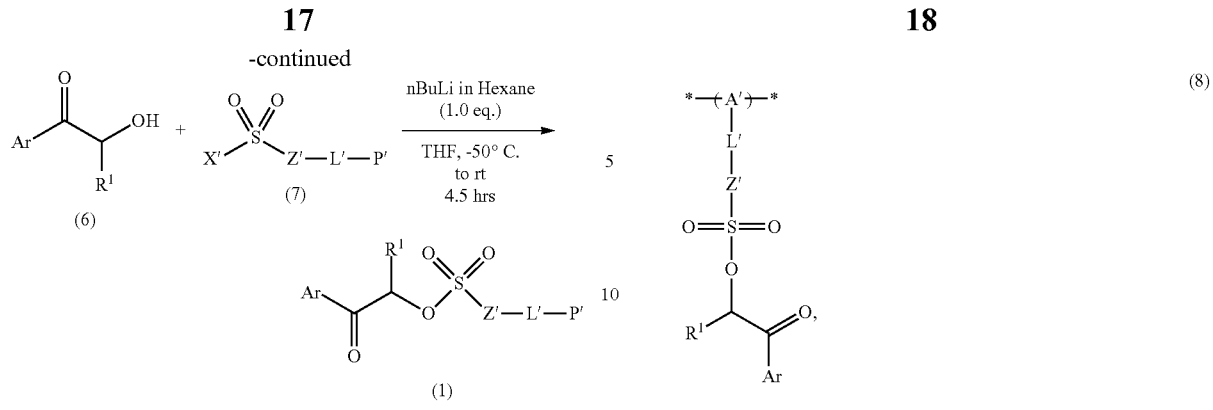

X' = F or Cl

Exemplary solvents for the above reactions include dichloromethane, chloroform, toluene, diethyl ether, carbon tetrachloride, 1,2-dichloroethane, tetrachloroethylene, chlorobenzene, dimethylformamide and acetonitrile. The solvents can be used singularly or in combination.

Sulfonyl halide compounds of formula (7) can be prepared by the reaction of a carboxylic acid halide-sulfonyl halide compound (referred to herein as bis-acid halide) with a polymerizable monomer comprising a nucleophilic group capable of reacting selectively with the carboxylic acid halide group. Exemplary bis-acid halides include the compounds of Scheme 8.

Scheme 8

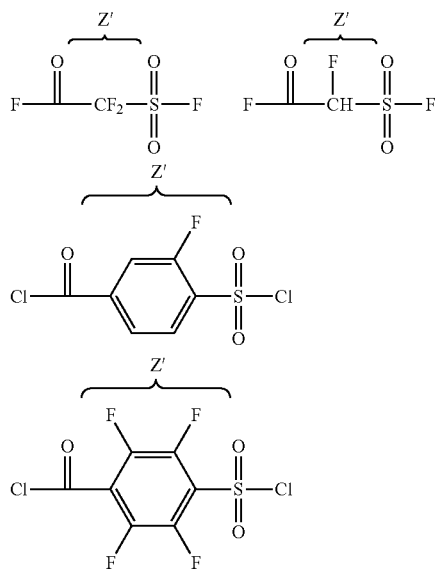

Non-limiting examples of polymerizable monomers comprising a nucleophilic group capable of reacting selectively at the carboxylic acid halide site include 4-aminostyrene, 2-aminoethyl methacrylate, 2-hydroxyethyl methacrylate, 4-hydroxystyrene, and the like.

The PAG monomers can be used singularly or in combination to prepare a PAG polymer.

PAG Polymers

The PAG polymer comprises a photo-acid generating repeating unit (referred to herein as PAG repeating unit, also referred to below as "first repeating unit") having a structure according to formula (8):

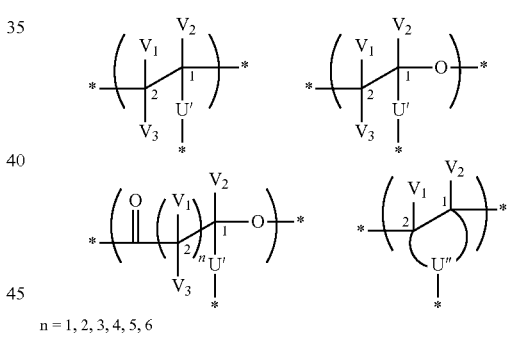

wherein
the PAG polymer has a polymer backbone,
A' is a trivalent radical comprising a pair of covalently linked carbons which are carbons of the PAG polymer backbone,
Ar is a monovalent aryl radical comprising one or more aromatic rings,
L' is a single bond or a divalent $C_0$-$C_{10}$ linking group,
$R^1$ is a monovalent perfluorinated $C_1$-$C_{10}$ radical, wherein $R^1$ has a molecular formula consisting of elements carbon and fluorine, and
Z' is a divalent $C_1$-$C_{10}$ radical consisting of elements carbon, fluorine, and optionally hydrogen.

The pair of covalently linked carbons of A' is an ethylenic group having one or substituents. Non-limiting examples of A' groups include the following structures

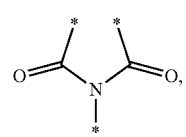 [SMILES: *C(=O)N(*)C(*)=O]

n = 1, 2, 3, 4, 5, 6 wherein
n is a positive integer having a value of 1-6,
$V_1$, $V_2$, and $V_3$ are independent monovalent radicals selected from the group consisting of hydrogen, halides, and substituents comprising 1 to 6 carbons,
U' is a single bond or a divalent radical linked to L', and
U" is a trivalent radical that completes a ring with carbon 1 and carbon 2 and is linked to L'.

More specific U" groups include

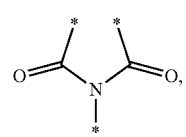

wherein A' is a maleimide:

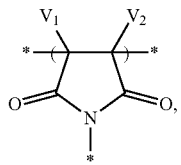

wherein $V_1$ and $V_2$ are defined as above, and the imide nitrogen is linked to L'.

More specific PAG repeating units have a structure according to formula (9):

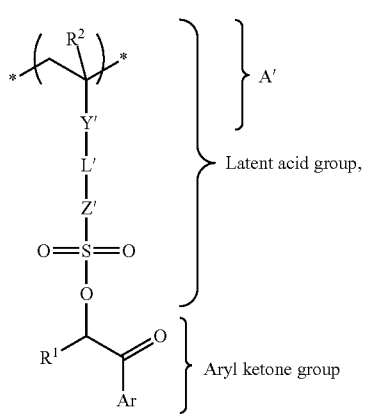

wherein

Ar is a monovalent radical comprising one or more aromatic rings,

L' is a single bond or a divalent $C_0$-$C_{10}$ linking group, $R^1$ is a monovalent perfluorinated $C_1$-$C_{10}$ radical, wherein $R^1$ has a molecular formula consisting of elements carbon and fluorine, $R^2$ is a monovalent radical selected from the group consisting of hydrogen, methyl, and trifluoromethyl, Y' is a divalent radical selected from the group consisting of

and aromatic groups comprising one or more aromatic rings, and

Z' is a divalent $C_1$-$C_{10}$ radical consisting of elements carbon, fluorine, and optionally hydrogen.

As shown above, the group A' in formula (8) is

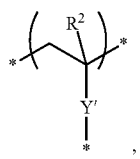

wherein $R^2$ is a monovalent radical selected from the group consisting of hydrogen, methyl, and trifluoromethyl, Y' is a divalent radical selected from the group consisting of

and aromatic groups comprising one or more aromatic rings, and

Y' is linked to L'.

In an embodiment, Y' is

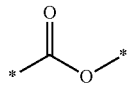

and the oxygen is linked to L'. In another embodiment, Y' is benzene-1,4-diyl.

Non-limiting examples of PAG repeating units include those of Scheme 9. For clarity, Y', L', and Z' of formula (9) are indicated.

Scheme 9

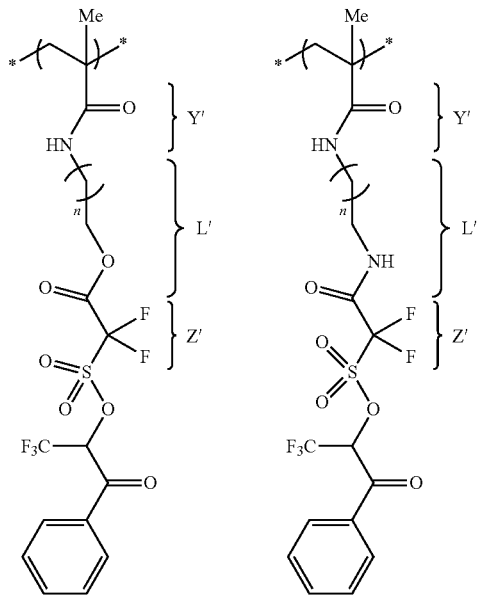

-continued

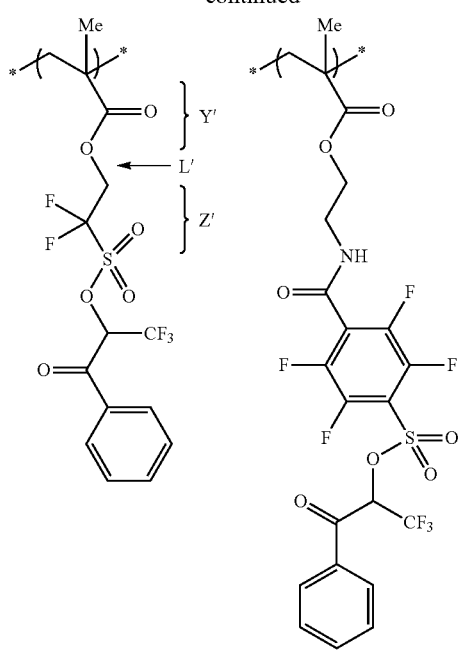

-continued

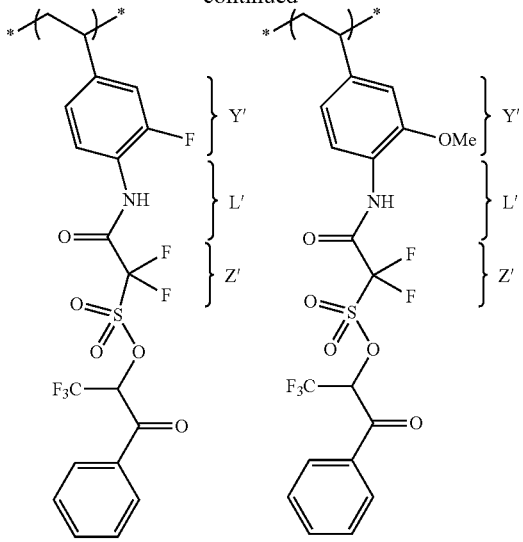

n = 1, 2, 3, 4, 5, 6, 7, 8, 9

The PAG polymer can be a homopolymer, random copolymer, or block copolymer chain of the PAG repeating unit. A given PAG polymer chain can comprise the PAG repeating units singularly or in combination.

The PAG polymer comprises the PAG repeating unit in an amount of more than 0 mol %, and up to 100 mol %, based on total moles of monomers used to prepare the PAG polymer. When the PAG polymer functions as a photo-acid generator and a resin for chemical amplification, discussed in more detail below, the PAG polymer preferably comprises the PAG repeating unit in an amount of about 1 mol % to about 20 mol %, more preferably 1 mol % to 15 mol %, based on total moles of repeating units of the PAG polymer.

The PAG polymer can have a number average molecular weight (Mn) of about 100 to about 1,000,000, more particularly 1,000 to about 100,000, and even more particularly 2,000 to about 20,000, as measured by gel permeation chromatography (GPC). The PAG polymer molecular weight is also discussed in more detail below.

Upon exposure to radiation (e.g., E-beam, EUV, x-ray), the PAG polymer comprising the PAG repeating unit of formula (8) is converted to a photo-acid polymer comprising a repeating unit bearing a sulfonic acid (also referred to herein as the "photo-acid repeating unit"). The photo-acid repeating unit has a structure according to formula (10):

(10)

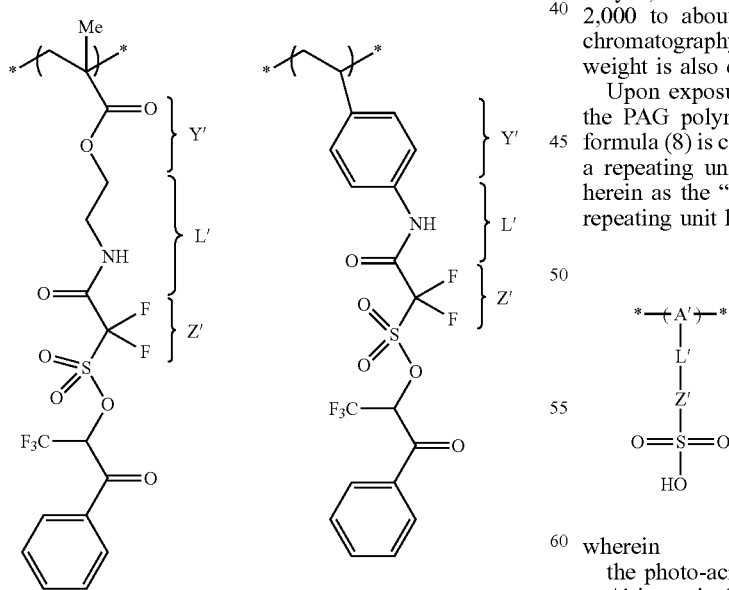

wherein
the photo-acid polymer has a polymer backbone,
A' is a trivalent radical comprising a pair of covalently linked carbons that are carbons of the photo-acid polymer backbone,
L' is a single bond or a divalent $C_0$-$C_{10}$ linking group, and
Z' is a divalent $C_1$-$C_{10}$ radical consisting of elements carbon, fluorine, and optionally hydrogen.

The sulfonic acid group is a strong acid capable of catalyzing a reaction (e.g., deprotection of an acid-labile group) suitable for chemical amplification in a lithographic patterning process.

Depending on the purpose of use of the PAG polymer, the PAG polymer can comprise the PAG repeating unit in combination with or without a second repeating unit containing an acid-labile group or a cross-linking site. In either instance, the PAG polymer can have any other repeating unit (referred to herein as an "auxiliary repeating unit"). The term "auxiliary repeating unit" means a repeating unit that does not correspond to the PAG repeating unit of formula (8) or formula (9) and does not correspond to the second repeating unit containing an acid-labile group or cross-linking site. The term "auxiliary monomer" means a vinyl polymerizable monomer. It should be understood that herein the term "vinyl polymerizable monomer" includes any compound comprising a polymerizable carbon-carbon double bond (e.g., vinyl aromatics (such as styrenes and vinyl naphthalenes), methacrylates, acrylates, methacrylamides, acrylamides, vinyl sulfones, vinyl ethers, vinyl esters, vinyl amides, norbornenes, maleic anhydrides, maleimides and the like) capable of forming a repeating unit of the PAG polymer. In an embodiment, the second repeating unit comprises an alcohol or carboxylic acid group protected by an acid labile group. That is, the acid labile group is capable of being removed by an acid, thereby generating the respective alcohol or carboxylic acid group, which is pendent to the deprotected PAG polymer backbone.

The PAG repeating units can be present singularly or in combination with other PAG repeating units. The second repeating units can be present singularly or in combination with other second repeating units. The auxiliary repeating units can be present singularly or in combination with other auxiliary repeating units.

Thus, the presence of the second repeating units and the auxiliary repeating units in the PAG polymer is optional. As an example, the PAG polymer can be a homopolymer of the PAG repeating unit as obtained by homopolymerization of the disclosed PAG monomer. Alternatively, the PAG polymer can be a copolymer consisting essentially of auxiliary repeating units in addition to the PAG repeating unit. In these instances, the PAG polymer cannot function as a positive resist resin capable of chemical amplification, but can function as a photo-acid generator in a resist composition comprising a second polymer resin that comprises acid-labile groups capable of chemical amplification. For such use, the PAG polymer can contain 0.1 mol % to 100 mol %, preferably 1 to 100 mol %, more preferably 2 mol % to 100 mol %, of the PAG repeating unit, the balance being one or more auxiliary repeating units. Herein, mol % of a given repeating unit is based on total moles of all repeating units of the given polymer.

Alternatively, the PAG polymer can consist essentially of the PAG repeating unit and the second repeating unit containing the acid-labile group or cross-linking site. In this instance, the PAG polymer can have properties suitable for photo-acid generation and chemical amplification in a lithographic process. The PAG polymer can comprise 0.1 mol % to 90 mol %, preferably 0.5 mol % to 50 mol %, more preferably 1 to 20 mol % of the PAG repeating unit, the balance being the second repeating unit containing the acid-labile group or cross-linking site.

If the amount of the PAG repeating unit exceeds 90 mol % of the PAG polymer, the PAG polymer can adequately function as a photo-acid generator. However, little or no benefit with respect to chemical amplification is provided by the PAG polymer comprising less than 10 mol % of the second repeating unit containing the acid-labile group.

The PAG polymer can comprise i) the PAG repeating unit, ii) the second repeating unit containing the acid-labile group or cross-linking site, and iii) the auxiliary repeating unit. In this case, the PAG polymer preferably contains 0.1 mol % to 70 mol %, more preferably 1 mol % to 60 mol %, and most preferably 10 mol % to 50 mol % of the auxiliary repeating unit, 0.1 mol % to 15 mol % of the PAG repeating unit, the balance being the second repeating unit containing the acid-labile group or cross-linking site.

The PAG polymer can be used singularly or in combination with a second PAG polymer and/or PAG compound. If the amount of the PAG repeating unit is less than 0.1 mol % of the PAG polymer, a second photo-acid generator can be employed in order for the resist composition to maintain sufficient photosensitivity to high energy radiation. Substrate adhesion and etching resistance of the PAG polymer are generally adversely affected when the amount of the auxiliary repeating unit is less than 0.1 mol % of the PAG polymer. Moreover, the photo-acid generating properties of the PAG polymer and the utility of the PAG polymer as a positive or negative resist (i.e., the capability of the PAG polymer to undergo chemical amplification) are generally adversely affected when the amount of the auxiliary repeating unit exceeds 70 mol %.

When the PAG polymer functions as the photo-acid generator and a positive or negative resist resin capable of chemical amplification, the PAG polymer preferably contains 1 mol % to 15 mol % of a PAG repeating unit and 2 mol % to 85 mol % of a second repeating unit containing the acid-labile group or cross-linking site, with the balance being the auxiliary repeating unit. More preferably, the PAG polymers contain 1 mol % to 15 mol % of the PAG repeating unit, and 4 mol % to 70% of the second repeating unit containing the acid-labile group or cross-linking site, with the balance being the auxiliary repeating unit. Most preferably, the PAG polymers contain 4 mol % to 10 mol % of the PAG repeating unit, and 15 mol % to 60 mol % of the second repeating unit containing the acid-labile group or cross-linking site, with the balance being the auxiliary repeating unit. However, the composition of the PAG polymer is not limited to the above-described ranges.

When the PAG polymer functions as both the photo-acid generating component and the base resin capable of chemical amplification, the PAG polymer can have a number average molecular weight (Mn) of 1,000 to 1,000,000, more particularly 2,000 to 500,000, even more particularly 5,000 to about 15,000, as measured by gel permeation chromatography (GPC).

When the resist composition is prepared with a PAG polymer and a separate base resin, the PAG polymer can have a number average molecular weight (Mn) of 1,000 to 100,000, preferably 2,000 to 50,000. If the number average molecular weight of the PAG polymer is less than 1,000, the PAG polymer can diffuse and migrate into unexposed portions of the resist film during heat treatment after patternwise exposure, causing deterioration in pattern resolution. Solubility of the PAG polymer in a given solvent and/or formation of uniform resist films can be adversely affected when the number average molecular weight of the PAG polymer exceeds 1,000,000.

The molecular weight distribution (Mw/Mn, or polydispersity index (PDI)) of the PAG polymer is preferably in the range of 1.01 to about 2.5, more preferably 1.01 to about 1.75.

When the second repeating unit contains an acid-labile group comprising a protected acid group capable of being deprotected by an acid, the PAG polymer can have dual properties of photo-acid generation and chemical amplification suitable for a positive resist composition. That is, upon exposure, the PAG polymer generates an acid that during a subsequent heat treatment catalyzes the thermal cleavage of the acid-labile groups to form additional acid groups in regions of the exposed PAG polymer, thereby altering (i.e., increasing) the solubility of the exposed PAG polymer relative to non-exposed PAG polymer in a given aqueous base developer.

When the second repeating unit contains a cross-linking site, the PAG polymer can have dual properties of photo-acid generation and chemical amplification suitable for a negative resist composition. That is, upon exposure, the PAG polymer generates an acid that during a subsequent heat treatment catalyzes a cross-linking reaction at a cross-linking site of the PAG polymer (e.g., alcohol group, carboxylic acid group), thereby altering (i.e., decreasing) the solubility of the exposed PAG polymer relative to non-exposed PAG polymer in a given aqueous base developer.

Dry etching resistance, standard developer compatibility, substrate adhesion, resist profile and other resist characteristics such as resolution, heat resistance and sensitivity can be controlled by the types and amounts of second repeating units and auxiliary repeating units used in combination with the PAG repeating units.

Second repeating unit bearing an acid-labile group

The second repeating units containing an acid-labile group can have a structure in accordance with formula (13):

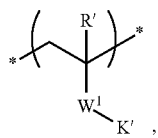

(13)

wherein

R' is a monovalent radical selected from the group consisting of H, F, $C_1$-$C_3$ alkyl groups, fluorine-containing $C_1$-$C_3$ alkyl groups, and cyano, $W^1$ is a divalent linking group selected from the group consisting of single bond and groups comprising 1 or more carbons,

*—K' is a protected alcohol *—O-G' or a protected carboxylic acid group *—C(=O)—OG', wherein G' is an acid-labile protecting group.

Other acid-labile second repeating units can have a structure in accordance with formula (14):

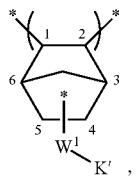

(14)

wherein

W' is a divalent linking group selected from the group consisting of single bond and groups comprising 1 or more carbons, and

*—K' is a protected alcohol *—O-G' or a protected carboxylic acid group *—C(=O)—OG', wherein G' is an acid-labile protecting group.

The acid-labile protecting group G' refers to a group capable of being removed from the second repeating unit when heated in the presence of an acid (e.g., photo-generated acid), thereby generating a deprotected second repeat unit comprising a sidechain alcohol or carboxylic acid group. Preferably, G' is capable of forming a tertiary carbonium ion when heated in the presence of the photo-generated acid. When K' is a protected alcohol group, K' can be an ether, acetal, ketal, orthoester, or carbonate (e.g., t-Boc group), which is capable of undergoing deprotection by an acid to form an alcohol group pendent to the deprotected PAG polymer backbone. When K' is a protected carboxylic acid group, K' can be a tertiary ester, acetal ester, ketal ester, orthoester, or carbonate ester (e.g., *—C(=O)—O-Boc, wherein Boc is t-butoxycarbonyl) which is capable of undergoing deprotection by an acid to form an carboxylic acid group pendent to the deprotected PAG polymer backbone.

The second repeating units that contain a crosslinking site can have a structure in accordance with formula (15):

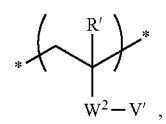

(15)

wherein

R' is a monovalent radical selected from the group consisting of H, F, $C_1$-$C_3$ alkyl groups, fluorine-containing $C_1$-$C_3$ alkyl groups, and cyano, $W^2$ is a divalent linking group selected from the group consisting of single bond and groups comprising 1 or more carbons, and V' is *—O—H or *—(C=O)—OH.

Other second repeating units containing a cross-linking site can have a structure in accordance with formula (16):

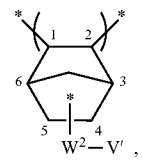

(16)

wherein $W^2$ is a divalent linking group selected from the group consisting of single bond and groups comprising 1 or more carbons, and V' is *—O—H or *—(C=O)—OH.

The hydroxyl group of V refers to a substantially neutral alcoholic hydroxyl group that is not generally involved in the dissolution of the resin into an alkaline solution but is cross-linked with a cross-linking agent by a hydroxyl-related reaction (e.g., ester bonding, ether bonding, ureide bonding, etc.) so as to make the alkali-soluble resin component insoluble in an aqueous alkali solution.

Linking groups $W^1$ and $W^2$ $W^1$ is a divalent linking group formed by one functional group, or two or more functional groups in combination, selected from the group consisting of a single bond,

*—(CR$^{13}$R$^{14}$)$_n$—* where n is an integer of 1 to 10, *—O—*, *—C(=O)—*, *—C(=O)—O—* or *—O—C(=O)—*, a divalent alicyclic hydrocarbon group, a divalent aromatic hydrocarbon group, a divalent heterocyclic group, a thioether group, an ester group, an amide group, a sulfonamide group, a urethane group, and a urea group. No particular limitation is placed on monovalent groups R$^{13}$ and R$^{14}$ in the substituted or unsubstituted methylene group represented by *—(CR$^{13}$R$^{14}$)—*. R$^{13}$ and R$^{14}$ each independently represent a hydrogen atom, a halogen atom, a hydroxy group, or a monovalent C$_1$-C$_{30}$ group selected from the group consisting of substituted or unsubstituted alkyl groups, substituted or unsubstituted aliphatic hydrocarbon groups, alkoxy groups, substituted or unsubstituted aryl groups, and substituted or unsubstituted condensed polycyclic aromatic groups. Each of these monovalent groups can contain a fluorine atom, an oxygen atom, a sulfur atom, a nitrogen atom or a carbon-carbon double bond. Moreover, R$^{13}$ and R$^{14}$ can be the same or different and can together form a ring structure, preferably an alicyclic hydrocarbon structure, with another atom in the second repeating unit. R$^{13}$ and/or R$^{14}$ are exemplified as follows.

R$^{13}$ and/or R$^{14}$ can be an acyclic alkyl group of 1 to 30 carbon atoms, preferably 1 to 12 carbon atoms. Examples of the acyclic alkyl groups include methyl, ethyl, n-propyl, propyl, n-butyl, 1-methylpropyl, 2-methylpropyl, tert-butyl, n-pentyl, i-pentyl, 1,1-dimethylpropyl, 1-methylbutyl, 1,1-dimethylbutyl, n-hexyl, n-heptyl, i-hexyl, n-octyl, i-octyl, 2-ethylhexyl, n-nonyl, n-decyl, n-undecyl and n-dodecyl. Lower alkyl groups are preferred. Particularly preferred are methyl, ethyl, n-propyl and i-propyl. Herein, the term "lower" means that the group to which the term is attached has 1 to 4 carbon atoms and, in the case where the group is cyclic, has 3 to 7 carbon atoms.

R$^{13}$ and/or R$^{14}$ can be an acyclic substituted alkyl group obtained by substitution of one hydrogen atom or two or more hydrogen atoms of an above-described alkyl group with a C$_1$-C$_4$ alkoxy group, a halogen atom, an acyl group, an acyloxy group, a cyano group, a hydroxy group, a carboxy group, an alkoxycarbonyl group, or a nitro group, and is preferably a fluorine-substituted alkyl group (i.e., fluoroalkyl group). Examples of acyclic substituted alkyl groups R$^{13}$ and/or R$^{14}$ are lower fluoroalkyl groups such as trifluoromethyl, pentafluoroethyl, 2,2,2-trifluoroethyl, n-heptafluoropropyl, 2,2,3,3,3-pentafluoropropyl, 3,3,3-trifluoropropyl and hexafluoropropyl.

R$^{13}$ and/or R$^{14}$ can be an alicyclic hydrocarbon group or an alicyclic hydrocarbon group formed by R$^{13}$ and R$^{14}$ together. The alicyclic hydrocarbon group can be monocyclic or polycyclic. Examples of the alicyclic hydrocarbon groups are those having a monocyclo, bicyclo, tricyclo, or tetracyclo structure of 3 or more carbon atoms, preferably 3 to 30 carbon atoms, more preferably 3 to 25 carbon atoms. The alicyclic hydrocarbon group can have a substituent.

A monocyclic hydrocarbon group R$^{13}$ and/or R$^{14}$ preferably has 3 to 12 ring carbon atoms, more preferably 3 to 7 ring carbon atoms. Examples of such a monocyclic hydrocarbon group a include cyclopropyl, cyclobutyl, cyclopentyl, cyclohexyl, cycloheptyl, cyclooctyl, cyclodecanyl, cyclododecanyl, and 4-tert-butylcyclohexyl. A polycyclic hydrocarbon group R$^{13}$ and/or R$^{14}$ preferably has 7 to 15 ring carbon atoms. Examples of such a polycyclic hydrocarbon groups include adamantyl, noradamantyl, decalinyl (monovalent hydrocarbon structure of decalin), tricyclodecanyl, tetracyclododecanyl, norbornyl and cedryl (monovalent hydrocarbon structure of cedrol). The alicyclic hydrocarbon group can be a spiro ring, preferably having 3 to 6 carbon atoms. Examples of spiro ring are adamantyl, decalinyl, norbornyl, cedryl, cyclohexyl, cycloheptyl, cyclooctyl, cyclodecanyl, cyclododecanyl and tricyclodecanyl. One or more hydrogen atoms on the ring carbons of the above organic groups, or one or more hydrogen atoms of the above linking group, can be each independently substituted with a substituent such as C$_1$-C$_{30}$ alkyl or substituted alkyl group, hydroxy group, alkoxy group, carboxyl group, and/or alkoxycarbonyl group. One or more hydrogen atoms of the substituent can further be substituted with fluorine or trifluoromethyl.

Herein, each of C$_1$-C$_{30}$ alkyl groups R$^{13}$ and/or R$^{14}$ is preferably a lower alkyl group, more preferably an alkyl group selected from the group consisting of methyl, ethyl, propyl and isopropyl. As the substituent of the substituted alkyl group, there can be used a hydroxy group, a halogen atom, an alkoxy group, alkoxy carbonyl group, and the like. The alkoxy group preferably has 1 to 4 carbon atoms, as exemplified by methoxy, ethoxy, propoxy and butoxy. Exemplary alkoxy carbonyl groups include methoxycarbonyl, ethoxycarbonyl and isopropoxycarbonyl.

Aryl groups R$^{13}$ and/or R$^{14}$ can be substituted or unsubstituted and have 1 to 30 carbon atoms. It is preferable that, when the aryl group is monocyclic, the monocyclic aryl group has 3 to 12 ring carbon atoms, more preferably 3 to 6 ring carbon atoms. Examples of aryl groups R$^{13}$ and/or R$^{14}$ include phenyl, biphenyl, terphenyl, o-tolyl, m-tolyl, p-tolyl, p-hydroxyphenyl, p-methoxyphenyl, mesityl, o-cumenyl, 2,3-xylyl, 2,4-xylyl, 2,5-xylyl, 2,6-xylyl, 3,4-xylyl, 3,5-xylyl, o-fluorophenyl, m-fluorophenyl, p-fluorophenyl, o-trifluoromethylphenyl, m-trifluoromethylphenyl, p-trifluoromethylphenyl, 2,3-bistrifluoromethylphenyl, 2,4-bistrifluoromethylphenyl, 2,5-bistrifluoromethylphenyl, 2,6-bistrifluoromethylphenyl, 3,4-bistrifluoromethylphenyl, 3,5-bistrifluoromethylphenyl, p-chlorophenyl, p-bromophenyl and p-iodophenyl.

Examples of C$_1$-C$_{30}$ condensed polycyclic aromatic groups are monovalent organic groups obtained by elimination of one hydrogen atom from pentalene, indene, naphthalene, azulene, heptalene, biphenylene, indacene, acenaphthylene, phenalene, phenanthrene, anthracene, fluoranthene, acephenanthrylene, aceanthrylene, triphenylene, pyrene, chrysene, naphthacene, picene, perylene, pentaphene, pentacene, tetraphenylene, hexaphene, hexacene, rubicene, coronene, trinaphthylene, heptaphene, heptacene, pyranthrene, ovalene and the like. In each of the foregoing groups, one or more hydrogen atom can be substituted with a fluorine atom or a C$_1$-C$_4$ alkyl or fluorine-containing alkyl group.

Examples of the monocyclic and polycyclic heterocyclic groups are those of 3 to 25 ring carbon atoms, such as pyridyl, furyl, thienyl, pyranyl, pyrrolyl, thianthrenyl, pyrazolyl, isothiazolyl, isoxazolyl, pyrazinyl, pyrimidinyl, pyridazinyl, tetrahydropyranyl, tetrahydrofuranyl, tetrahydrothiopyranyl, tetrahydrothiofuranyl and 3-tetrahydrothiophene-1,1-dioxide. One or more hydrogen atoms on the ring structure of the above heterocyclic group can each be independently substituted with an alkyl group, an alicyclic hydrocarbon group, an aryl group, or a heterocyclic group. Preferred are those having a monocyclic or polycyclic ether ring or lactone ring, exemplified by the following formulas (17-A) to (17-E):

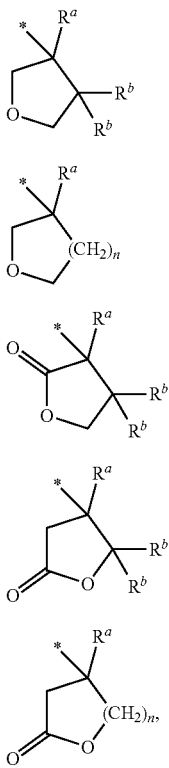

wherein $R^a$ and $R^b$ each independently represent a hydrogen atom or a $C_1$-$C_4$ alkyl group, and n represents an integer of 2 to 4.

Non-limiting examples of $W^1$ include the following formulas (18) to (23):

$$*-(CR^{13}R^{14})_m-C(=O)-O-(CR^{13}R^{14})_n-*; \quad (18)$$

$$*-(CR^{13}R^{14})_m-C(=O)-O-(CR^{13}R^{14})_n-B-(CR^{13}R^{14})_t-*; \quad (19)$$

$$*-(CR^{13}R^{14})_m-O-(CR^{13}R^{14})_n-* \quad (20)$$

$$*-(CR^{13}R^{14})_m-O-(CR^{13}R^{14})_n-B-(CR^{13}R^{14})_t-*; \quad (21)$$

$$*-(CR^{13}R^{14})_n-B-(CR^{13}R^{14})_t-C(=O)-O-(CR^{13}R^{14})_m-*; \text{ and} \quad (22)$$

$$*-(CR^{13}R^{14})_n-B-(CR^{13}R^{14})_t-O-(CR^{13}R^{14})_m-*. \quad (23)$$

wherein B represents a cyclic group selected from a divalent alicyclic hydrocarbon group, a divalent aromatic hydrocarbon group, or a divalent heterocyclic group; and l, m and n each independently represent an integer of 0 to 10. It is preferable that m is 0 and each of l and n is 0 or 1.

The linking group $W^2$, for linking V' to the main chain of the repeating unit in the negative resist resin, is the same as the linking group $W^1$ except $W^2$ does not include any divalent aromatic hydrocarbon group or aromatic heterocyclic group.

Non-limiting examples of $W^2$ include the following formulas (24) to (29):

$$*-(CR^{13}R^{14})_m-C(=O)-O-(CR^{13}R^{14})_n-*; \quad (24)$$

$$*-(CR^{13}R^{14})_m-C(=O)-O-(CR^{13}R^{14})_n-B'-(CR^{13}R^{14})_t-*; \quad (25)$$

$$*-(CR^{13}R^{14})_m-O-(CR^{13}R^{14})_n-* \quad (26)$$

$$*-(CR^{13}R^{14})_m-O-(CR^{13}R^{14})_n-B'-(CR^{13}R^{14})_t-*; \quad (27)$$

$$*-(CR^{13}R^{14})_n-B'-(CR^{13}R^{14})_t-C(=O)-O-(CR^{13}R^{14})_m-*; \text{ and} \quad (28)$$

$$*-(CR^{13}R^{14})_n-B'-(CR^{13}R^{14})_t-O-(CR^{13}R^{14})_m-*. \quad (29)$$

where B' represents a cyclic group selected from a divalent alicyclic group or a divalent heterocyclic group; and l, m and n each independently represent an integer of 0 to 10. It is preferable that m is 0 and each of l and n is 0 or 1.

The divalent alicyclic hydrocarbon group, constituting the main skeleton of the linking group $W^1$ and/or $W^2$, can be either monocyclic or polycyclic. More specifically, the divalent alicyclic hydrocarbon group can be any of those having a monocyclo, bicyclo, tricyclo, or tetracyclo structure of 3 or more carbon atoms, preferably 3 to 30 carbon atoms, more preferably 3 to 25 carbon atoms. The divalent alicyclic hydrocarbon group can have a substituent.

The divalent alicyclic hydrocarbon group, when it is monocyclic, preferably has 3 to 12 ring carbon atoms, more preferably 3 to 7 ring carbon atoms. Examples of the divalent monocyclic alicyclic hydrocarbon group are cyclopropylene, cyclobutylene, cyclopentylene, cyclohexylene, cycloheptylene, cyclooctylene, cyclodecanylene, cyclododecanylene and 4-tert-butylcyclohexylene. The alicyclic hydrocarbon group, when it is polycyclic, can have, for example, 7 to 15 ring carbon atoms. Examples of the divalent polycyclic alicyclic hydrocarbon group are adamantylene, noradamantylene, decalinylene (divalent hydrocarbon structure of decalin), tricyclodecanylene, tetracyclododecanylene, norbornylene (divalent hydrocarbon structure of norbornane), and cedrylene (divalent hydrocarbon structure of cedrol). The divalent alicyclic hydrocarbon group can be a spiro ring of preferably of 3 to 6 carbon atoms. One hydrogen atom or two or more hydrogen atoms on the linking group or the ring carbon(s) of the organic group can be each independently be substituted with a substituent such as $C_1$-$C_{30}$ alkyl group, substituted alkyl group, hydroxy group, alkoxyl group, carboxyl group, or alkoxycarbonyl group. The $C_1$-$C_{30}$ alkyl group is preferably a lower alkyl group, more preferably an alkyl group selected from the group consisting of methyl, ethyl, propyl and isopropyl. As the substituent of the substituted alkyl group, there can be used a hydroxy group, a halogen atom, an alkoxyl group and the like. The alkoxyl group is, for example, of 1 to 4 carbon atoms, as exemplified by methoxy, ethoxy, propoxy and butoxy. The alkoxycarbonyl group is, for example, exemplified by methoxycarbonyl, ethoxycarbonyl and isopropoxycarbonyl.

The divalent aromatic hydrocarbon group, when constituting the main skeleton of the linking group $W^1$, can be in the form of a monocyclic or condensed polycyclic aromatic ring structure of 1 to 30 carbon atoms. The aromatic hydrocarbon group, when it is monocyclic, preferably has 3 to 12 ring carbon atoms, more preferably 3 to 6 ring carbon atoms. Examples of the divalent monocyclic aromatic hydrocarbon group are divalent groups obtained by elimination of two hydrogen atoms from benzene, biphenyl, terphenyl, toluene, phenol, anisole, mesitylene, cumene, 2,3-xylylene, 2,4-xylene, 2,5-xylene, 2,6-xylene, 3,4-xylene, 3,5-xylene, fluorobenzene, trifluoromethylbenzene, o-bistrifluoromethylbenzene, m-bistrifluoromethylbenzene, p-bistrifluoromethylbenzene, chlorobenzene, bromobenzene, iodobenzene, and the like.

The divalent condensed polycyclic aromatic group can be substituted or unsubstituted and preferably has 1 to 30 carbon atoms. Examples of the divalent condensed polycyclic aromatic group are divalent organic groups obtained by elimination of two hydrogen atoms from pentalene, indene, naphthalene, azulene, heptalene, biphenylene, indacene, acenaphthylene, fluorene, phenalene, phenanthrene, anthracene, fluoranthene, acephenanthrylene, aceanthrylene, triphenylene, pyrene, chrysene, naphthacene, picene, perylene, pentaphene, pentacene, tetraphenylene, hexaphene, hexacene, rubicene, coronene, trinaphthylene, heptaphene, heptacene, pyranthrene, ovalene, and the like. One hydrogen atom or two or more hydrogen atoms of the above divalent organic group can each be independently substituted with a fluorine atom or a $C_1$-$C_4$ alkyl group or fluorine-containing alkyl group.

The divalent heterocyclic group, constituting the main skeleton of the linking group $W^1$, can be in the form of a monocyclic or polycyclic ring structure of 3 to 25 ring carbon atoms. The ring structure can be aromatic or non-aromatic. Examples of the divalent monocyclic or polycyclic heterocyclic group are divalent organic groups obtained by elimination of two hydrogen atoms from pyridine, furan, thienine, pyranine, pyrroline, thianthrene, pyrazon, isothiazone, isooxazone, pyrazine, pyrimidine, pyridazine, tetrahydropyranine, tetrahydrofuranine, tetrahydrothiopyranine, tetrahydrothiofuranine and the like. One hydrogen atom or two or more hydrogen atoms on the ring atom of the above divalent organic group can each be independently substituted with an alkyl group (preferably, a lower alkyl group), an alicyclic hydrocarbon group, an aryl group or a heterocyclic group. Among others, preferred are monocyclic or polycyclic ether rings as exemplified below.

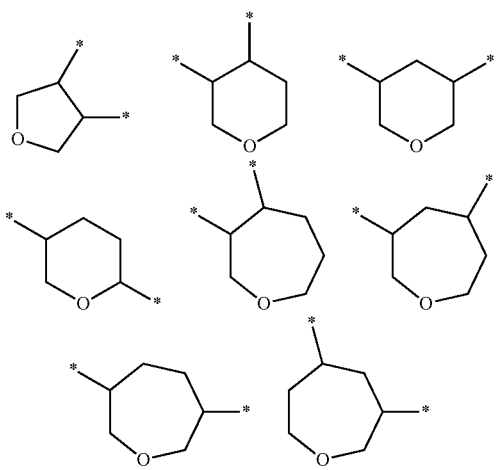

Each of the divalent linking groups $W^1$ and $W^2$ can be formed by combination of any of the divalent groups explained above by the general formulas or specifically exemplified above, with limitations on $W^2$ as stated further above.

Specific examples of the linking group $W^1$ are as follows:

\*—\* (single bond);
\*—$CH_2$—\*;
\*—$CH_2$—$CH_2$—\*;
\*—$CH_2$—B—\*;
\*—B—$CH_2$—\*;
\*—$C_6H_4$—\*;
\*—C(=O)—O—$CH_2$—\*;
\*—C(=O)—O—$CH_2$—$CH_2$—\*;
\*—C(=O)—O—B—\*;
\*—$CH_2$—C(=O)—O—$CH_2$—\*;
\*—O—$CH_2$—\*;
\*—O—$CH_2$—$CH_2$—\*;
\*—O—B—\*;
\*—$CH_2$—O—$CH_2$—\*;
\*—C(=O)—O—$(C(R^{13})(R^{14}))_2$—\*; and
\*—$C_6H_4$—O—$(C(R^{13})(R^{14}))_2$—\*, wherein B represents a cyclic group selected from a divalent alicyclic hydrocarbon group, a divalent aromatic hydrocarbon group or a divalent heterocyclic group, $R^{13}$ and $R^{14}$ are each independently a hydrogen atom, a fluorine atom, an alkyl group, a substituted alkyl group or an alicyclic hydrocarbon group. One or more hydrogen atoms of the above linking group $W^1$ can be substituted with a fluorine atom. Particularly preferred are \*—C(=O)—O—$CH_2$—\*, \*—$C_6H_4$—\* and \*—C(=O)—O—$(C(R^{13})(R^{14}))_2$—\* wherein $R^{13}$ and $R^{14}$ are each independently a hydrogen atom, a fluorine atom, a lower alkyl group or a fluorine-containing lower alkyl group.

Specific examples of the linking group $W^2$ are as follows:

\*—\* (single bond);
\*—$CH_2$—\*;
\*—$CH_2$—$CH_2$—\*;
\*—$CH_2$—B'—\*;
\*—B'—\*
\*—B'—$CH_2$—\*;
\*—C(=O)—O—$CH_2$—\*;
\*—C(=O)—O—$CH_2$—$CH_2$—\*;
\*—C(=O)—O—B'—\*;
\*—$CH_2$—C(=O)—O—$CH_2$—\*;
\*—O—$CH_2$—\*;
\*—O—$CH_2$—$CH_2$—\*;
\*—O—B'—\*;
\*—$CH_2$—O—$CH_2$—\*; and
\*—C(=O)—O—$(C(R^{13})(R^{14}))_2$—\*, wherein B' represents a cyclic group selected from a divalent alicyclic group or a divalent heterocyclic group, $R^{13}$ and $R^{14}$ are each independently a hydrogen atom, a fluorine atom, an alkyl group, a substituted alkyl group, or an alicyclic hydrocarbon group. One or more hydrogen atoms of the above linking group $W^2$ can be substituted with a fluorine atom. Particularly preferred are \*—C(=O)—O—\*, \*—C(=O)—O—$CH_2$—\*, \*—C(=O)—O—B'—\*, and \*—C(=O)—O—$(C(R^{13})(R^{14}))_2$—\* wherein $R^{13}$ and $R^{14}$ are each independently a hydrogen atom, a fluorine atom, a lower alkyl group, or a fluorine-containing lower alkyl group.

Other second repeating units comprising an acid-labile group have a structure according to formula (30):

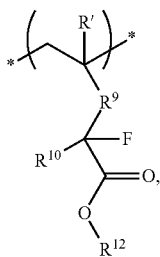
(30)

wherein

R' is a monovalent radical selected from the group consisting of H, F, $C_1$-$C_3$ alkyl groups, fluorine-containing $C_1$-$C_3$ alkyl groups, and cyano, $R^9$ represents a divalent linking group, $R^{10}$ represents a hydrogen atom, a fluorine atom, or a fluorine-containing alkyl group, and $R^{12}$ is an acid-labile group.

As *—$R^9$—$C(R^{10})(F)$—* corresponds to $W^1$, the above definition of the linking group $W^1$ can be applied to the moiety *—$R^9$—$C(R^{10})(F)$—*.

The acid-labile group $R^{12}$ of formula (30) can have a structure in accordance with any of formulas (31) to (35):

$$R^{X1}-O-C(=O)-* \quad (31),$$

wherein $R^{X1}$ represents a $C_1$-$C_4$ alkyl group that can have a substituent, a $C_3$-$C_{30}$ alicyclic hydrocarbon group that can have a substituent, or a $C_6$-$C_{14}$ aryl group that can have a substituent;

$$R^{X1}-O-C(H)(R^{X2})-* \quad (32),$$

wherein $R^{X1}$ has the same definition as in the general formula (31), and $R^{X2}$ represents a hydrogen atom, a $C_1$-$C_4$ alkyl group that can have a substituent, a $C_3$-$C_{30}$ alicyclic hydrocarbon group that can have a substituent, a $C_1$-$C_6$ alkoxy group that can have a substituent, a $C_2$-$C_4$ alkenyl group that can have a substituent, a $C_6$-$C_{14}$ aryl group that can have a substituent, or a $C_7$-$C_{20}$ aralkyl group that can have a substituent;

$$*-C(R^{X3})(R^{X4})(R^{X5}) \quad (33),$$

wherein $R^{X3}$, $R^{X4}$ and $R^{X5}$ can be the same or different and each represents a $C_1$-$C_4$ alkyl group that can have a substituent, a $C_3$-$C_{30}$ alicyclic hydrocarbon group that can have a substituent, a $C_2$-$C_4$ alkenyl group that can have a substituent, a $C_6$-$C_{14}$ aryl group that can have a substituent, or a $C_7$-$C_{20}$ aralkyl group that can have a substituent; and two of $R^{X3}$, $R^{X4}$ and $R^{X5}$ can be bonded together to form a ring;

$$*-Si(R^{X3})(R^{X4})(R^{X5}) \quad (34),$$

wherein $R^{X3}$, $R^{X4}$ and $R^{X5}$ have the same definitions as in the general formula (33); and $$R^{X1}-C(=O)-* \quad (35),$$

wherein $R^{X1}$ has the same definition as in the general formula (31).

The monovalent organic groups $R^{X1}$, $R^{X2}$, $R^{X3}$, $R^{X4}$ and $R^{X5}$ in the above formulas (31) to (35) are described below in more detail. It is preferable to use the acid-labile group of the general formula (31), (32) and/or (33), which are capable of chemical amplification, in a resist composition used to form patterns by exposure to high energy radiation.

More specifically, $R^{X1}$ represents an alkyl group, an alicyclic hydrocarbon group or an aryl group; $R^{X2}$ represents a hydrogen atom, an alkyl group, an alicyclic hydrocarbon group, an alkenyl group, an aralkyl group, an alkoxy group or an aryl group; $R^{X3}$, $R^{X4}$ and $R^{X5}$ can be the same or different and each represents an alkyl group, an alicyclic hydrocarbon group, an alkenyl group, an aralkyl group or an aryl group; and two of two of $R^{X3}$, $R^{X4}$ and $R^{X5}$ can be bonded together to form a ring.

Preferred examples of the alkyl groups are those of 1 to 4 carbon atoms, such as methyl, ethyl, propyl, isopropyl, n-butyl, sec-butyl and tert-butyl. Preferred examples of the alicyclic hydrocarbon group are those of 3 to 30 carbon atoms, such as cyclopropyl, cyclopentyl, cyclohexyl, adamantyl, norbornyl, bornyl, tricyclodecanyl, dicyclopentenyl, epoxynorbornan, menthyl, isomenthyl, neomenthyl, tetracyclododecanyl and steroid residue. Preferred examples of the alkenyl group are those of 2 to 4 carbon atoms, such as vinyl, propenyl, allyl and butenyl. Preferred examples of the aryl group are those of 6 to 14 carbon atoms, such as phenyl, xylyl, toluoyl, cumenyl, naphthyl and anthracenyl. These groups can have substituents. Preferred examples of the aralkyl group are those of 7 to 20 carbon atoms, such as benzyl, phenethyl and cumyl, each of which can have a substituent.

As the substituents of the alkyl group, the alicyclic hydrocarbon group, the alkenyl group, the aryl group and the aralkyl group, there can be used: a hydroxy group; a halogen atom (fluorine, chlorine, bromine, iodine); a nitro group; a cyano group; any of the above alkyl and alicyclic hydrocarbon groups; an alkoxy group such as methoxy, ethoxy, hydroxyethoxy, propoxy, hydroxypropoxy, n-butoxy, isobutoxy, sec-butoxy or tert-butoxy; an alkoxycarbonyl group such as methoxycarbonyl or ethoxycarbonyl; an aralkyl group such as benzyl, phenethyl or cumyl; an aralkyloxy group; an acyl group such as formyl, acetyl, butyryl, benzoyl, cinnamyl or valeryl; an acyloxy group such as butyryloxy; any of the above alkenyl groups; an alkenyloxy group such as vinyloxy, propenyloxy, allyloxy or butenyloxy; any of the above aryl groups, an aryloxy group such as phenoxy; and an aryloxycarbonyl group such as benzoyloxy.

There can also be used lactone groups of the following formulas (36) to (44).

(36)

(37)

(38)

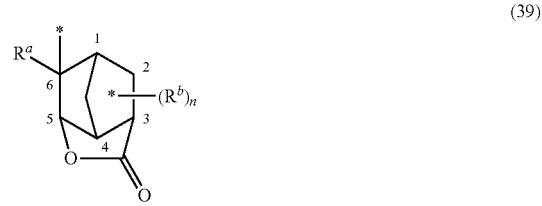
(39)

-continued

(40)
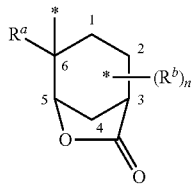

(41)
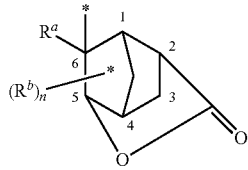

(42)
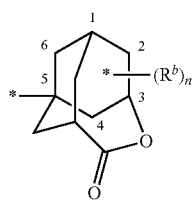

(43)
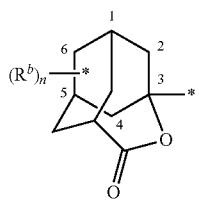

(44)
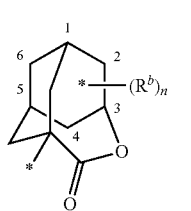

In the formulas (36) to (44), $R^a$ represents a $C_1$-$C_4$ alkyl or perfluoroalkyl group; $R^b$ each independently represent a hydrogen atom, a $C_1$-$C_4$ alkyl or perfluoroalkyl group, a hydroxy group, a carboxylic acid group, an alkyloxycarbonyl group, an alkoxy group or the like; and n represents an integer of 1 to 4. Each $R^b$ can be linked to any one of the numbered carbons 1 to 6 that does not already have 4 substituents.

More specific acid-labile groups are exemplified as follows.

Specific examples of the alkoxycarbonyl group represented by the general formula (31): $R^{X1}$—O—C(=O)—* are tert-butoxycarbonyl (t-Boc), tert-amyloxycarbonyl, methoxycarbonyl, ethoxycarbonyl, i-propoxycarbonyl, cyclohexyloxycarbonyl, isobornyloxycarbonyl and adamantanoxycarbonyl.

Specific examples of the acetal group represented by the general formula (32): $R^{X1}$—O—CHR$^{X2}$—* are methoxymethyl, ethoxymethyl, 1-ethoxyethyl, 1-butoxyethyl, 1-isobutoxyethyl, 1-cyclohexyloxyethyl, 1-benzyloxyethyl, 1-phenethyloxyethyl, 1-ethoxypropyl, 1-benzyloxypropyl, 1-phenethyloxypropyl, 1-ethoxybutyl, 1-cyclohexyoxyethyl, 1-ethoxyisobutyl, 1-methoxyethoxymethyl, tetrahydropyranyl and tetrahydrofuranyl. There can also be used acetal groups obtained by addition of vinyl ethers to a hydroxy group.

Specific examples of the tertiary hydrocarbon group represented by the general formula (33): *—C(R$^{X3}$)(R$^{X4}$)(R$^{X5}$) are tert-butyl, tert-amyl, 1,1-dimethylpropyl, 1-ethyl-1-methylpropyl, 1,1-dimethylbutyl, 1-ethyl-1-methylbutyl, 1,1-diethylpropyl, 1,1-dimethyl-1-phenylmethyl, 1-methyl-1-ethyl-1-phenylmethyl, 1,1-diethyl-1-phenylmethyl, 1-methylcyclohexyl, 1-ethylcyclohexyl, 1-methylcyclopentyl, 1-ethylcyclopentyl, 1-isobornyl, 1-methyladamantyl, 1-ethyladamantyl, 1-isopropyladamantyl, 1-isopropylnorbornyl and 1-isopropyl-(4-methylcyclohexyl).

Alicyclic hydrocarbon groups or alicyclic hydrocarbon-containing acid-labile group are exemplified by the structures of Scheme 10.

Scheme 10

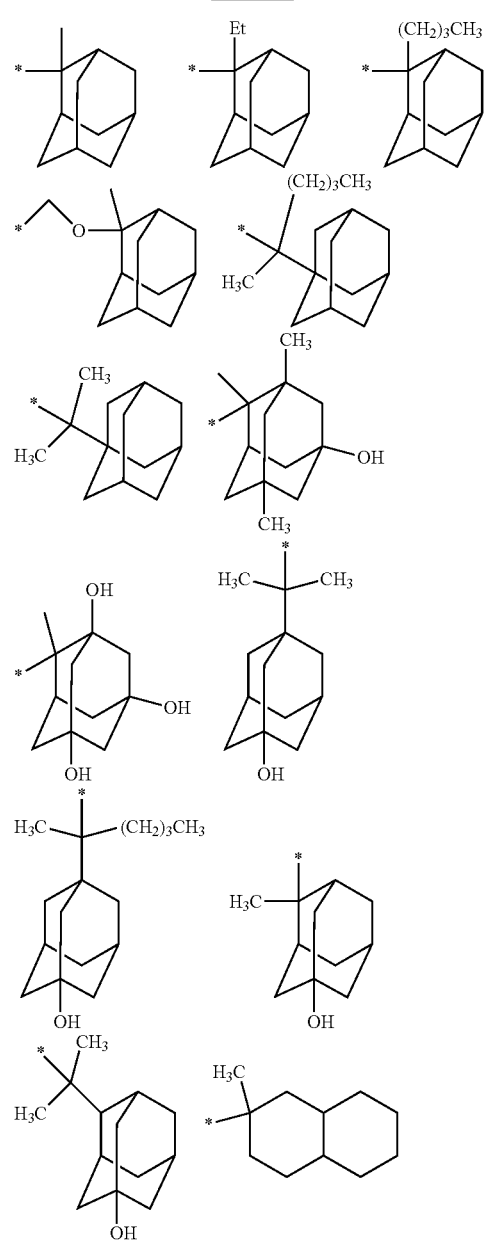

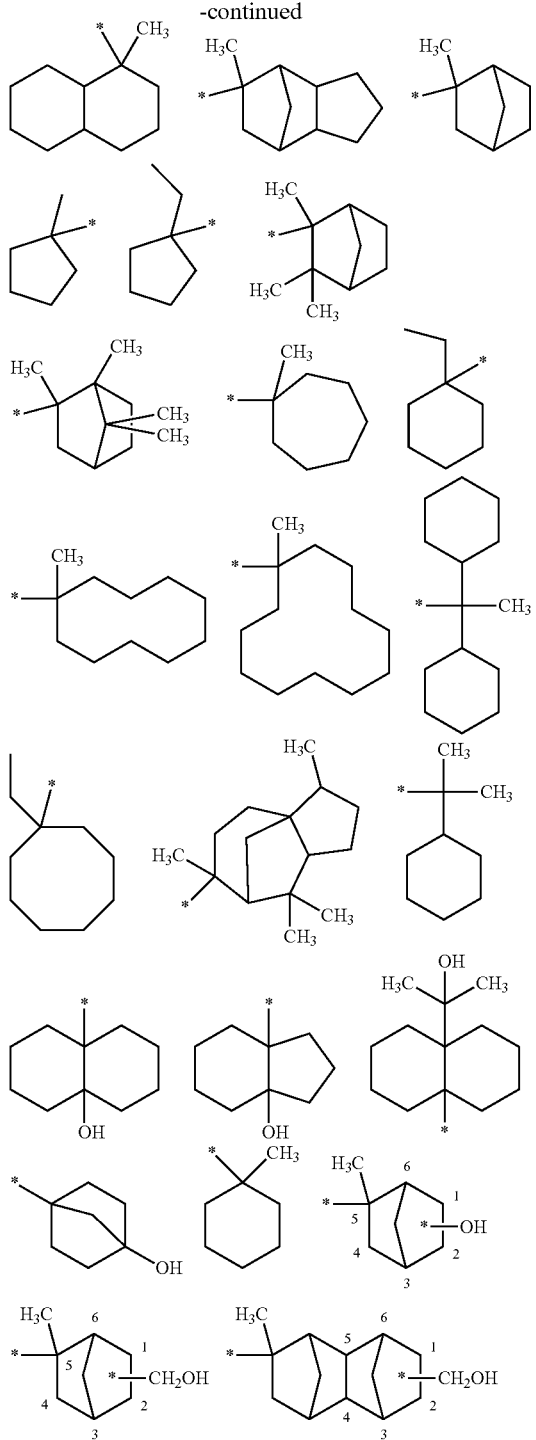

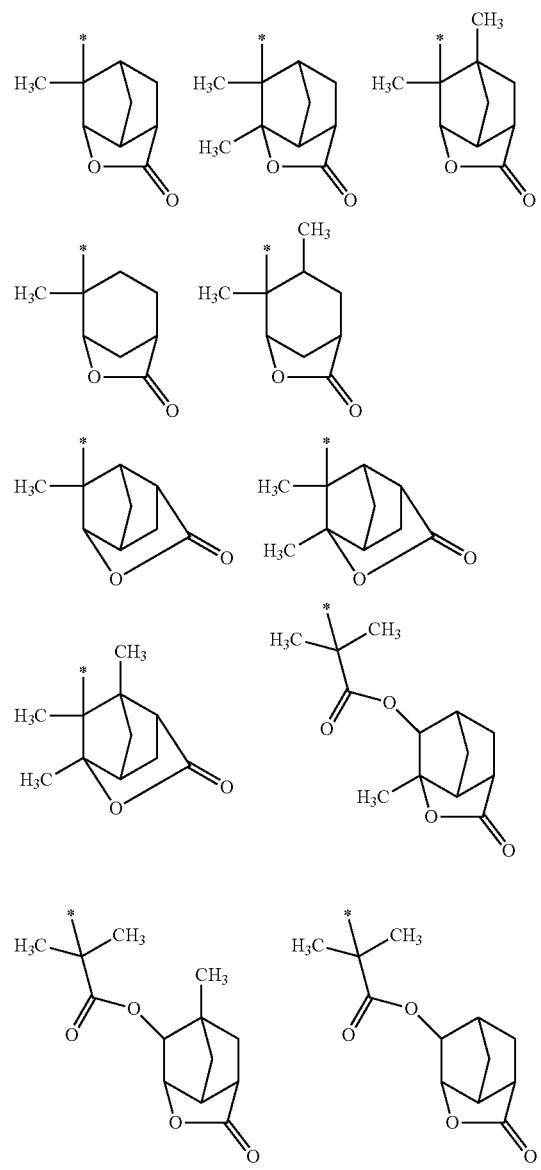

Scheme 11 lyl, tert-butyldimethylsilyl, methyl-di-tert-butylsilyl, tri-tert-butylsilyl, phenyldimethylsilyl, methyldiphenylsilyl and triphenylsilyl.

Specific examples of the acyl group represented by the general formula (35): $R^{X1}$—C(=O)—* are acetyl, propionyl, butyryl, heptanoyl, hexanoyl, valeryl, pivaloyl, isovaleryl, lauryloyl, myristoyl, palmitoyl, stearoyl, oxalyl, malonyl, succinyl, glutaryl, adipoyl, piperoyl, suberoyl, azelaoyl, sebacoyl, acryloyl, propioyl, methacryloyl, crotonoyl, oleoyl, maleoyl, fumaroyl, mesaconoyl, camphoroyl, benzoyl, phthaloyl, isophtaloyl, terephthaloyl, naphthoyl, toluoyl, hydroatropoyl, atropoyl, cinnamoyl, furoyl, thenoyl, nicotinoyl and isonicotinoyl. There can also be used those obtained by substitution of a part or all of hydrogen atoms of the above acid-labile groups with a fluorine atom.

Further, the lactone-containing acid-labile protecting group can be exemplified by the groups of Scheme 11.

In Scheme 10, the methyl (CH₃) groups can independently be replaced by an ethyl group; and one or more of the ring carbons can have a substituent group as mentioned above. The bonds to OH and CH₂OH that overlap a ring bond can be linked to any one of the numbered carbons 1 to 6 that is not already linked to 4 substituents.

Specific examples of the silyl group represented by the general formula (34): *—Si($R^{X3}$)($R^{X4}$)($R^{X5}$) are trimethylsilyl, ethyldimethylsilyl, methyldiethylsilyl, triethylsilyl, propyldimethylsilyl, methyl-di-1-propylsilyl, tri-1-propylsi- -continued
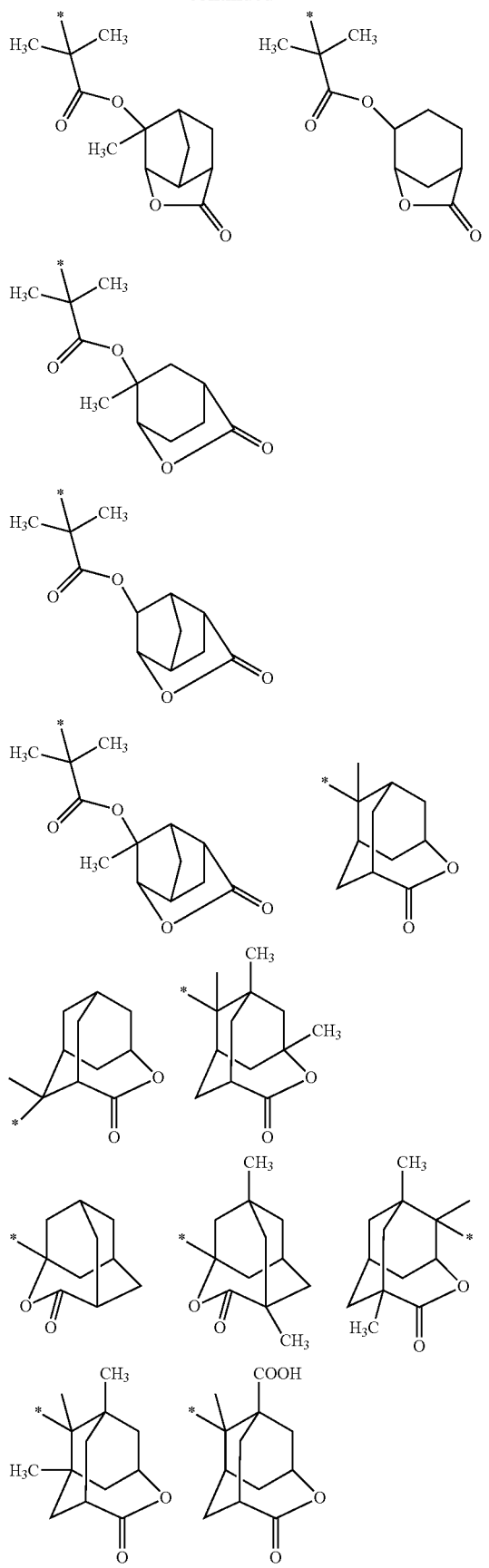
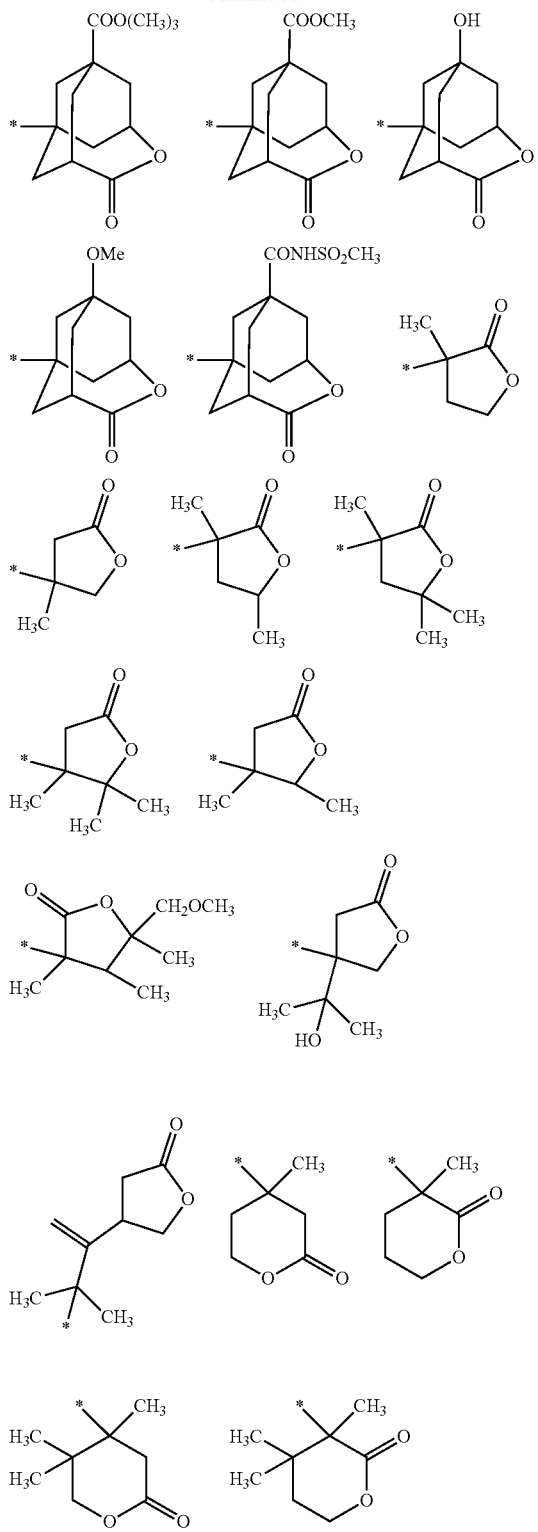
In the structures of Scheme 11, each methyl (*—CH₃) group can independently be replaced by an ethyl group.
Other acid labile protecting groups include acetal and ketal esters of carboxylic acids. In the following groups, the atomic center linked to an asterisk is covalently linked to the ester oxygen of the carboxylic ester group.

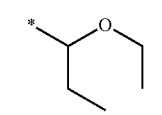

(e.g., of acetal ester)

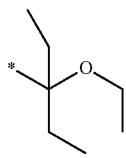

(e.g., of ketal ester)

Most preferred acid-labile groups include a tertiary alkyl group such as tert-butyl or tert-amyl, an alkoxyethyl group such as 1-ethoxyethyl, 1-butoxyethyl, 1-isobutoxyethyl or 1-cyclohexyloxyethyl, an alkoxymethyl group such as methoxymethyl or ethoxymethyl, an acid-labile group containing an alicyclic hydrocarbon such as adamantyl or isobornyl, or a lactone-containing acid-labile group as exemplified above.

Acid Labile Monomers

Non-limiting examples of polymerizable monomers for forming the second repeating units containing an acid labile group include those shown in Scheme 12. Each of the acid labile monomers can be used singularly or in combination with other acid labile monomers.

Scheme 12

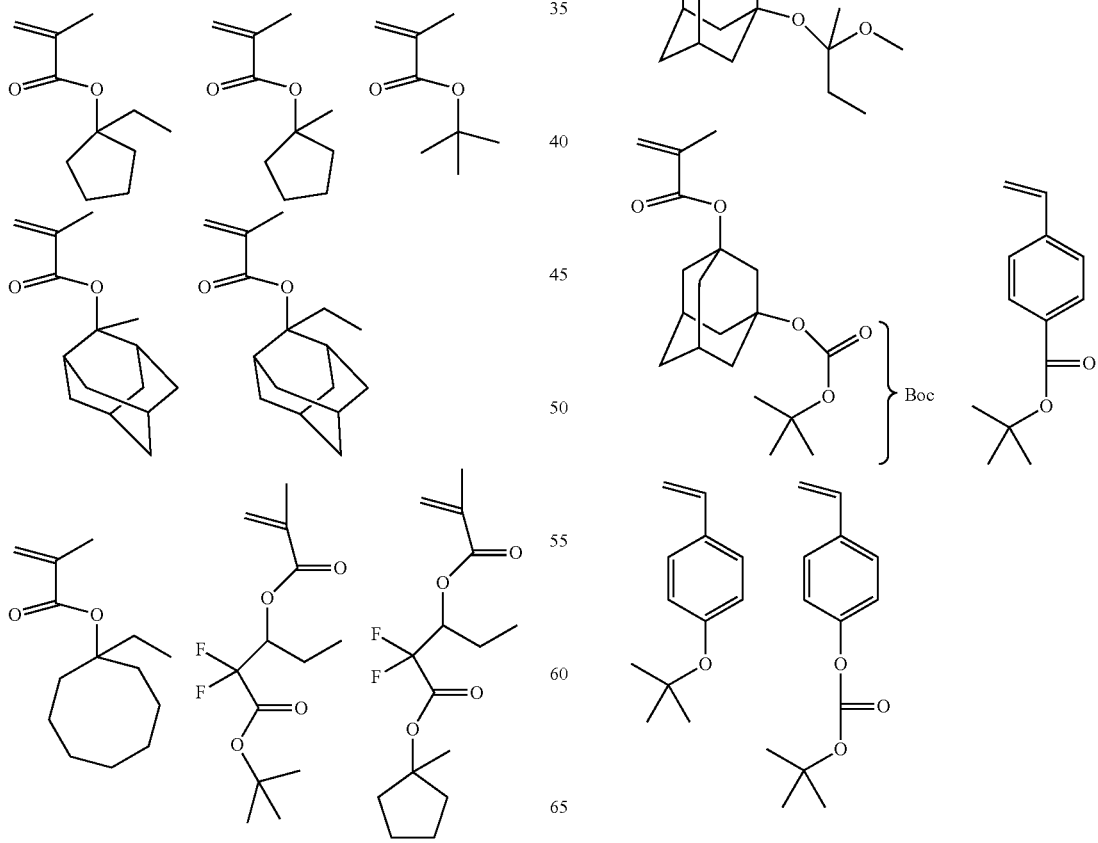

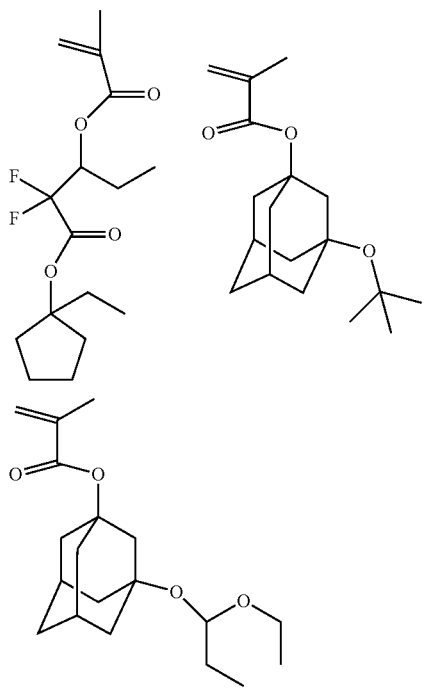

Crosslinking Monomers

Non-limiting examples of nucleophilic crosslinking monomers include the following.

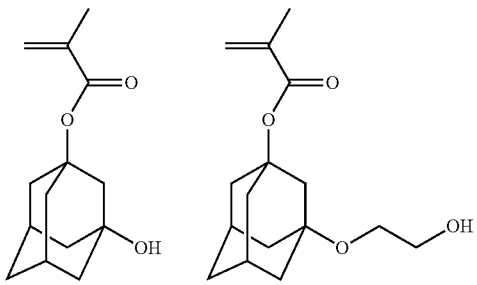 [SMILES: C=C(C)C(=O)OC12CC3CC(CC(O)(C3)C1)C2 ; C=C(C)C(=O)OC12CC3CC(CC(OCCO)(C3)C1)C2]

The PAG polymer can comprise an electrophilic crosslinking repeat unit (e.g., repeat unit derived from vinyl polymerization of glycidyl methacrylate), which contains a pendent electrophilic group (e.g., epoxide, active methylene such as alkyl halide, or the like), which is capable of undergoing a crosslinking reaction with a nucleophile.

Auxiliary Repeating Unit

The PAG polymer can be produced with the use of one or more vinyl polymerizable auxiliary monomers as co-monomers. There is no particular limitation on the auxiliary monomer. Non-limiting exemplary auxiliary monomers include olefins, fluorine-containing olefins, acrylic esters, methacrylic esters, fluorine-containing acrylic esters, fluorine-containing methacrylic esters, norbornene compounds, fluorine-containing norbornene compounds, styrenic compounds, fluorine-containing styrenic compounds, vinyl ethers and fluorine-containing vinyl ethers. Acrylic esters, methacrylic esters, fluorine-containing acrylic esters, fluorine-containing methacrylic esters, norbornene compounds, fluorine-containing norbornene compounds, styrenic compounds, vinyl ethers and fluorine-containing vinyl ethers are preferred classes of auxiliary monomers. In an embodiment, the auxiliary monomer and the auxiliary repeating unit of the PAG polymer comprise a hexafluoroalcohol (HFA) group (*—C(CF$_3$)$_2$OH).

Specific examples of the olefins are ethylene and propylene. Specific examples of the fluoroolefins are vinyl fluoride, vinylidene fluoride, trifluoroethylene, chlorotrifluoroethylene, tetrafluoroethylene, hexafluoroethylene and hexafluoroisobutene.

No particular limitation is placed on the ester side chain structure of the acrylic ester and/or methacrylic ester. The term "acrylic and/or methacrylic" is abbreviated herein as "(meth)acrylic". The term "acrylate and/or methacrylate" is abbreviated herein as "(meth)acrylate". Specific examples of (meth)acrylic esters are (meth)acrylic ester compounds having alkyl ester groups (e.g., methyl (meth)acrylate, ethyl (meth)acrylate, n-propyl (meth)acrylate, isopropyl (meth)acrylate, n-butyl (meth)acrylate, isobutyl (meth)acrylate, n-hexyl (meth)acrylate, n-octyl (meth)acrylate, 2-ethylhexyl (meth)acrylate, lauryl (meth)acrylate, 2-hydroxyethyl (meth)acrylate, and 2-hydroxypropyl (meth)acrylate); (meth)acrylates containing an ethylene glycol group, propylene glycol group, or tetramethylene glycol group; unsaturated amides (e.g., acrylamide, methacrylamide, N-methylol acrylamide, N-methylol methacrylamide, and diacetone acrylamide); acrylonitrile; methacrylonitrile; alkoxysilane-containing vinyl silane; alkoxysilane-containing (meth)acrylic ester; t-butyl (meth)acrylate; 3-oxocyclohexyl (meth)acrylate; adamantyl (meth)acrylate; alkyladamantyl (meth)acrylate; cyclohexyl (meth)acrylate; tricyclodecanyl (meth)acrylate; (meth)acrylates having a ring structure such as a lactone ring and/or norbornene ring; acrylic acid; and methacrylic acid.

There can also be used an acrylate compound obtained by bonding a cyano group to the a-position of the above acrylate or analog thereof.

There can also be used maleic acid, fumaric acid and maleic anhydride.

There can also be used (meth)acrylate esters of alicyclic compounds having alcohol functionalities (e.g., hydroxyadamantyl methacrylate)

Examples of fluorine-containing acrylic esters are acrylic esters having a fluorine atom or a fluorine-containing group in the alpha-position of the acrylic acid group. For instance, the monomer having a fluoroalkyl group in its alpha-position can suitably be exemplified by a monomer in which a trifluoromethyl group, a trifluoroethyl group, or a nonafluoro-n-butyl group has been added to the alpha-position of the above non-fluorinated acrylic ester.

On the other hand, there can be used (meth)acrylic esters in which a fluorinated alkyl group (e.g., a perfluoroalkyl group or a fluoroalkyl group) is bonded to the ester moiety or in which a cyclic structure coexists with a fluorine atom in the ester moiety. The cyclic structure can be a fluorine-containing benzene ring, a fluorine-containing cyclopentane ring, a fluorine-containing cyclohexane ring, a fluorine-containing cycloheptane ring, or the like having a fluorine atom or a trifluoromethyl group as a substituent. A (meth)acrylic ester in which the ester moiety is a fluorine-containing t-butyl ester group can also be used. Typical examples of such monomer units include 2,2,2-trifluoroethyl acrylate, 2,2,3,3-tetrafluoropropyl acrylate, 1,1,1,3,3,3-hexafluoroisopropyl acrylate, heptafluoroisopropyl acrylate, 1,1-dihydroheptafluoro-n-butyl acrylate, 1,1,5-trihydrooctafluoro-n-pentyl acrylate, 1,1,2,2-tetrahydrotridecafluoro-n-octyl acrylate, 1,1,2,2-tetrahydroheptadecafluoro-n-decyl acrylate, 2,2,2-trifluoroethyl methacrylate, 2,2,3,3-tetrafluoropropyl methacrylate, 1,1,1,3,3,3-hexafluoroisopropyl methacrylate, heptafluoroisopropyl methacrylate, 1,1-dihydroheptafluoro-n-butyl methacrylate, 1,1,5-trihydrooctafluoro-n-pentyl methacrylate, 1,1,2,2-tetrahydrotridecafluoro-n-octyl methacrylate, 1,1,2,2-tetrahydroheptadecafluoro-n-decyl methacrylate, perfluorocyclohexylmethyl acrylate, and perfluorocyclohexylmethyl methacrylate.

Norbornene monomers and fluorine-containing norbornene monomers having a mononuclear or multinuclear structure can be used without particular limitation. Examples of norbornene compounds are those each formed by Diels-Alder addition reaction of an unsaturated compound such as an allyl alcohol, a fluorine-containing allyl alcohol, an acrylic acid, an alpha-fluoroacrylic acid, a methacrylic acid and any of the acrylic esters, methacrylic esters, fluorine-containing acrylic esters and fluorine-containing methacrylic esters described herein with cyclopentadiene or cyclohexadiene.

The styrenic compounds, fluorine-containing styrenic compounds, vinyl ethers, fluorine-containing vinyl ethers, allyl ethers, vinyl esters, vinyl silanes, and the like can also be used as auxiliary monomers. Examples of the styrenic compounds and fluorine-containing styrenic compounds include styrene, fluorinated styrene, hydroxystyrene, hexafluoroacetone-added styrenic compounds, trifluoromethyl-substituted styrene, hydroxystyrene, and monomers obtained by bonding a halogen atom, an alkyl group, or a fluoroalkyl group to the alpha-position of the above styrene or fluorine-containing styrenic compounds. Examples of the vinyl ethers and fluorine-containing vinyl ethers include i) alkyl vinyl ethers having an alkyl group (e.g., methyl, ethyl) or a hydroxyalkyl group (e.g., hydroxyethyl, hydroxybutyl) in which a part or all of hydrogen atoms can be substituted with fluorine and ii) cyclic vinyl ethers (e.g., cyclohexyl vinyl ether) including cyclic vinyl ethers containing a hydrogen and/or a carbonyl bond in their cyclic structures, in which a part or all of hydrogen atoms can be substituted with fluorine. The allyl ethers, vinyl esters and vinyl silane can be used without particular limitation.

One preferred example of the auxiliary repeating unit in the PAG polymer or fluorine-containing N-sulfonyloxyimide resin is a repeating unit of the following general formula (45).

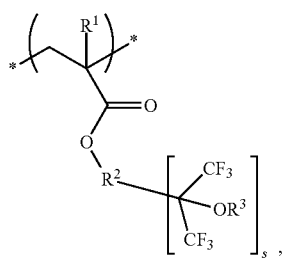
(45)

wherein s represents an integer of 1 to 8, $R^1$ is a monovalent radical selected from the group consisting of hydrogen, halogen, $C_1$-$C_3$ alkyl, fluorine-containing $C_1$-$C_3$ alkyl group, and cyano, $R^2$ represents a substituted or unsubstituted aliphatic hydrocarbon group, a substituted or unsubstituted aromatic group, or a divalent organic group formed by combination of a plurality thereof, and $R^3$ represents a hydrogen atom, a substituted or unsubstituted $C_1$-$C_{25}$ aliphatic hydrocarbon group or a substituted or unsubstituted $C_1$-$C_{25}$ aromatic hydrocarbon group.

Optionally, any number of hydrogen atoms of $R^2$ can be substituted with a fluorine atom. $R^2$ can contain an ether bond and/or a carbonyl group.

Examples of the halogen atom as $R^1$ are fluorine, chlorine and bromine. Examples of the $C_1$-$C_3$ alkyl group as $R^1$ are methyl, ethyl, propyl and isopropyl. Examples of the $C_1$-$C_3$ fluorine-containing alkyl group as $R^1$ are those obtained by substitution of a part or all of hydrogen atoms of the above alkyl groups with a fluorine atom, such as trifluoromethyl (*—$CF_3$), trifluoroethyl (*—$CH_2CF_3$), 1,1,1,3,3,3-hexafluoroisopropyl and heptafluoroisopropyl. Preferred $R^1$ groups include hydrogen, fluorine, methyl and trifluoromethyl.

Any number of hydrogen atoms of $R^2$ can be substituted with a fluorine atom. The divalent aliphatic hydrocarbon group of $R^2$ can be straight, branched or cyclic. Examples of $R^2$ include straight chain and branched aliphatic hydrocarbon groups such as methylene, ethylene, isopropylene and t-butylene; cyclic aliphatic hydrocarbon groups such as cyclobutylene, cyclohexylene, divalent norbornane, and divalent adamantane; aromatic groups such as phenylene; divalent groups obtained by substitution of hydrogen atoms of the above groups with any substituent; and divalent groups obtained by replacement of carbon atoms of the above groups by an ether bond or a carbonyl group. These groups can be used without particular limitation.

More specific auxiliary repeating units include repeating units of formula (46):

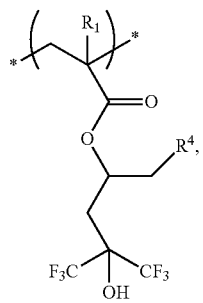
(46)

wherein $R^1$ has the same definition as in the general formula (45), and $R^4$ represents a hydrogen atom or a $C_1$-$C_6$ alkyl or fluorine-containing alkyl group.

Examples of the alkyl or fluorine-containing alkyl group as $R^4$ are methyl, ethyl, n-propyl, isopropyl, n-butyl, sec-butyl, tert-butyl, cyclopentyl, cyclohexyl, fluoromethyl, difluoromethyl, trifluoromethyl and perfluoroethyl.

Other more specific auxiliary repeating units are repeating units of formulas (47):

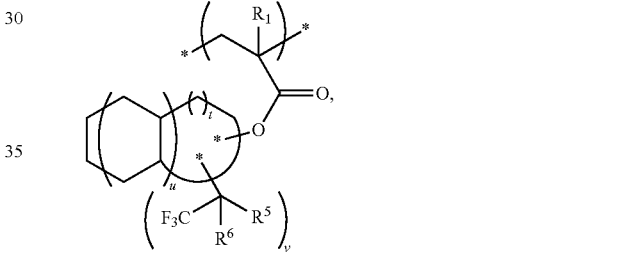
(47)

wherein u represents an integer of 0 to 2, each of t and v independently represents an integer of 1 to 8, wherein v≤t+2, $R^1$ has the same definition as in the general formula (45), $R^5$ represents a methyl group or a trifluoromethyl group, and $R^6$ represents a hydrogen atom, hydroxyl group, a substituted or unsubstituted $C_1$-$C_{25}$ aliphatic hydrocarbon group or a substituted or unsubstituted $C_1$-$C_{25}$ aromatic hydrocarbon group, a part of which can contain a fluorine atom, an oxygen atom (ether bond) or a carbonyl group.

In the case where there are a plurality of $R^5$ and $R^6$ groups and v is an integer of 2 or greater, $R^5$ and $R^6$ can be the same or different. A particularly preferred $R^6$ is hydrogen.

Examples of the substituted or unsubstituted $C_1$-$C_{25}$ aliphatic hydrocarbon group or substituted or unsubstituted $C_1$-$C_{25}$ aromatic hydrocarbon group as $R^6$ include methyl, ethyl, propyl, isopropyl, cyclopropyl, n-propyl, sec-butyl, tert-butyl, n-pentyl, cyclopentyl, sec-pentyl, neopentyl, hexyl, cyclohexyl, ethylhexyl, norbornel, adamantyl, vinyl, aryl, butenyl, pentenyl, ethynyl, phenyl, benzyl and 4-methoxybenzyl, in each of which a part or all of hydrogen atoms can be substituted with a fluorine atom. As the oxygen-containing hydrocarbon group, an alkoxycarbonyl group, an acetal group or an acyl group can be used. Examples of the alkoxycarbonyl group are tert-butoxycarbonyl, tert-amyloxycarbonyl, methoxycarbonyl, ethoxycarbonyl and i-propoxycarbonyl. Examples of the acetal group are: linear ethers such as methoxymethyl, methoxyethoxymethyl, ethoxyethyl, butoxyethyl, cyclohexyloxyethyl, benzyloxyethyl, phenethyloxyethyl, ethoxypropyl, benzyloxypropyl, phenethyloxypropyl, ethoxybutyl and ethoxyisobutyl; and cyclic ethers such as tetrahydrofuranyl and tetrahydropyranyl. Examples of acyl groups include acetyl, propionyl, butyryl, heptanoyl, hexanoyl, valeryl, pivaloyl, isovaleryl, lauryloyl, myristoyl, palmitoyl, stearoyl, oxalyl, malonyl, succinyl, glutaryl, adipoyl, piperoyl, suberoyl, azelaoyl, sebacoyl, acryloyl, propioyl, methacryloyl, crotonoyl, oleoyl, maleoyl, fumaroyl, mesaconoyl, camphoroyl, benzoyl, phthaloyl, isophtaloyl, terephthaloyl, naphthoyl, toluoyl, hydratropoyl, atropoyl, cinnamoyl, furoyl, thenoyl, nicotinoyl and isonicotinoyl. All or part of hydrogen atoms of the above groups can be substituted with fluorine.

Preferred auxiliary repeating units of formulas (46) and (47) are listed in Scheme 13. These auxiliary repeating units can be used singularly or in combination with other auxiliary repeating units.

Scheme 13

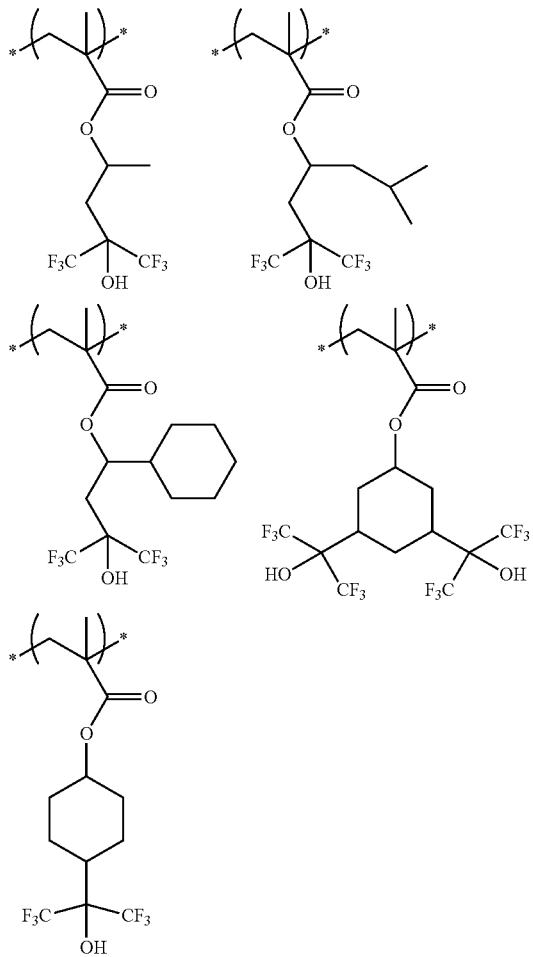

Other preferred auxiliary repeating units of the PAG polymer are those of formula (48):

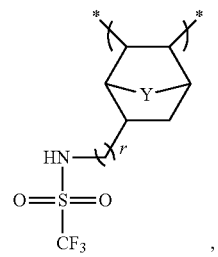

(48)

wherein
r represents an integer of 2 to 6, and
Y represents either *—$CH_2$—*, —*O—* or —*S—*.

Particularly preferred examples of the auxiliary repeating units of formula (48) are listed in Scheme 14. These preferred repeating units can be used singularly or in combination with other auxiliary repeating units.

Scheme 14

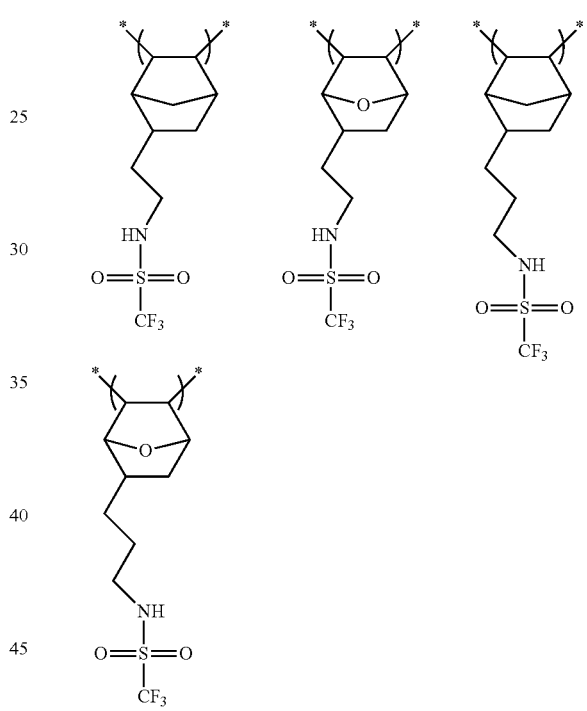

Other preferred examples of auxiliary repeating units include those of formula (49):

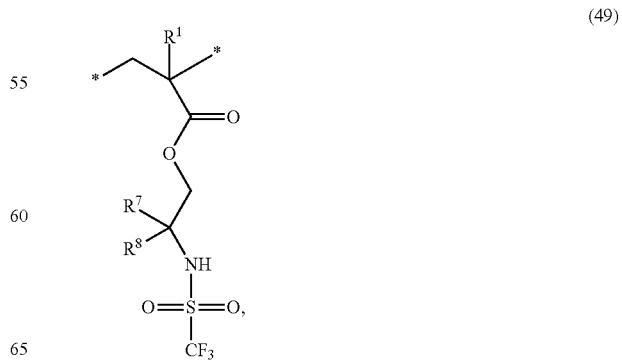

(49)

wherein

R¹ has the same definition as in the general formula (45), and

R⁷ and R⁸ each independently represents a member selected from the group consisting of hydrogen atom, substituted or unsubstituted $C_1$-$C_{25}$ straight chain aliphatic hydrocarbon groups, substituted or unsubstituted $C_1$-$C_{25}$ branched chain hydrocarbon groups, cyclic aliphatic hydrocarbon groups, and substituted or unsubstituted aromatic hydrocarbon groups.

Any number of hydrogen atoms of R⁷ and/or R⁸ can be substituted with a fluorine atom. R⁷ and/or R⁸ can contain an ether bond or a carbonyl group. Exemplary R⁷ and R⁸ groups of formula (49) are the same as those of R⁶ described above for formula (47).

Particularly preferred examples of auxiliary repeating units of formula (49) are listed in Scheme 15. These auxiliary repeating units can be used singularly or in combination with other auxiliary repeating units.

Scheme 15

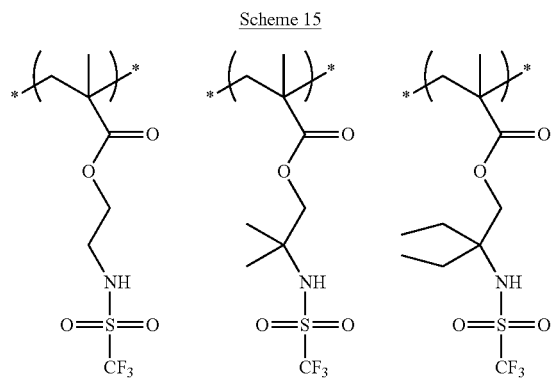

Another preferred examples of auxiliary repeating units include those of formula (50):

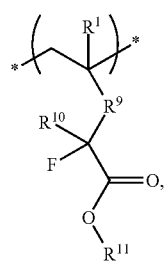

(50)

wherein

R¹ has the same definition as in the general formula (45),

R¹¹ represents a hydrogen atom, a substituted or unsubstituted $C_1$-$C_{25}$ aliphatic hydrocarbon group or a substituted or unsubstituted $C_1$-$C_{25}$ aromatic hydrocarbon group, R⁹ represents a divalent linking group and corresponds in definition to the linking group W¹ described further above, and R¹⁰ represents a hydrogen atom, a fluorine atom, or a fluorine-containing alkyl group.

The fluorine-containing alkyl group of formula (50) can be used without particular limitation. Examples of the fluorine-containing alkyl group are those of 1 to 12 carbon atoms, preferably 1 to 3 carbon atoms, such as trifluoromethyl, pentafluoromethyl, 2,2,2-trifluoroethyl, n-heptafluoropropyl, 2,2,3,3,3-pentafluoropropyl, 3,3,3-trifluoropropyl and 1,1,1,3,3,3-hexafluoropropyl. As R¹⁰, a fluorine atom or a trifluoromethyl group is particularly preferred.

Non-limiting examples of auxiliary repeating units of formula (50) are shown in Scheme 16. These auxiliary repeating units can be used singularly or in combination with other auxiliary repeating units.

Scheme 16

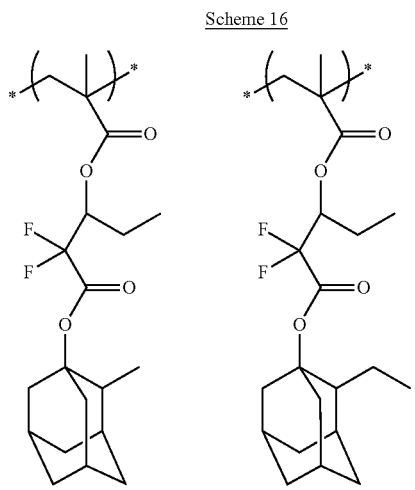

Other non-limiting examples of auxiliary repeating units can comprise ionic PAG groups including those of formula (51):

(51)

wherein

R¹ has the same definition as in the general formula (45),

R¹⁵ represents a divalent linking group,

R¹⁶ represents a monovalent group having a monovalent anion site, preferably either *—SO₃⁻, *—CO₂⁻ or *—NHSO₃⁻, and Q⁺ represents a monovalent cation, preferably either a sulfonium cation or an iodonium cation.

The linking group R¹⁵ has the same definition as the linking group W¹ or W² described further above.

Particularly preferred examples of auxiliary repeating units of formula (51) are shown in Scheme 17. These auxiliary repeating units can be used singularly or in combination with other auxiliary repeating units.

Scheme 17

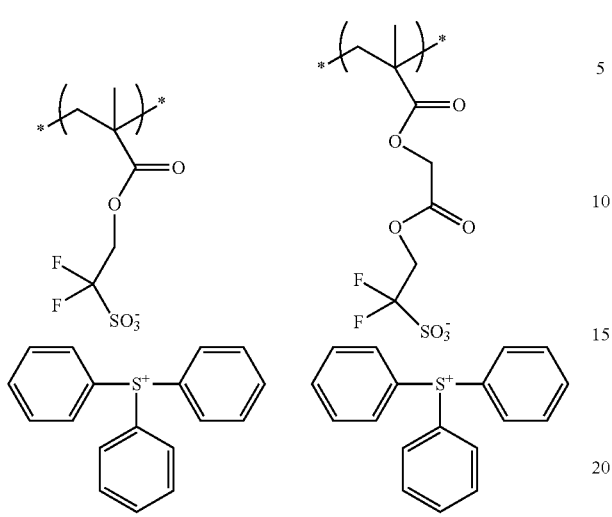

Other auxiliary repeat units include non-acid labile and non-crosslinking analogues of the above-mentioned second repeat units.

Auxiliary Monomers

Preferred auxiliary monomers for forming the auxiliary repeating units include those shown in Scheme 18. These auxiliary monomers can be used singularly or in combination with other auxiliary monomers.

Scheme 18

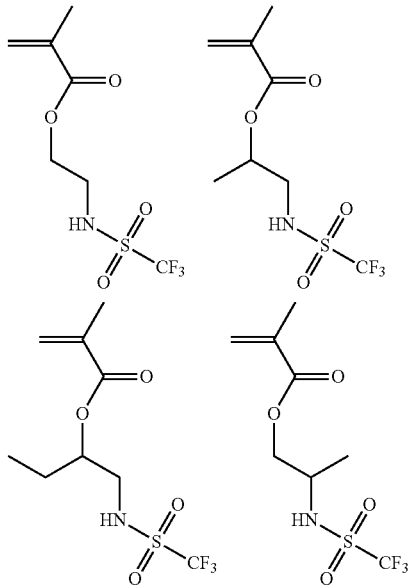

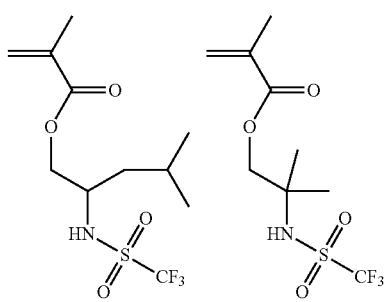

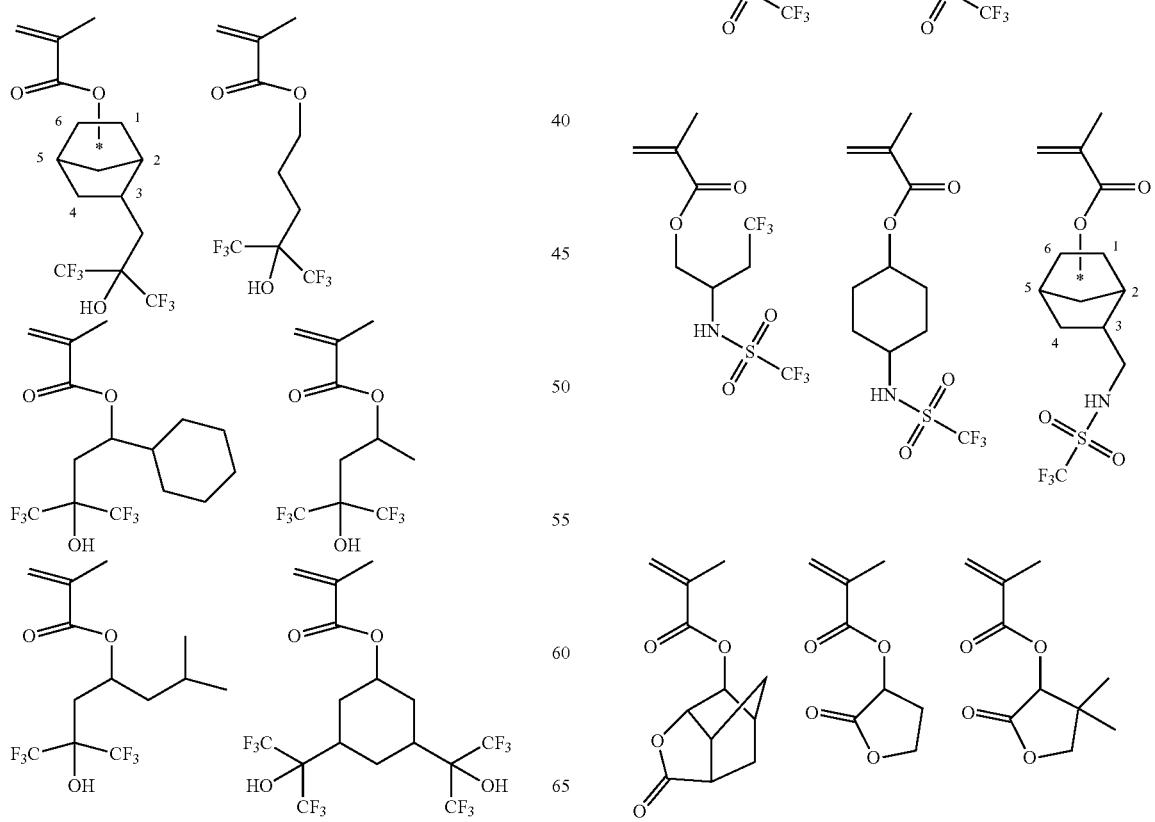

-continued

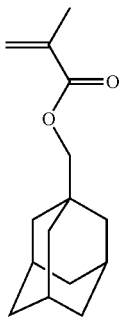

In an embodiment, the PAG polymer comprises 1 mol % to 15 mol % of the first repeating unit, wherein mol % is based on total moles of all monomers of the PAG polymer, 2 mol % to 85 mol % of a second repeating unit having a protected acid group capable of being deprotected by an acid, and the balance being an auxiliary repeating unit comprising a moiety selected from the group consisting of fluoroalcohols, fluorosulfonamides, lactones, alcohol, and combinations thereof. In another embodiment, the protected acid of the second repeating unit is a carboxylic acid group protected with an acid-labile functionality selected from the group consisting of tertiary esters, carbonates, acetals, ketals, and orthoesters.

Preparation of PAG Polymer

A method of forming the PAG polymer comprises i) forming a reaction mixture comprising an above-described PAG monomer (precursor to the first repeating unit of formula (11)), a solvent and a polymerization initiator, and ii) allowing the PAG monomer to polymerize, thereby forming the PAG polymer. The reaction mixture can further comprise an acid labile second monomer (precursor to the second repeating unit) and an auxiliary monomer (precursor to the auxiliary repeating unit) as co-monomers in the polymerization, thereby forming a PAG polymer that is a linear random copolymer. Herein, a "linear polymer" comprises one polymer branch and two chain ends.

No particular limitation is placed on the polymerization process for preparing the PAG polymer comprising the first repeating unit of the general formula (11). Preferably, the PAG polymer is prepared by a radical polymerization process or ionic polymerization process. Other polymerization techniques include coordination anionic polymerization, living anionic polymerization, cationic polymerization, ring opening metathesis polymerization, vinylene polymerization, vinyl addition polymerization, and living radical polymerizations (e.g., atom transfer radical polymerization (ATRP), reversible addition-fragmentation chain-transfer polymerization (RAFT)). The following describes the radical polymerization process. However, it should be understood that the polymerization reaction can be conducted using another polymerization process.

The radical polymerization process can be done by a known polymerization technique (e.g., bulk polymerization, solution polymerization, suspension polymerization, emulsion polymerization techniques) in a batch, semi-continuous or continuous mode in the presence of a radical polymerization initiator and/or a radical initiating source.

There is no particular limitation on the radical polymerization initiator. As the radical polymerization initiator, there can be used azo compounds, peroxide compounds and redox compounds. Preferred examples of the radical polymerization initiator are azobisbutyronitrile, dimethyl-2,2-azobis(2-methylpropionate), tert-butylperoxypivalate, di-tert-butyl peroxide, i-butyryl peroxide, lauroyl peroxide, succinic peroxide, dicinnamyl peroxide, di-n-propylperoxydicarbonate, tert-butylperoxyallyl monocarbonate, benzoyl peroxide, hydrogen peroxide and ammonium persulfate.

There is also no particular limitation on the reaction vessel used in the polymerization reaction. Furthermore, the polymerization reaction can be performed with the use of a polymerization solvent. As the polymerization solvent, preferred are those that do not interfere with the radical polymerization process. Typical examples of the polymerization solvent are: ester solvents such as ethyl acetate and n-butyl acetate; ketone solvents such as acetone and methyl isobutyl ketone; hydrocarbon solvents such as toluene and cyclohexane; and alcohol solvents such as methanol, isopropyl alcohol and ethylene glycol monomethyl ether. Water, ether solvents, cyclic ether solvents, fluorocarbon solvents and aromatic solvents can also be used. These solvents can be used solely or in combination of two or more thereof.

A molecular weight adjusting agent (chain transfer agent) such as mercaptan can be used in combination with the initiating agent.

The reaction temperature of the polymerization reaction is set as appropriate depending on the kind of the radical polymerization initiator or radical initiating source and is generally preferably in the range of 20 to 200° C., more preferably 30 to 140° C.

As a technique for removing water or the organic solvent from the obtained PAG polymer solution or dispersion, it is feasible to adopt re-precipitation, filtration, distillation by heating under reduced pressure, or the like.

Resist Composition

The PAG polymer comprising the PAG repeating unit is used in a resist composition in the form of a solution mixed with other components. The PAG polymer functions as a photo-acid generator. When the PAG polymer further comprises a second repeating unit having an acid-labile group or a cross-linking site and is capable of photo-acid generation and chemical amplification, the PAG polymer can serve as the sole resin of the resist composition, without the addition of a second resin having a repeating unit comprising an acid-labile group or cross-linking site. In this instance, the addition of secondary resin is optional. In the case where the PAG polymer has the PAG repeating unit but does not have the second repeating unit with the acid-labile group or cross-linking site, the resist composition is prepared with the addition of a secondary resin as an essential component to the composition. When the secondary resin is present, the secondary resin is referred to as the "base resin". When the PAG polymer is the sole resin of the resist composition, the PAG polymer is the base resin.

The resist composition can include not only a solvent but also various additives commonly used for resist compositions such as, for example, an additive resin, a quencher, a dissolution inhibitor, a plasticizer, a stabilizer, a coloring agent, a surfactant, a viscosity improver, a leveling agent, an antifoaming agent, a compatibilizer, a primer, and/or an antioxidant. In the case of the negative resist composition, other additives such as a crosslinking agent and/or a basic compound can further be added. The additives can be used in addition to the following materials.

Base Resin

When a second resin is included in the resist composition, the second resin is referred to as the base resin. In this instance, the base resin can contain an acid-labile group so as to perform a positive resist function, or a cross-linking site so as to perform a negative resist function.

Examples of base resins for the positive resist composition are those comprising a repeating unit having a pendant carboxyl group or hydroxyl group protected by an acid-labile group on a side chain thereof, and a main chain portion derived from a polymerization of a vinyl polymerizable group, such as a repeating unit formed by polymerization of acrylic acid, methacrylic acid, α-trifloromethylacrylic acid, a vinyl group, an allyl group, and/or norbornene group.

Examples of the base resin for the negative resist composition are those comprising a repeating unit having a cross-linking site such as a hydroxyl group, a carboxyl group, and/or another above-mentioned functional group capable of forming a crosslink, on a side chain thereof and a main chain portion resulting from a polymerization of a vinyl polymerizable group, such as a repeating unit formed by polymerization of acrylic acid, methacrylic acid, α-trifloromethylacrylic acid, vinyl group, allyl group, and/or norbornene group.

In many cases, the base resin is a copolymer for control of the resist characteristics. There are known various base resins. Herein, the above explanations of the copolymerization component, the acid-labile group, cross-linking site and linking group can be applied as they are to the base resin. As the copolymerization component of the base resin, a lactone ring-containing monomer is particularly preferred for improvement in the substrate adhesion of the resist composition.

The base resin generally has a number average molecular weight of 1,000 to 1,000,000, preferably 2,000 to 500,000, as measured by gel permeation chromatography (GPC). If the number average molecular weight of the base resin is less than 1,000, the resulting resist composition generally does not form a film with sufficient strength. If the number average molecular weight of the base resin exceeds 1,000,000, the solubility of the resin in the solvent decreases, adversely affecting the uniformity of films formed with the resist composition. The molecular weight distribution (Mw/Mn, PDI) of the base resin is preferably in the range of 1.01 to 3.00, most preferably 1.10 to 2.50.

Crosslinking Agents

For a negative resist composition, the cross-linking agent can be any compound formed by reacting an amino-containing compound (e.g., melamine, acetoguanamine, benzoguanamine, urea, ethylene urea, propylene urea, and glycoluril) with formaldehyde or a mixture of formaldehyde and lower alcohol, thereby substituting a hydrogen atom of the amino group with a hydroxymethyl group or a lower alkoxymethyl group. Herein, the cross-linking agents using melamine, urea, alkylene urea (e.g., ethylene urea, propylene urea, and the like) and glycoluril are hereinafter referred to as "melamine-based cross-linking agent", "urea-based cross-linking agent", "alkylene urea-based cross-linking agent" and "glycoluril-based cross-linking agent", respectively. The cross-linking agent is preferably at least one selected from the group consisting of melamine-based cross-linking agents, urea-based cross-linking agents, alkylene urea-based cross-linking agents and glycoluril-based cross-linking agents. Particularly preferred are glycoluril-based cross-linking agents.

Examples of the melamine-based cross-linking agents are hexamethoxymethylmelamine, hexaethoxymethylmelamine, hexapropoxymethylmelamine and hexabutoxymethylmelamine. Hexamethoxymethylmelamine is preferred.

Examples of the urea-based cross-linking agents are bismethoxymethylurea, bisethoxymethylurea, bispropoxymethylurea and bisbutoxymethylurea. Bismethoxymethylurea is preferred.

Examples of the alkylene urea-based cross-linking agents are: ethylene urea-based cross-linking agents such as mono- and/or di-hydroxymethylated ethylene urea, mono- and/or di-methoxymethylated ethylene urea, mono- and/or di-ethoxymethylated ethylene urea, mono- and/or di-propoxymethylated ethylene urea and mono- and/or di-butoxymethylated ethylene urea; propylene urea-based cross-linking agents such as mono- and/or di-hydroxymethylated propylene urea, mono- and/or di-methoxymethylated propylene urea, mono- and/or di-ethoxymethylated propylene urea, mono- and/or di-propoxymethylated propylene urea and mono- and/or di-butoxymethylated propylene urea; 1,3-di(methoxymethyl)-4,5-dihydroxy-2-imidazolidinone; and 1,3-di(methoxymethyl)-4,5-dimethoxy-2-imidazolidinone.

Examples of the glycoluril-based cross-linking agents are mono-, di-, tri- and/or tetra-hydroxymethylated glycoluril, mono-, di-, tri- and/or tetra-methoxymethylated glycoluril, mono-, di-, tri- and/or tetra-ethoxymethylated glycoluril, mono-, di-, tri- and/or tetra-propoxymethylated glycoluril and mono-, di-, tri- and/or tetra-butoxymethylated glycoluril.

The total amount of the cross-linking agent used is preferably 3 to 30 parts by mass, more preferably 3 to 25 parts by mass, most preferably 5 to 20 parts by mass, per 100 parts by mass of the base resin of the resist composition. If the total amount of the cross-linking agent is less than 3 parts by mass of the base resin, the resist composition is generally not capable of sufficient cross-linking to form a desirable resist pattern. The resist composition can exhibit poor storage stability and/or deteriorate in sensitivity with time if the total amount of the cross-linking agent exceeds 30 parts by mass of the base resin.

Basic Compounds

The basic compound is preferably contained as an optional component in the resist composition so as to function as a quencher or to obtain improvements in resist pattern shape and post exposure stability.

Exemplary basic compounds include primary, secondary and tertiary aliphatic amines, aromatic amines, heterocyclic amines, nitrogen-containing compounds with hydroxyphenyl group, alcoholic nitrogen-containing compounds and amide derivatives. Secondary and tertiary aliphatic amines, aromatic amines and heterocyclic amines are preferred.

The aliphatic amines can be in the form of alkylamines or alkylalcoholamines each obtained by replacing at least one hydrogen atom of ammonia ($NH_3$) with a $C_1$-$C_{12}$ alkyl or hydroxyalkyl group. Examples of the aliphatic amines are: monoalkylamines such as n-hexylamine, n-heptylamine, n-octylamine, n-nonylamine and n-decylamine; dialkylamines such as diethylamine, di-n-propylamine, di-n-heptylamine, di-n-octylamine and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decanylamine and tri-n-dodecylamine; and alkylalcoholamines such as diethanolamine, triethanolamine, diisopropanolamine, triisopropanolamine, di-n-octanolamine and tri-n-octanolamine. Above all, alkylacoholamines and trialkylamines are preferred. More preferred are alkylalcoholamines. Among the alkylalcoholamines, triethanolamine and triisopropanolamine are particularly preferred.

Other examples of the basic compound are: aromatic or heterocyclic amines including aniline, aniline derivatives such as N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline and N,N-dimethyltoluidine, heterocyclic amines such as 1,5-diazabicyclo[4.3.0]non-5-ene, 1,8-diazabicyclo[5.4.0]undec-7-ene, 1,4-diazabicyclo[2.2.2]octane, 4-dimethylaminopyridine, hexamethylenetetramine and 4,4-dimethylimidazoline, and hindered amines such as bis(1,2,2,6,6-pentamethyl-4-piperidyl)sebacate; and alcoholic nitrogen-containing compounds such as 2-hydroxypyridine, aminocresol, 2,4-quinolinediole, 3-indole methanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, and 1-[2-(2-hydroxyethoxy)ethyl]piperazine. The basic compounds can be used singularly or in combination.

The amount of the basic compound used is generally 0.01 to 5 parts by mass per 100 parts by mass of the base resin of the resist composition.

Acid Additives

In the case of the negative resist resin, an organic carboxylic acid, a phosphorus oxo acid, and/or a derivative thereof can be added as an optional component in order to prevent sensitivity deterioration caused by the addition of the basic compound and to obtain improvements in resist pattern shape and post exposure stability. This acid compound can be used singularly or in combination with the basic compound.

Exemplary organic carboxylic acid include malonic acid, citric acid, malic acid, succinic acid, benzoic acid and salicylic acid.

Suitable examples of the phosphorus oxo acid and its derivatives are: phosphoric acids and ester derivatives thereof, such as phosphoric acid, di-n-butyl phosphate and diphenyl phosphate; phosphonic acids and ester derivatives thereof, such as phosphonic acid, dimethyl phosphonate, di-n-butyl phosphonate, phenylphosphonic acid, diphenyl phosphonate and dibenzyl phosphonate; and phosphinic acids or ester derivatives thereof, such as phosphinic acid and phenylphosphinic acid. Phosphonic acid is particularly preferred.

Solvents

There is no particular limitation on the organic solvent as long as the PAG polymer can be dissolved in the organic solvent. Non-limiting organic solvent include: ketones such as acetone, methyl ethyl ketone, cyclohexanone, methyl isoamyl ketone and 2-heptanone; polyhydric alcohols and derivatives thereof, such as monomethyl ether, monoethyl ether, monopropyl ether, monobutyl ether or monophenyl ether of ethylene glycol, ethylene glycol monoacetate, diethylene glycol, diethylene glycol monoacetate, propylene glycol, propylene glycol monoacetate, propylene glycol monomethyl ether, propylene glycol monomethyl etheracetate (PGMEA), dipropylene glycol or dipropylene glycol monoacetate; cyclic ethers such as dioxane; esters such as methyl lactate, ethyl lactate, methyl acetate, ethyl acetate, butyl acetate, methyl pyruvate, ethyl pyruvate, methyl methoxypropionate and ethyl ethoxypropionate; aromatic solvents such as xylene and toluene; and fluorinated solvents such as fluorocarbon, hydrofluorocarbon, perfluoro compound and hexafluoroisopropyl alcohol. There can also be used a high-boiling-point weak solvent such as turpentine-based petroleum naphtha solvent or paraffin solvent for improvement in ease of application. These solvents can be used singularly or in combination.

Surfactants

Preferred surfactants for the resist composition include one or more fluorine- and/or silicon-based surfactants (i.e., fluorine-based surfactant, silicon-based surfactants, and surfactant containing both of fluorine and silicon atoms).

A resist composition comprising a surfactant is generally effective for use with an exposure light source of 250 nm or less wavelength, notably 220 nm or less wavelength and for pattern formation with a narrower pattern line width. It is possible to attain good sensitivity and resolution and obtain good resist patterning with less adhesion/development failures.

Non-Resinous Acid Generator

The resist composition can include a non-resinous photo-acid generator in combination with the PAG polymer. These include common photo-acid generators for chemically amplified resist compositions. Exemplary non-resinous photo-acid generators include bis-sulfonyldiazomethanes, nitrobenzyl derivatives, onium salts, halogen-containing triazine compounds, cyano-containing oximesulfonate compounds and other oximesulfonate compounds. These photo-acid generators can be used singularly or in combination. The amount of the photo-acid generator used, including the PAG polymer, is generally in the range of 0.5 to 20 parts by mass per 100 parts by mass of the resist composition. If the amount of the photo-acid generator is less than 0.5 parts by mass, the resist composition is generally not effective in forming good resist patterns. If the amount of the photo-acid generator exceeds 20 parts by mass, it is difficult to prepare the resist composition as a uniform solution. Moreover, storage stability of the resist composition decreases. The PAG polymer is generally used in an amount of 1 to 100 parts by mass, preferably 10 to 100 parts by mass, more preferably 30 to 100 parts by mass, per 100 parts by mass of the total photoacid generator content.

Additive Resins

The resin composition can include resins in addition to the PAG polymer and secondary resin (base resin). There is no particular limitation placed on the additive resin as long as the additive resin can be dissolved in the solvent used and has compatibility with the other components of the resist composition. The additive resin can function as an in-situ top coat, a plasticizer, a stabilizer, as a viscosity improver, a leveling agent, an antifoaming agent, a compatibilizer, and/or a primer.

Pattern Formation Method

Figure 1B:
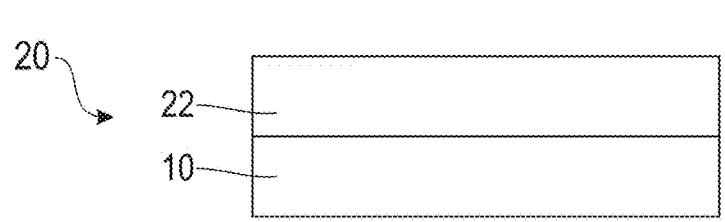
Figure 1C:
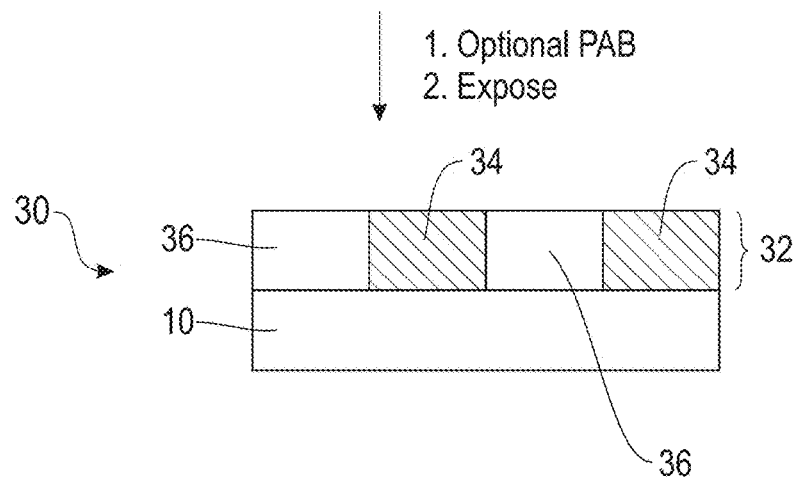

The following discussion pertains to a method of patterning a desired substrate, such as, for example, a silicon wafer, a chrome-on-glass mask blank, or a printed circuit board using a resist composition comprising the PAG polymer as the base resin, (i.e., the PAG polymer comprises the photosensitive first repeating unit and acid labile second repeating unit, and is capable of photo-acid generation as well as chemical amplification by formation of acid groups). In this instance, a positive-tone lithographic pattern can be formed, as illustrated in the schematic layer diagrams of FIGS. 1A to 1E. A resist composition comprising at least the PAG polymer and a solvent is disposed on surface 12 of substrate 10 (FIG. 1A) using any suitable coating technique (e.g., spin casting) followed by removal of the solvent to form resist layer 22 of structure 20 (FIG. 1B). Resist layer 22 comprises the solid components of the resist composition. Resist layer 22 can be treated with an optional post-application bake (PAB) and/or an optional solvent rinse under suitable conditions of time and temperature before exposure. Patternwise exposure of resist layer 22 to high energy radiation results in exposed resist layer 32 of structure 30 (FIG. 1C).

For patterning of features smaller than 40 nm it is particularly effective to use an exposure device having a light source for irradiating high energy radiation of wavelength 124 nm or less, such as EUV, x-ray, and/or E-beam.

Optionally, the resist layer can be exposed using a liquid immersion exposure device that uses a medium such as water and/or a hydrocarbon or fluorinated liquid in the optical path, which causes less absorption of high energy radiation and enables more efficient fine processing in terms of numerical aperture and effective wavelength. Most commonly, liquid immersion lithography is performed using 193 nm radiation.

Figure 1D:
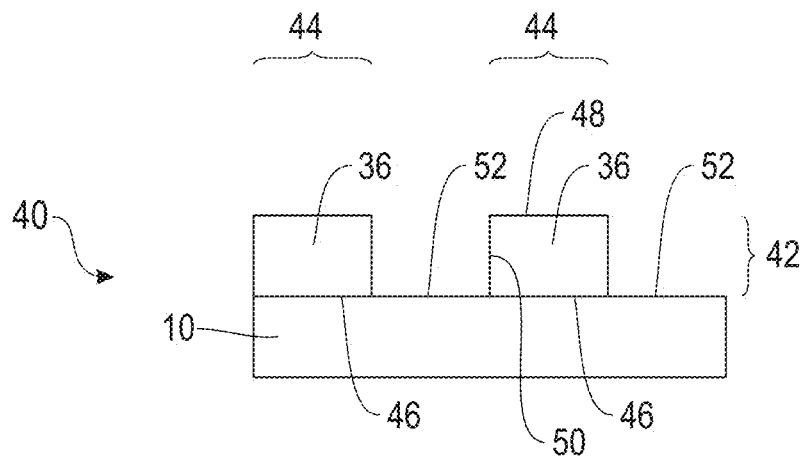
Figure 1E:
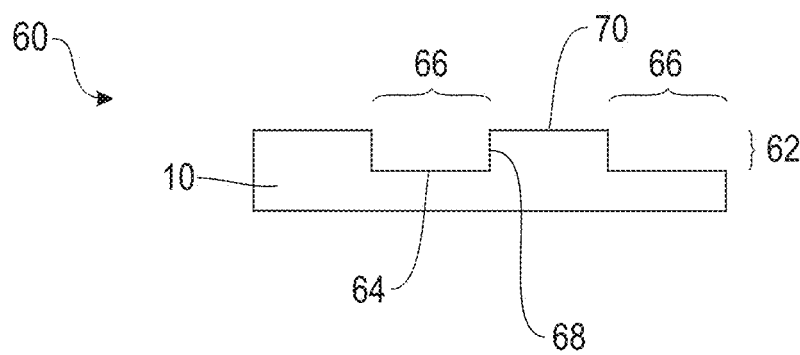

Exposed resist layer 32 is composed of regions of exposed resist 34 and regions of non-exposed resist 36. Exposed resist layer 32 can be treated with an optional post-exposure bake (PEB) and/or an optional solvent rinse under suitable conditions of time and temperature before development. The exposed resist 34 and/or baked exposed resist 34 has greater solubility in an aqueous alkaline developer compared to non-exposed resist 36. Consequently, aqueous alkaline development affords a positive-tone image by removing regions of exposed resist 34. The PAB, PEB and/or solvent rinse(s) can enhance solubility differences of the exposed and non-exposed resist in a given developer. Development in an aqueous alkaline developer produces layered structure 40 comprising patterned resist layer 42 (FIG. 1D). Patterned resist layer 42 is a topographical relief pattern comprising resist features 44 composed of non-exposed resist 36. Resist features 44 are disposed on surface 46 of substrate 10 and have top surface 48 and sidewall 50. Substrate surface 52 is in contact with air. The topographical relief pattern of patterned resist layer 42 can be transferred to substrate 10 by known methods (e.g., reactive ion etching) followed by removal of resist features 44, resulting in structure 60 (FIG. 1E). Structure 60 comprises a transferred topographical pattern 62 within substrate 10, whose features 66 comprise bottom surface 64, sidewall surface 68, and top surface 70 of substrate 10.

Figure 2:
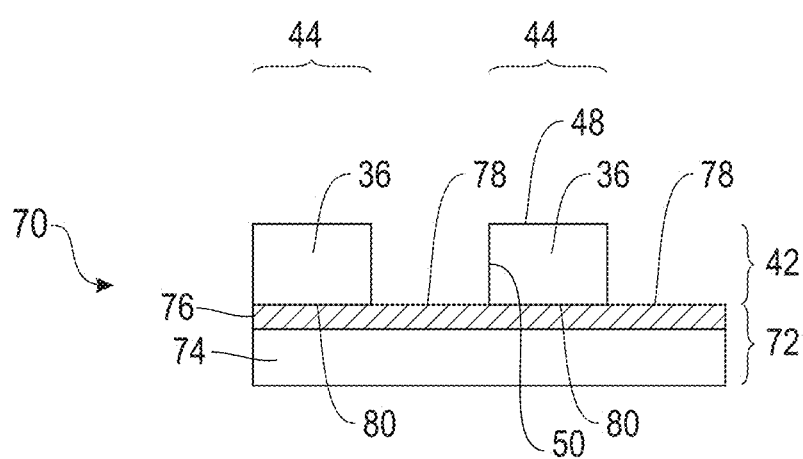
FIG. 2 is a schematic layer diagram of a multi-layered structure that includes a topographical patterned layer comprising an exposed resist composition disposed on a two layered substrate.

To further illustrate a multi-layered substrate, structure 40 of FIG. 1D is reproduced as structure 70 of FIG. 2, with the exception that substrate 72 of FIG. 2 has two layers, a bottom layer 74 and an intermediate layer 76. Bottom layer 74 of substrate 72 can be, for example, a silicon wafer. Intermediate layer 76 can be, for example, an ARC layer. In this example, surface 78 is a surface of the ARC layer in contact with air, and resist features 44 are disposed on ARC surface 80.

The resist layer can be rinsed before or after the exposure, the PAB, and/or the PEB with a solvent (e.g., water, aqueous solutions, including water/alcohol mixtures, and organic solvents). Typically, the rinse is performed after the PAB. Rinses can be performed at or near room temperature (e.g., 10° C. to 50° C.) for a period of 1 second to 1 hour.

Optionally, the pre-developed resist layer and/or post-developed resist layer can be treated with water vapor and/or alcohol vapor either at room temperature or at elevated temperature on a time scale of 1 minute to 5 hours. Such a treatment after exposure and PEB can be conducted, for example, to promote additional acid induced deprotection of acid sensitive groups.

The term "substrate" refers to all underlying layers of a structure on which the resist layer is disposed. The substrate can have one or more layers arranged in a stack. In a multi-layered substrate, the layer directly below and in contact with the resist layer is the top-most layer of the substrate, also referred to as "the underlayer" to the resist layer. The terms "surface" or "underlying surface" refer to the substrate surface on which the resist layer is disposed. As non-limiting examples, the resist layer can be disposed on the surface of a silicon wafer or a metal foil, or more particularly on the surface of an anti-reflection layer (ARC) of a multi-layer substrate, where the ARC layer is the top-most layer of the substrate. In this example, the ARC layer is also the underlayer of the resist layer. In another example, the ARC layer has a polymer brush layer attached to the top surface. In this example, the polymer brush layer is also the underlayer of the resist layer.

The term "disposed" refers to a layer in contact with a surface of another layer. "Disposing" or "applying" refer to forming a layer to be in contact with a surface of another layer, without limitation as to the method employed unless otherwise stated, providing the desirable properties of the disposed or applied layer are not adversely affected (e.g., uniformity and thickness).

The term "casting" refers to forming a layer of a material by disposing a solution of the material dissolved in a solvent on a surface of another layer, and removing the solvent.

It should be understood that in some cases (e.g., when forming dense, high resolution patterns) all of the resist layer can receive some dose of radiation exposure. "Non-exposed resist" refers to resist that has received an insufficient dose to switch the solubility of the resist in a given developer compared to the pre-exposed resist (including pre-exposed resist that has been treated with an optional bake and/or optional rinse). "Exposed resist" has received sufficient exposure to switch the solubility of the resist in a given developer compared to the pre-exposed resist.

"Polarity change" implies an altered chemical composition that affects relative solubility without crosslinking. The extent of the polarity change can be measured by comparing the solubility of the exposed resist and non-exposed resist in a given developer. "Inducing a polarity change" in the resist layer means subjecting the resist layer to a treatment involving exposure, a post-exposure bake (PEB) and/or an optional rinse that alters the chemical composition of the layer such that the treated resist has a different solubility compared to the pre-treated resist in a given developer (e.g., tetramethylammonium hydroxide (TMAH) solution in water).

The optional baking (PAB and/or PEB) treatments and/or optional rinsing treatments can enhance the solubility difference of the exposed resist compared to the non-exposed resist. A PAB and/or PEB can be used to facilitate deprotection of acid sensitive protecting groups and/or elimination of reaction byproducts of the resist composition.

The optional post-application bake (PAB) treatment is typically performed at a temperature of 50° C. to 250° C. for a period of 1 second to 10 minutes, more specifically 90° C. to 130° C. for about 1 minute. The PAB can be used to dry the film of excess solvent, remove unwanted or excess organic ligand, and/or partially crosslink the resist layer. The thermally treated dry film typically will have a thickness of 0.01 micrometers to 10 micrometers, depending on the subsequent radiation source and the desired application.

The optional post-exposure bake (PEB) can be performed at a temperature of 50° C. to 300° C. for 1 second to 10 minutes, more specifically 90° C. to 130° C. for about 1 minute.

Developers

The aqueous alkaline developer for positive tone development can comprise any suitable base. Non-limiting exemplary bases include sodium hydroxide, potassium hydroxide, sodium carbonate, and various tetraalkylammonium hydroxides such as, for example, tetramethylammonium hydroxide (TMAH) and tetrabutylammonium hydroxide (TBAH). The aqueous alkaline developer can comprise one or more bases. Preferably, the aqueous alkaline developer comprises a tetraalkylammonium hydroxide, more preferably tetramethylammonium hydroxide. Preferably, the TMAH developer comprises 0.1 to 5 wt % tetramethylammonium hydroxide (TMAH) based on total weight of the developer solution in water.

The aqueous alkaline developer for negative tone development can comprise any of the aqueous alkaline developers described above. The organic solvent developer for negative tone development can comprise any suitable organic solvent. Non-limiting exemplary organic solvents include ketone-based solvents, ester-based solvents, alcohol-based solvents, amide-based solvents, ether-based solvents, and hydrocarbon-based solvents. More specific organic solvent developers include methyl benzoate (MeB), ethyl 3-ethoxypropionate (EEP), 2-heptanone (MAK), 4-methyl-2-pentanone (4M2P), n-butyl acetate (NBA), propylene glycol methyl ether acetate (PGMEA), anisole, acetophenone, and combinations thereof.

Post-Development Treatment

The patterned resist layer can also be given a post-development treatment, for example, to increase etch resistance. The post-development treatment can be photochemical, thermal, chemical, or a combination thereof. As an example, the patterned resist layer can be given a second exposure to a second radiation, thereby forming a treated patterned resist layer. The second exposure can be performed with a single wavelength of second radiation or a combination of suitable wavelengths (broad band) of second radiation, so long as the exposure is effective in inducing the desired response of the treated patterned resist layer. The second exposure treatment can be a flood exposure. The flood exposure can be a single conventional whole area exposure or a combination of conventional whole area exposures. The exposure treatment can also be a scanning exposure delivered by a digital writing device employing light emitting sources. The second exposure can be followed by a thermal treatment to chemically amplify the formation of chemical functional groups in the treated patterned resist layer. For example, the flood exposure can release an acid from previously unreacted photoacid generator (PAG) that upon subsequent heating catalyzes the deprotection of additional acid-sensitive carboxylic acid esters, aromatic acetals/ketals, and/or carbonates, thereby increasing the concentration of carboxylic acid and phenol groups in the treated patterned resist layer. With sufficient polarity change, the treated patterned resist layer can be rendered insoluble in either a low polarity solvent (e.g., anisole) or a more polar organic solvent, while retaining solubility in aqueous alkaline developer and/or a second organic solvent, without crosslinking the resist.

A post-development thermal treatment can further tailor the solvent compatibility, chemical structure of the resist material, and/or etch resistance of the patterned resist layer. The thermal treatment can be conducted at a temperature of 50° C. to 600° C., 50° C. to 300° C., or 50° C. to 200° C. for a period of 1 sec to 1 day.

A chemical treatment can include, for example, contacting the patterned resist layer with the vapors of a volatile Lewis acid, such as hydrochloric acid, sulfuric acid, nitric acid, or a sulfonic acid. In each type of treatment, the chemical alteration of the resist is preferentially uniformly distributed throughout the treated resist, not just at the surface. The post-development chemical treatment can cause a chemical change in the revealed surface of the substrate, producing (after removal of the resist features) a chemically patterned surface of the substrate.

Etching includes any common etching technique applied in the manufacture of semiconductor devices, for example, dry-etching such as plasma etching, or wet-etching using selective solvents. Typically, dry etching processes are employed for etching at sub-50 nm dimensions.

Substrate

The substrate, and more particularly the surface of the substrate, can comprise inorganic or organic materials such as metals, carbon, or polymers. More particularly, the substrate can comprise any semiconducting material including, for example, Si, SiGe, SiGeC, SiC, Ge alloys, GaAs, InAs, InP, as well as other III-V or II-VI compound semiconductors. The substrate can also comprise a layered semiconductor such as Si/SiGe, or a semiconductor-on-insulator (SOI). In particular, the substrate can contain a Si-containing semiconductor material (i.e., a semiconductor material that includes Si) such as, for example, silicon dioxide, silicon nitride, and quartz. The semiconductor material can be doped, undoped or contain both doped and undoped regions therein.

The following examples demonstrate the preparation of the PAG monomers, PAG polymers, resist compositions thereof, and resist patterns formed thereof. The resist formulations were not optimized.

EXAMPLES

Commercially available materials used in the following examples are listed in Table 1.

TABLE 1

| ABREVIATION | DESCRIPTION | SUPPLIER |
| --- | --- | --- |
| MF-26A | 2.3 Wt % Aqeous Tetramethyl Ammonium Hydroxide Solution (TMAH) | FUJIFILM |
| Quencher | 2-Phenyl Benzimidazole | Sigma-Aldrich |
| FSAF3 | 2-(Fluorosulfonyl)Difluoroacetyl Fluoride | Synquest |
| | 2,3,5,6-Tetrafluoro-4-Sulfobenzoic Acid | TCI |
| | N-Bromosuccinimide | Sigma-Aldrich |
| | 2'-Methoxyacetophenone | Sigma-Aldrich |
| NBHFAMA | 2-{[5-(1',1',1'-Trifluoro-2'-Trifluoromethyl-2'-Hydroxy)Propyl]Norbornyl]} Methacrylate | Central Glass |
| ECPMA | 1-Ethylcyclopentyl Methacrylate | JSR |
| Cl-IMA | 2-(Chlorosulfonyl)-2,2-Difluoroethyl Methacrylate | Central Glass |
| Vazo 52 | 2,2'-Azobis(2,4-Dimethylvaleronitrile) | Wako |
| MA EA HCl | 2-Aminoethyl Methacrylate Hydrochloride | Central Glass |
| | 4-Vinyl Aniline | Sigma-Aldrich |
| | (Trifluoromethyl)Trimethylsilane | Sigma-Aldrich |
| | Phenylglyoxal Hydrate | Sigma-Aldrich |

Herein, Mn is the number average molecular weight, Mw is the weight average molecular weight, and MW is the molecular weight of one molecule.

The following examples are intended to provide those of ordinary skill in the art with a complete disclosure and description of how to prepare and use the compositions disclosed and claimed herein. Unless indicated otherwise, parts are parts by weight, temperature is in degrees centigrade (° C.), and pressure is at or near atmospheric pressure. Additionally, all starting materials including the co-monomers other than the PAG monomers were obtained commercially or were synthesized using known procedures.

Where appropriate, the following techniques and equipment were utilized in the examples below. $^1$H NMR and $^{13}$C NMR spectra were obtained at room temperature on an Avance 400 spectrometer. Quantitative $^{13}$C NMR was run at room temperature in acetone-$d_6$ in an inverse-gated $^1$H-decoupled mode using Cr(acac)$_3$ as a relaxation agent on an Avance 400 spectrometer. Thermo-gravimetric analysis (TGA) was performed at a heating rate of 5° C./minute in N$_2$ on a TA Instrument Hi-Res TGA 2950 Thermogravimetric Analyzer. Differential scanning calorimetry (DSC) was performed at a heating rate of 10° C./minute on a TA Instruments DSC 2920 modulated differential scanning calorimeter. Number average and weight average molecular weights were measured in tetrahydrofuran (THF) or dimethylformamide (DMF) on a Waters Model 150 chromatograph relative to polystyrene standards.

In the structures that follow Ph=phenyl, and Ad=1-Adamantyl.

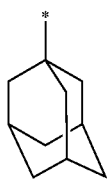

1-Adamantyl

Resist film layers containing the PAGs were exposed using a 193 nm interferometric tool (IBM Designed NEMO) or a 0.3 NA EUV micro-exposure tool (EUV-MET) at Lawrence-Berkeley National laboratory.

Synthesis of Starting Materials for PAG

Amide-sulfonyl fluoride compounds of Examples 1-4 were prepared using the general reaction shown below, where n=1.

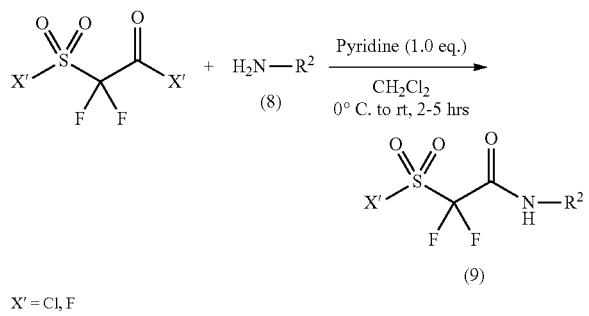

X' = Cl, F

Example 1. Preparation of SM-1: 2-(4-(chlorosulfonyl)-2,3,5,6-tetrafluorobenzamido)ethyl methacrylate Step A. 2,3,5,6-Tetrafluoro-4-sulfobenzoic acid (TCI, 4.28 g, 0.0156 mol) was added to a 100 mL round bottom flask along with a magnetic stir bar, followed by phosphorous pentachloride (PCl$_5$, 8.14 g, 0.039 mol, 2.5 eq.) and phosphorous(V) oxychloride (POCl$_3$, 2.14 mL, 0.0234 mol, 1.5 eq.). The reaction mixture was then quickly attached to a Vigreux reflux condenser with nitrogen inlet. The reaction was purged with nitrogen then heated to 90° C. for a period of 2 hours. The phosphorous salts were precipitated from the reaction mixture using dry hexanes (100 mL). The resulting cloudy white solution was filtered under nitrogen and concentrated in vacuo to give 4-(chlorosulfonyl)-2,3,5,6-tetrafluorobenzoyl chloride as a light yellow oil that crystallized upon standing. Analytical spectral data for this compound were consistent with previously reported data in the literature (Fielding, H. C., Shirley, I. M., "Synthesis and reactions of 4-sulpho-2,3,5,6,-tetrafluorobenzoic acid", Journal of Fluorine Chemistry (1992), 59, 15-31).

Step B. In a 20 mL vial, 2-aminoethyl methacrylate hydrochloride (0.586 g, 3.53 mmol, 1.0 eq.) was neutralized with pyridine (0.571 mL, 2 eq.) in dichloromethane (CH$_2$Cl$_2$, 15 mL). Neutralization proceeded by rapidly stirring the mixture for 20 minutes followed by sonication for 3 minutes. The solution was then set aside. Dichloromethane (10 mL) was added to a round bottom containing a magnetic stir bar and 4-(chlorosulfonyl)-2,3,5,6-tetrafluorobenzoyl chloride (1.1 g, 3.53 mmol). The solution was rapidly stirred under nitrogen until all material dissolved. The reaction vessel was fitted with an addition funnel charged with the neutralized 2-aminoethyl methacrylate solution and having a nitrogen inlet. The reaction mixture was then cooled to 0° C. in an ice bath followed by the dropwise addition of neutralized reagent. Dichloromethane (5 mL) was used to rinse the addition funnel and this solution was added to the reaction. The reaction was stirred at room temperature over the course of 18 hours, after which the reaction was diluted with dichloromethane (50 mL), extracted with 1M HCl, dried using anhydrous magnesium sulfate (MgSO$_4$), and concentrated in vacuo. The crude 2-(4-(chlorosulfonyl)-2,3,5,6-tetrafluorobenzamido)ethyl methacrylate was then purified by column chromatography in dichloromethane and 1.5% (by volume) methanol. $^1$H NMR (400 MHz, CD$_2$Cl$_2$); delta=6.56 (s, 1H), 6.12 (s, 1H), 5.63 (s, 1H), 4.35 (t, J=5.5 Hz, 2H), 3.79 (q, J=5.6 Hz, 2H), 1.93 (s, 3H). $^{19}$F NMR (376 MHz, CD$_2$Cl$_2$); delta=−131.72 to −132.13 (m), −135.17 to −135.29 (m, 2F).

Example 2. Preparation of SM-2: 2-(2,2-difluoro-2-(fluorosulfonyl)acetamido)ethyl methacrylate

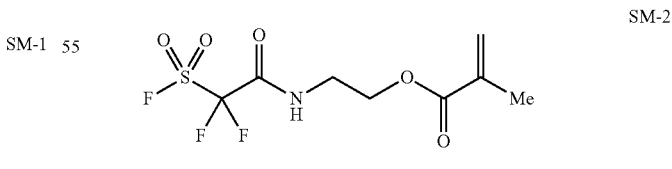

A 500 ml flask was charged with CH$_2$Cl$_2$ (80 ml) under nitrogen stream and stirred for 10 minutes at 0° C. and then 2-(fluorosulfonyl)difluoroacetyl fluoride (29.9 g, 166.0 mmol, 1.5 equivalent (eq.)) was added. After 25 minutes, a CH$_2$Cl$_2$ (160 ml) solution of 2-aminoethyl methacrylate hydrochloride (18.4 g, 111.0 mmol, 1.0 eq.) and pyridine (17.5 g, 221.0 mmol, 2.0 eq.) was added dropwise to the mixture over 50 minutes. The mixture was allowed to warm to room temperature (RT) and stirred for 3 hours at RT. 1N HCl was added to the final reaction mixture and the lower layer was separated and subsequently washed with an additional amount of 1N HCl followed by brine. The solution was dried over anhydrous MgSO$_4$, filtered and the CH$_2$Cl$_2$ removed by an evaporator. The crude product was purified by recrystallization (hexane/CHCl$_3$). The target compound was obtained as a white solid (20.4 g) in 64% yield. $^1$H-NMR (400 MHz, CDCl$_3$); delta=1.93 (dd, J=1.1, 1.2 Hz, 3H), 3.73 (td, J=5.4, 5.2 Hz, 2H), 4.35 (dd, 5.0 Hz, 2H), 5.63 (dq, J=1.4, 1.5 Hz, 1H), 6.12-6.14 (m, 1H), 7.09 (brs, 1H). $^{19}$F-NMR (376 MHz, CDCl$_3$, C$_6$F$_6$ as standard); delta=40.68 (t, J=5.1 Hz, 1F), −105.91 (d, J=4.8 Hz, 2F).

Example 3. Preparation of SM-3: 1,1-difluoro-2-oxo-2-(4-vinylphenylamino)-1-ethanesulfonyl fluoride

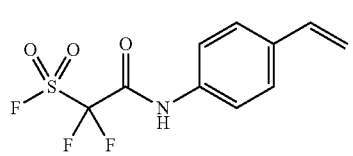

SM-3

100 ml flask was charged with CH$_2$Cl$_2$ (24 ml) under nitrogen stream and allowed to equilibrate to 0° C. by stirring in an ice bath for 10 minutes, then 2-(fluorosulfonyl)difluoroacetyl fluoride (6.60 g, 37.6 mmol, 1.5 eq.) was added. After 20 minutes, a CH$_2$Cl$_2$ (12 ml) solution of 4-vinyl aniline (2.86 g, 24.4 mmol, 1.0 eq.) and pyridine (1.93 g, 24.4 mmol, 1.0 eq.) was added drop wise to the mixture over 10 minutes. The mixture was allowed to warm to RT and was stirred for 4 hours at RT. 1N HCl was added to the final reaction mixture and the lower layer was separated and washed with 1N HCl and brine. The solution was dried over anhydrous MgSO$_4$, filtrated and then CH$_2$Cl$_2$ was removed by an evaporator. The target compound was obtained as a white solid (6.57 g) in 96% yield. $^1$H NMR (400 MHz, CDCl$_3$); delta=5.28 (d, J=10.9 Hz, 1H), 5.74 (d, J=17.6 Hz, 1H), 6.68 (dd, J=10.9, 17.6 Hz, 1H), 7.43 (d, J=8.6 Hz, 2H), 7.53 (d, J=8.7 Hz, 2H), 8.04 (brs, 1H). $^{19}$F-NMR (376 MHz, CDCl$_3$, C$_6$F$_6$ as standard) delta=41.27 (t, J=4.6 Hz, 1F), −105.26 (d, J=4.2 Hz, 2F).

Example 4. Preparation of SM-4: 2-hydroxy-2-trifluoromethylacetophenone

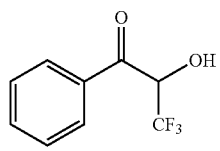

SM-4

A 500 ml flask was charged with phenylglyoxal hydrate (15.21 g, 100 mmol, 1.0 eq.), (trifluoromethyl)trimethylsilane (31.1 g, 205 mmol, 2.05 eq.), and dimethoxyethane (200 mL) under nitrogen stream. The mixture was stirred for 10 minutes at 0° C., after which CsF (280 mg, 2.0 mmol, 0.02 eq.) was added to the mixture in small portions over 10 minutes. The reaction mixture was stirred for 1.5 hours at 0° C. (caution: this reaction has an induction period and is exothermic). Subsequently, the mixture was stirred for 30 minutes at room temperature. THF (20 mL) and 6N HCl (80 mL) were added followed by stirring for 1.5 hours. The upper layer was separated, the lower layer was extracted with Et$_2$O (100 ml×2), and the organic layers were combined. The organic solution was washed with brine (50 mL), dried over anhydrous MgSO$_4$, and filtered. Solvents were removed in an evaporator and the crude product was purified by column chromatography (hexane/AcOEt) to obtain the target compound as a white solid (2.96 g, 14.5% yield). $^1$H-NMR (CDCl$_3$), delta (ppm): 4.28 (d, J=8.3 Hz, 1H), 5.44 (qd, J=6.6, 8.3 Hz, 1H), 7.58 (dd, J=7.8, 7.9 Hz, 1H), 7.73 (t, J=7.5 Hz, 1H), 8.01 (d, J=7.7 Hz, 1H), $^{19}$F-NMR (CDCl$_3$, standard: C$_6$F$_6$=−162.2 ppm), delta (ppm): −74.34 (d, J=6.6 Hz, 3F).

Example 5. Preparation of SM-5: 2-Hydroxy-2'-methoxyacetophenone

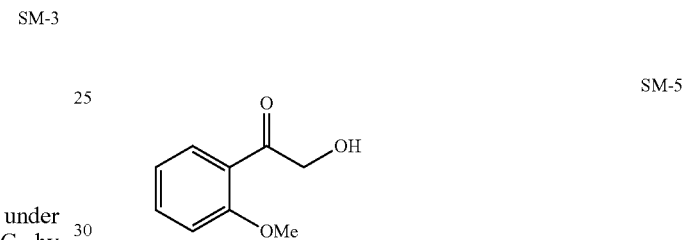

SM-5

Step A. A 200 mL flask was charged with 2'-methoxyacetophenone (7.51 g, 50 mmol), N-bromosuccinimide (9.79 g, 55 mmol), p-toluenesulfonic acid (10.79 g, 55 mmol) and MeCN (100 mL) under nitrogen stream and the mixture was stirred for 3.5 hours at 80° C. The mixture was allowed to cool to room temperature and then MeCN was removed by an evaporator. CHCl$_3$ (150 mL) and H$_2$O (50 mL) were added to a residue and the lower layer was separated and then washed with saturated aqueous NaHCO$_3$ (50 mL) twice and brine (50 mL). The solution was dried over anhydrous MgSO$_4$ and filtrated. Solvents were then removed in an evaporator and the crude product as orange-brown oil (11.74 g) in >99.9% yield was obtained. This product was identified as 2-Bromo-2'-methoxyacetophenone contaminated with some dibromo compound. $^1$H-NMR (CDCl$_3$), delta (ppm): 3.93 (s, 3H), 4.59 (s, 2H), 6.97 (d, J=8.4 Hz, 1H), 7.00-7.06 (m, 1H), 7.50 (ddd, J=1.8, 7.3, 8.4 Hz, 1H), 7.81 (dd, 7.7 Hz, 1H).

Step B. A 200 mL flask was charged with the crude of 2-Bromo-2'-methoxyacetophenone obtained in Step A (11.74 g, 50 mmol, 1.0 eq.) and MeOH (100 mL) under nitrogen stream and then HCOONa (10.20 g, 150 mmol, 3.0 eq.) was added. The mixture was stirred for 4 hours at 80° C. The mixture was allowed to cool to room temperature and the remaining solid (HCOONa) was filtrated and then the filtrate was concentrated in an evaporator. CHCl3 (150 mL) was added to the residue and the precipitated solid was filtrated through celite and the celite was washed with CHCl$_3$ (50 mL). H$_2$O (50 mL) were added to the filtrate and the lower layer was separated and washed with saturated aqueous NaHCO$_3$ (50 mL) twice and brine (50 mL). MeOH (50 mL) and HCOONa (3.4 g, 50 mmol, 1.0 eq.) were added to the crude material and then the mixture was stirred for 3 hours at 80° C. The mixture was allowed to cool to room temperature and the remaining solid (HCOONa) was filtrated and then the filtrate was concentrated in an evaporator. CHCl$_3$ (100 mL) was added to the residue and the precipitated solid was filtrated and then the solid was washed with CHCl$_3$ (50 mL). H$_2$O (50 mL) were added to the combined filtrate and the lower layer was separated and washed with 1N HCl (50 mL) and brine (50 ml) twice. The solution was dried over anhydrous MgSO$_4$ and filtered and then solvents were removed in an evaporator. The crude material was purified by column chromatography (Hexane/AcOEt) to obtain the target compound as pale yellow solid (4.22 g) in 50.8% yield. $^1$H-NMR (CDCl$_3$), delta (ppm): 4.8 (t, J=4.8 Hz), 3.97 (s, 3H), 4.79 (d, J=4.0 Hz, 2H), 7.03 (d, J=8.4 Hz, 1H), 7.09 (ddd, 7.5, 7.6 Hz, 1H), 7.58 (ddd, J=1.8, 7.6, 8.1 Hz, 1H), 8.08 (dd, J=1.8, 7.8 Hz, 1H).

Synthesis of PAG Monomers

Example 6. Preparation of Monomer M-1

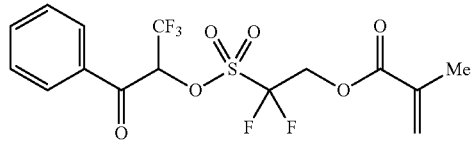

A 50 ml flask was charged with 2-hydroxy-2-trifluoromethylacetophenone (SM-4, 0.98 g, 4.80 mmol, 1.0 eq.) and THF (12 ml) under nitrogen stream. The mixture was stirred for 10 minutes at −30° C. before adding dropwise n-BuLi (3.0 mL, 4.80 mmol, 1.0 eq. 1.6 M) to the mixture over 10 minutes. The mixture was stirred for 45 minutes at −30° C. The solution was then transferred to an addition flask and added dropwise over the course of 10 minutes to a THF (12 mL) solution of 2-(chlorosulfonyl)-2,2-difluoroethyl methacrylate (Central Glass, 1.19 g, 4.80 mmol, 1.0 eq.) that had been equilibrated beforehand at −30° C. with stirring for 10 minutes. The combined mixture was stirred for 3 hours at −30° C. and then allowed to warm to 10° C. To the final reaction mixture was added 1N HCl (24 mL). The reaction mixture was then extracted with Et$_2$O (72 mL) followed by 1N HCl (24 mL). The lower aqueous layer was also kept and extracted with an additional portion of Et$_2$O (36 mL). The combined organic solution was then extracted twice with brine (24 mL) then dried over anhydrous MgSO$_4$. Solvents were removed by an evaporator and then the crude material was triturated with CHCl$_3$ (100 mL) that precipitated a solid that was removed by filtration. The solution was concentrated to yield a crude product that was concentrated by evaporator. The crude material was purified by column chromatography (hexane/CH$_2$Cl$_2$) to yield the target PAG monomer as a colorless oil (0.23 g, 11.8% yield). $^1$H-NMR (CDCl$_3$), delta (ppm): 1.99 (s, 3H), 4.83 (td, J=12.7, 5.6 Hz, 2H), 5.74 (s, 1H), 6.19 (q, J=6.2 Hz, 1H), 6.28 (s, 1H), 7.58 (t, J=7.8 Hz, 2H), 7.70-7.76 (m, 1H), 7.94-8.02 (m, 1H). $^{19}$F-NMR (CDCl$_3$, standard: C$_6$F$_6$=−162.2 ppm), delta (ppm): −72.00 (d, J=6.2 Hz, 3F), −106.39 (dt, J=246.0, 12.8 Hz, 1F), −107.22 (dt, J=246.0, 12.8 Hz, 1F).

Example 7. Preparation of Monomer M-2

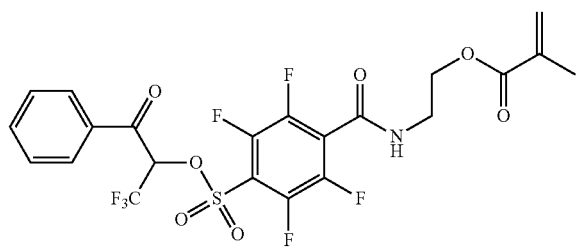

2-(4-(Chlorosulfonyl)-2,3,5,6-tetrafluorobenzamido) ethyl methacrylate (SM-1, 0.751 g, 1.86 mmol) was added to a 20 mL round bottom along with dichloromethane (DCM, 5 mL) and a magnetic stirbar. The round bottom flask was then affixed with an addition funnel where a solution of 2-hydroxy-2-trifluoromethylacetophenone (SM-4, 0.380 g, 1.86 mmol) dissolved in DCM (5 mL) was added. The addition funnel was connected to nitrogen to purge the reaction of air for a period of between 1-3 minutes. Then n-BuLi (1.162 mL, 1.86 mmol, 1.6 M solution in hexane) was added to the addition funnel. The addition funnel was agitated. The round bottom was then immersed in an ice bath and a nitrogen stream was maintained over the reaction mixture. The solution in the addition funnel was then added to the reaction mixture dropwise over the course of 30 minutes. The resulting solution was stirred overnight and allowed to warm to room temperature. The reaction mixture was evaporated to dryness, triturated with hexane, and filtered. The insoluble white powder (0.35 gram) was determined to be the product M-2. $^1$H NMR (400 MHz, Acetone-d$_6$), delta (ppm): 8.56 (t, J=6.0 Hz, 1H), 8.24-8.03 (m, 2H), 7.82 (t, J=7.4 Hz, 1H), 7.65 (t, J=7.8 Hz, 2H), 7.13 (q, J=6.3 Hz, 1H), 6.13 (s, 2H), 5.65 (dq, J=3.5, 1.7 Hz, 2H), 4.35 (q, J=5.4 Hz, 4H), 3.80 (dq, J=10.8, 4.5, 3.4 Hz, 4H), 2.03-1.84 (m, 6H). $^{19}$F NMR (376 MHz, Acetone), delta (ppm): 105.06, 105.05, 41.96, 41.93, 37.21, 37.18.

Example 8. Preparation of Monomer M-3

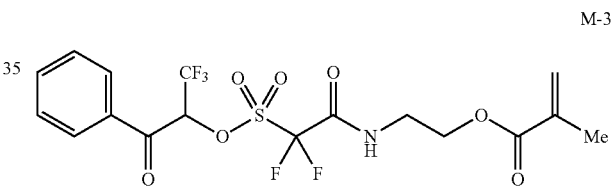

A 50 mL flask was charged with 2-hydroxy-2-trifluoromethylacetophenone (SM-4, 1.36 g, 6.40 mmol, 1.0 eq.) and THF (16 mL) under nitrogen stream. The mixture was stirred for 10 minutes at −30° C. n-BuLi (4.0 mL, 6.40 mmol, 1.0 eq. 1.6 M) was added dropwise to the mixture over the course of 10 minutes and the mixture was stirred for 60 minutes at −30° C. This solution was then transferred to an addition flask and added dropwise over the course of 15 minutes to a stirring solution of THF (16 mL) and 2-(2,2-difluoro-2-(fluorosulfonyl)acetamido)ethyl methacrylate (SM-2, 1.85 g, 6.40 mmol, 1.0 eq.) at −30° C. under a nitrogen stream. This reaction mixture was subsequently stirred for 2.5 hours at −30° C. to 10° C. 1N HCl (32 mL) was added to the final reaction mixture which was then extracted with Et$_2$O (96 mL) followed by 1N HCl (32 mL). The lower aqueous layer was saved and extracted with an additional portion of Et$_2$O (64 mL). The organic layers were then combined and washed with twice with brine (32 mL portions) and the solution dried over MgSO$_4$. Solvents were removed by an evaporator and the crude material purified by column chromatograph (hexane/CH$_2$Cl$_2$) to give the target PAG monomer as colorless oil (0.32 g, 10.6% yield). $^1$H-NMR (CDCl$_3$), delta (ppm): 1.96 (s, 3H), 3.68-3.77 (m, 2H), 4.36 (t, J=5.2 Hz, 2H), 5.60-5.67 (m, 1H), 6.17 (s, 1H), 6.37 (q, J=6.2 Hz, 1H), 7.59 (t, J=7.9 Hz, 2H), 7.75 (t, J=7.5 Hz, 1H), 7.98 (d, J=7.4 Hz, 2H). $^{19}$F-NMR (CDCl$_3$, standard: $C_6F_6=-162.2$ ppm), delta (ppm): -71.88 (d, J=6.2 Hz, 3F), -105.77 (d, J=246.1 Hz, 1F), -107.40 (d, J=246.1 Hz, 1F).

Example 9. Preparation of Monomer M-4

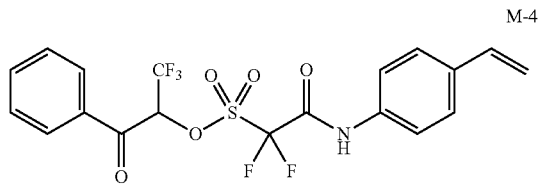 [SMILES: C=Cc1ccc(NC(=O)C(F)(F)S(=O)(=O)OC(C(=O)c2ccccc2)C(F)(F)F)cc1]

M-4

A 50 mL flask was charged with 2-hydroxy-2-trifluoromethylacetophenone (SM-4, 0.98 g, 4.80 mmol, 1.0 eq.) and THF (12 mL) under nitrogen stream and the mixture was stirred for 10 minutes at -30° C. n-BuLi (3.0 mL, 4.80 mmol, 1.0 eq. 1.6 M) was added dropwise to the mixture over 10 minutes and the mixture was stirred for 45 minutes at -30° C. This solution was then transferred to an addition flask and added dropwise over the course of 15 minutes to a stirring solution of THF (12 mL) and 1,1-difluoro-2-oxo-2-(4-vinylphenylamino)-1-ethanesulfonyl fluoride (SM-3, 1.43 g, 4.80 mmol, 1.0 eq.) that was at -30° C. and under a nitrogen stream. The reaction mixture was then stirred for 3 hours at -30° C. and allowed to warm to 10° C. 1N HCl (24 mL) was then added to the reaction mixture, which was then extracted with Et$_2$O (72 mL) followed by 1N HCl (24 mL). After the acid wash, the lower aqueous layer was saved and subsequently extracted with Et$_2$O (36 mL portion) and then combined with other organic layers. The organics were then washed twice with brine (24 mL) and then dried over anhydrous MgSO$_4$. Solvents were removed by an evaporator and the resulting material was triturated with CH$_2$Cl$_2$ (100 mL), precipitating a solid material that was filtered. The filtrate was concentrated and purified by column chromatography (hexane/CH$_2$Cl$_2$) to obtain the target PAG monomer as a white solid (0.60 g, 27.0% yield). $^1$H-NMR (CDCl$_3$), delta (ppm): 5.31 (d, J=10.9 Hz, 1H), 5.78 (d, J=17.6 Hz, 1H), 6.45 (q, J=6.1 Hz, 1H), 6.73 (dd, J=17.6, 10.9 Hz, 1H), 7.46 (d, J=8.6 Hz, 2H), 7.53-7.70 (m, 4H), 7.74-7.83 (m, 1H), 8.03 (d, J=8.3 Hz, 2H), 8.95 (s, 1H). $^{19}$F-NMR (CDCl$_3$, standard: $C_6F_6=-162.2$ ppm), delta (ppm): -71.76 (d, J=6.1 Hz, 3F), -104.93 (d, J=244.5 Hz, 1F), -108.51 (d, J=244.5 Hz, 1F)

Example 10. Preparation of Monomer CM-1 (Comparative)

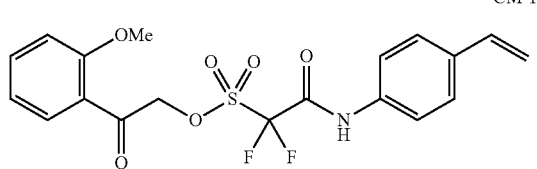

CM-1

A 100 mL flask was charged with 1,1-difluoro-2-oxo-2-(4-vinylphenylamino)ethanesulfonyl fluoride (SM-3, 2.68 g, 9.60 mmol, 1.0 eq.), 2-hydroxy-2'-methoxyacetophenone (SM-5, 1.60 g, 9.60 mmol, 1.0 eq.) and THF (48 mL) under nitrogen stream and the mixture was stirred for 5 minutes at -30° C. n-BuLi (6.0 mL, 9.60 mmol, 1.0 eq. 1.6 M) was added dropwise to the mixture over 10 minutes. The mixture was stirred for 3.5 hours at -30° C. and allowed to warm to 10° C. 1N HCl (48 mL) was added to the reaction mixture that was extracted with AcOEt (144 mL), followed by 1N HCl (48 mL), saturated aqueous NaHCO$_3$ (24 mL) and brine (48 mL). The organic solution was subsequently dried over MgSO$_4$. 2,2'-Methylene-bis(4-methyl-6-tert-butylphenol) (134 mg, 0.5 wt % based on weight of SM-3) was added as inhibitor. The solvents were removed by an evaporator and the resulting crude material was triturated with hexane (150 mL) for 30 minutes at 40° C. The solution was then decanted and this procedure was repeated twice. CH$_2$Cl$_2$ (150 mL) was added, largely dissolving the solid material and precipitating a sodium salt. This mixture was filtered over a bed of celite and the filtrate was concentrated by evaporator. Hexane (150 mL) was added to the crude material and the mixture was stirred for 15 hours at room temperature followed by heating for 2 hours at 40° C. The crude solids where filtered and recrystallized from a mixed solvent system (hexane/CHCl$_3$, 50° C. to 0° C.) to yield the target PAG monomer as white solid (1.21 g, 29.6% yield). $^1$H-NMR (CDCl$_3$), delta (ppm): 4.00 (s, 3H), 5.23 (dd, J=0.6, 10.9 Hz, 1H), 5.70 (s, 2H), 5.72 (dd, J=0.6, 17.6 Hz, 1H), 6.69 (dd, J=10.9, 17.6 Hz, 1H), 7.05 (d, J=8.3 Hz, 1H), 7.13 (ddd, J=0.8, 7.5, 7.6 Hz, 1H), 7.43 (d, J=8.6 Hz, 2H), 7.65 (ddd, J=1.8, 7.8, 7.9 Hz, 1H), 7.78 (d, J=8.6 Hz, 2H), 8.12 (dd, J=1.8, 7.9 Hz, 1H), 10.39 (brs, 1H). $^{19}$F-NMR (CDCl$_3$, standard: $C_6F_6=-162.2$ ppm), delta (ppm): -108.55 (s, 2F).

Synthesis of PAG Polymers

Example 11. Preparation of P-1: poly(M-1-co-ECPMA-co-NBHFAMA), Feed Molar Ratio: 05:40:55

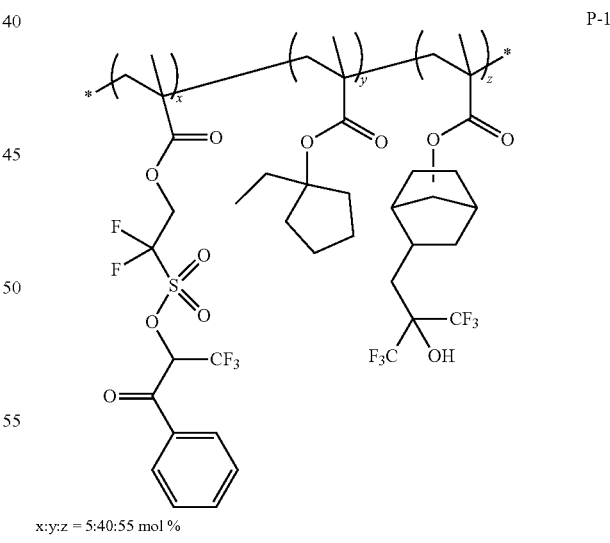

P-1 x:y:z = 5:40:55 mol %

NBHFAMA (1.58 grams, 0.0044 mole), ECPMA (0.583 grams, 0.0032 mole), PAG monomer M-1 (0.166 grams, 0.0004 mole), and tetrahydrofuran (THF, 9.31 grams) were placed in a round bottom flask equipped with a condenser and a nitrogen inlet. To this solution, 2,2'-azobisisobutyronitrile (AIBN, 0.053 gram, 0.00032 mole) and 1-dodecanethiol (0.048 gram, 0.00024 mole) were added and stirred until dissolved. The solution was degassed using four vacuum/nitrogen purges. The solution was then heated at 65° C. in an oil bath for 18 hours. Afterwards, the solution was added drop-wise into hexanes (250 ml). The precipitated polymer was filtered through a medium frit funnel, washed with 100 ml hexanes, and dried under suction. This polymer was then dried in a vacuum oven at 60° C. Yield: 1.13 grams. Average molecular weight: Mw 11551; Mn 8868; polydispersity (PDI): 1.30. According to thermogravimetric analysis (TGA), the polymer starts decomposing (deprotection of the ECPMA) at around 130° C. Tg was not detected below 130° C. by differential scanning calorimetry (DSC). The final composition according to inverse gated $^{13}C$ NMR was x:y:z=7.2:31.0:61.6 mol %.

Example 12. Preparation of P-2: poly(M-2-co-ECPMA-co-NBHFAMA), Feed Molar Ratio: 05:40:55

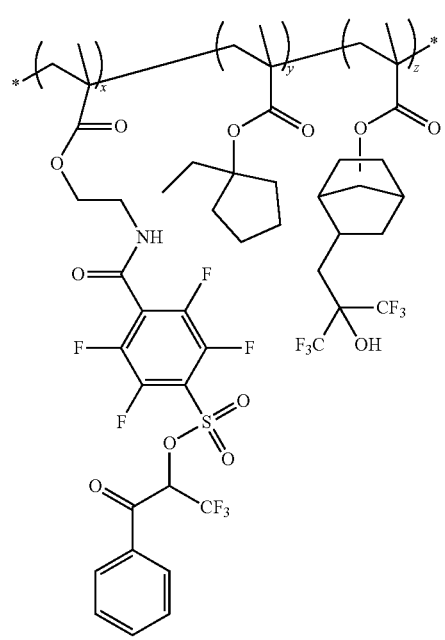

x:y:z = 5:40:55 mol %

NBHFAMA (1.98 grams, 0.0055 mole), ECPMA (0.73 grams, 0.0040 mole), PAG monomer M-2 (0.308 grams, 0.0005 mole), and THF (12.07 grams) were placed in a round bottom flask equipped with a condenser and a nitrogen inlet. To this solution, 2,2'-azobisisobutyronitrile (AIBN, 0.066 gram, 0.0004 mole) and 1-dodecanethiol (0.060 gram, 0.00030 mole) were added and stirred until dissolved. The solution was degassed using four vacuum/nitrogen purges and heated at 65° C. in an oil bath for 18 hours. Afterwards, the solution was added drop-wise into hexanes (2×300 mL). The precipitated polymer was filtered through a medium frit funnel, washed with hexanes (100 mL), and dried under suction. This polymer was then dried in a vacuum oven at 60° C. Yield: 1.75 grams. Average molecular weight: Mw 8432; Mn 6275; polydispersity (PDI): 1.34. According to TGA, the polymer starts decomposing (deprotection of the ECPMA) at around 130° C. A Tg was not detected below 130° C. by DSC. The composition according to inverse gated $^{13}C$ NMR was: x:y:z=5:35:60 mol %.

Example 13. Preparation of PAG Polymer CP-1 (Comparative): poly(CM-1-co-ECPMA-co-NBHFAMA), Feed Molar Ratio: 05:40:55

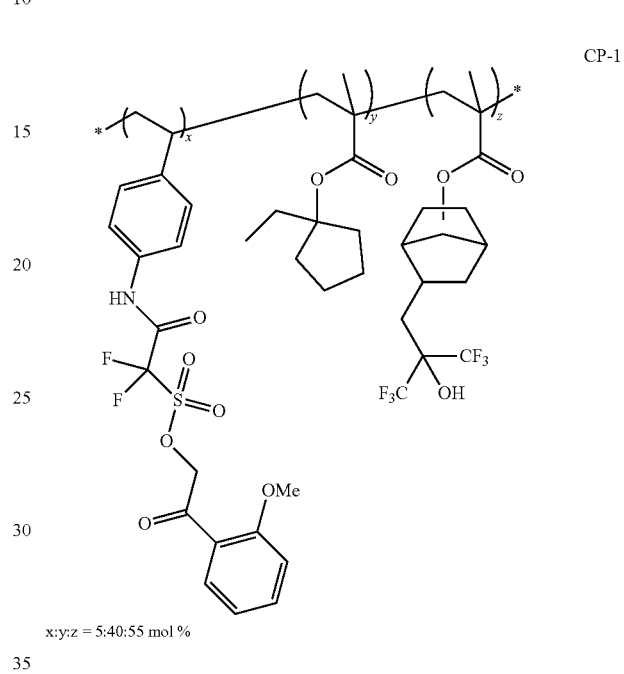

x:y:z = 5:40:55 mol %

NBHFAMA (1.98 grams, 0.0055 mole), ECPMA (0.73 grams, 0.0040 mole), comparative PAG monomer CM-1 (0.213 grams, 0.0005 mole), and THF (11.7 grams) were placed in a round bottom flask equipped with a condenser and a nitrogen inlet. To this solution, 2,2'-azobis(2,4-dimethylvaleronitrile) (Vazo-52, 0.110 gram, 0.0005 mole) and 1-dodecanethiol (0.060 gram, 0.00030 mole) were added, and the mixture was stirred until the solids were dissolved. The resulting solution was degassed using four vacuum/nitrogen purges. The solution was then heated at 60° C. in an oil bath for 18 hours. Afterwards, the solution was added drop-wise into hexanes (400 mL). The precipitated polymer was filtered through a medium frit funnel, washed with 100 ml hexanes, and dried under suction. This polymer was then dried in a vacuum oven at 60° C. Yield: 1.96 grams. Average molecular weight: Mw 5862; Mn 4712; polydispersity (PDI): 1.24.

The polymer did not have the typical deprotection weight loss (loss of the ethyl cyclopentyl ester group) in TGA. This polymer readily dissolved in 0.26 N TMAH solution indicating carboxylic acid has formed as a result of deprotection of ECP group during polymerization. IR spectrum had a strong peak at 1699 cm$^{-1}$ confirming the presence of carboxylic acid functionality.

Polymer PAG Thermal Stability

Table 2 summarizes the thermogravimetric analysis (TGA) data and differential scanning calorimetry (DSC) data for some of the PAG polymers. $T_d$ TGA (° C.) is the main decomposition temperature according to TGA. Mp DSC (° C.) is the melting point. $T_d$ DSC (° C.) is the main decomposition temperature according to DSC.

TABLE 2

| Example | Name | $T_d$ TGA (°C.) | Mp DSC (°C.) | $T_d$ DSC (°C.) |
| --- | --- | --- | --- | --- |
| 11 | P-1 | 140 | Not detected | 130 |
| 12 | P-2 | 140 | Not detected | 125 |
| 13 | CP-1 | Decomposed* | Decomposed* | Decomposed* |

*CP-1 decomposes during synthesis and therefore the resulting polymer has already undergone deprotection.

Resist Formulations

Resist compositions for non-ionic PAG polymers were prepared by forming a 3.5 wt % (weight percent) solution, based on total weight of the solution, of a given PAG polymer in propylene glycol methyl ether acetate (PGMEA). An organic base, 2-phenyl benzimidazole (referred to as quencher), was added to the solution in an amount of 0.33 wt % (referred to as 1× quencher) or 0.66 wt % (referred to as 2× quencher) based on total weight of the PAG polymer. The solution was then filtered through a 0.2 micrometer poly(tetrafluoroethylene) (PTFE) syringe filter. The formulations were not optimized.

Line Patterns

The resist formulation was spin coated to a thickness between 30 to 50 nm onto silicon wafers having a bottom anti-reflective coating (BARC). The BARC underlayer was used for adhesion purposes. The wafer was given a post-apply bake at 110° C. for 60 seconds on a hot plate. The wafer was then exposed on a 0.3-NA extreme ultraviolet (EUV) micro exposure tool (MET) at variable doses. The exposed wafer was given a post-exposure bake at 110° C. for 60 seconds. The film thickness (FT) was nominally 40 nm. Both bakes were done with the wafer in contact with the hot plate. A 60-second development of the resist was carried out using a gentle spray of 0.26 N aqueous tetramethylammonium hydroxide solution (TMAH) to puddle followed by water rinse and spin dry. Top and cross-sectional images were inspected using a LEO Carl Zeiss scanning electron micrograph (SEM) tool. Cross sectional samples were coated with thin PdAu to avoid sample charging.

Results

Figure 3:
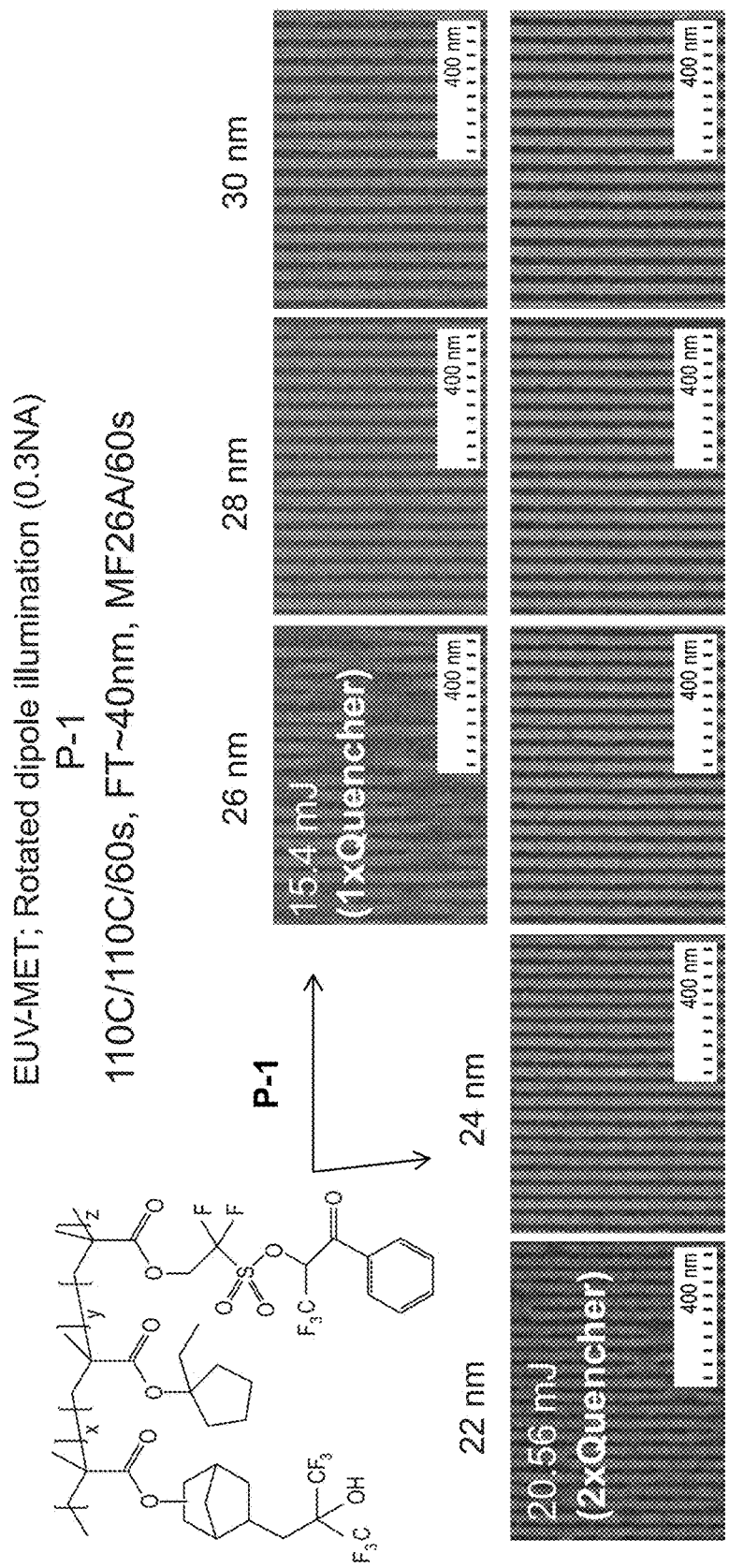
FIG. 3 is a set of SEM images of line patterns of half-pitch 22 nm to 30 nm formed using PAG polymer P-1, 1× quencher or 2× quencher, exposed at an EUV wavelength of 13.5 nm.

FIG. 3 is a set of SEM images of line patterns of half-pitch 22 nm to 30 nm formed using PAG polymer P-1 and 1× quencher or 2× quencher. Clean lines were formed at 28 nm to 30 nm half-pitch using 1× quencher, whereas clean lines were produced at 24 nm to 30 nm half pitch using 2× quencher.

Figure 4:
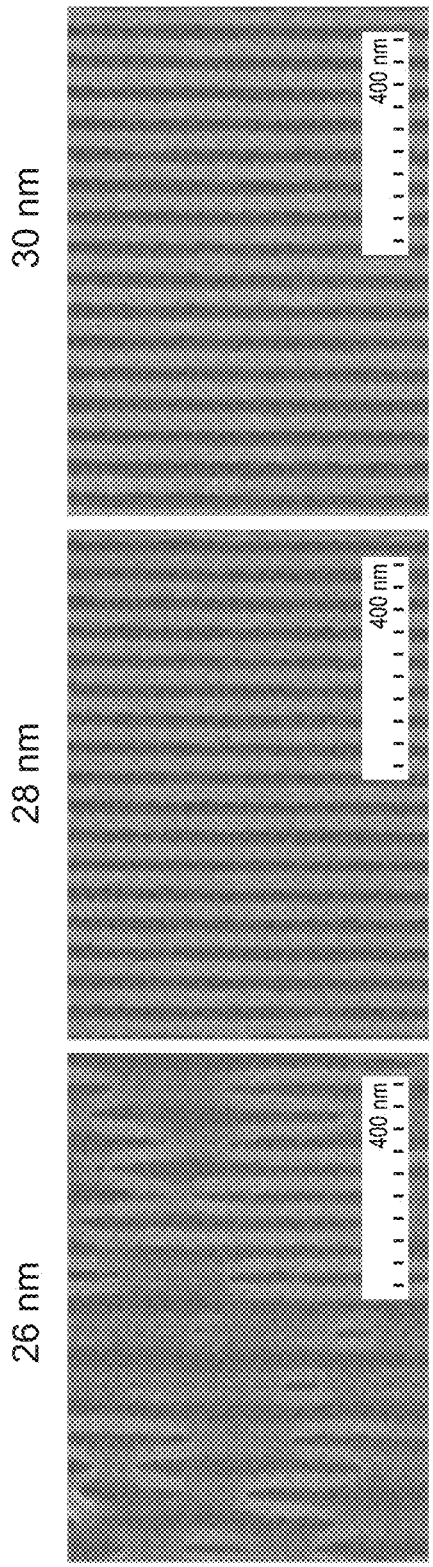
FIG. 4 is a set of SEM images of line patterns of half-pitch 26 nm to 30 nm formed using PAG polymer P-2, 1× quencher, exposed at an EUV wavelength of 13.5 nm.

FIG. 4 is a set of SEM images of line patterns of half-pitch 26 nm to 30 nm formed using PAG polymer P-2 and 1× quencher. Clean lines were formed at 28 nm to 30 nm half pitch.

No SEM results were obtained for comparative polymer CP-1 due to decomposition of CP-1 during synthesis.

The results indicate that PAG polymers comprising sulfonate esters of alpha-hydroxy aryl ketones have commercially useful film-forming and photo-acid generating properties for lithographic applications when the sulfonate ester groups contain the above-described fluorinated $R^1$ and $Z'$ groups.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. When a range is used to express a possible value using two numerical limits X and Y (e.g., a concentration of X ppm to Y ppm), unless otherwise stated the value can be X, Y, or any number between X and Y.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and their practical application, and to enable others of ordinary skill in the art to understand the invention.

What is claimed is:

1. A compound of formula (1):

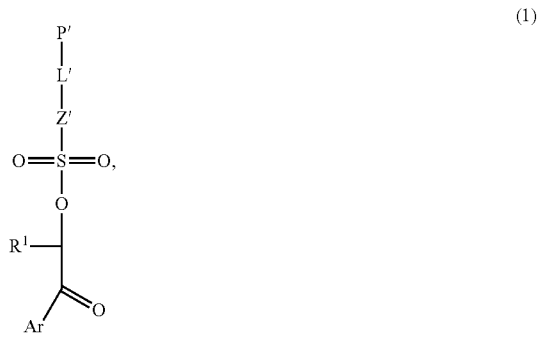

wherein

Ar is a monovalent radical comprising one or more aromatic rings,

L' is a single bond or a divalent $C_0$-$C_{10}$ linking group,

P' is a $C_2$-$C_{20}$ monovalent radical comprising a polymerizable carbon-carbon double bond, $R^1$ is a monovalent perfluorinated $C_1$-$C_{10}$ radical, wherein $R^1$ has a molecular formula consisting of elements carbon and fluorine, and Z' is a divalent $C_1$-$C_{10}$ radical having a molecular formula consisting of elements carbon, fluorine, and optionally hydrogen.

2. The compound of claim 1, wherein P' is

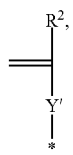

wherein $R^2$ is a monovalent radical selected from the group consisting of hydrogen, methyl, and trifluoromethyl, Y' is a divalent radical selected from the group consisting of

and aromatic groups comprising one or more aromatic rings, and

Y' is linked to L'.

3. The compound of claim 2, wherein Y' is

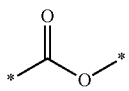 [SMILES: *OC(*)=O]

and the compound is a methacrylate ester.

4. The compound of claim 2, wherein Y' is benzene-1,4-diyl:

5. The compound of claim 1, wherein P' is selected from the group consisting of

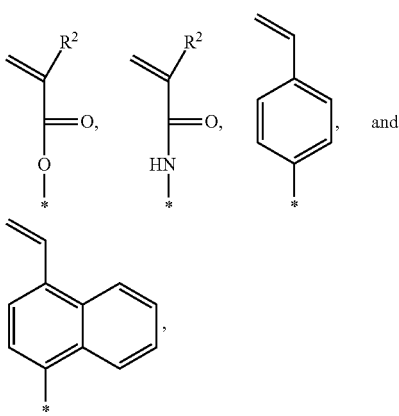

wherein $R^2$ is selected from the group consisting of hydrogen, methyl, and trifluoromethyl.

6. The compound of claim 1, wherein P' is

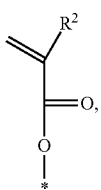

wherein $R^2$ is selected from the group consisting of hydrogen, methyl, and trifluoromethyl.

7. The compound of claim 1, wherein P' is

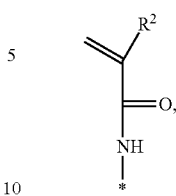

wherein $R^2$ is selected from the group consisting of hydrogen, methyl, and trifluoromethyl.

8. The compound of claim 1, wherein P' is

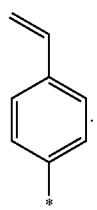 [SMILES: *c1ccc(C=C)cc1]

9. The compound of claim 1, wherein Z' is selected from the group consisting of

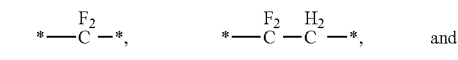

(difluoromethylene)   (1, 1-difluoroethane-1,2-diyl)   and

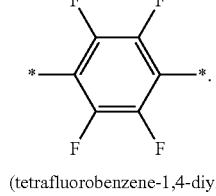

(tetrafluorobenzene-1,4-diyl)

10. The compound of claim 1, wherein $R^1$ is selected from the group consisting of trifluoromethyl and perfluoroethyl.

11. The compound of claim 1, wherein Ar is selected from the group consisting of

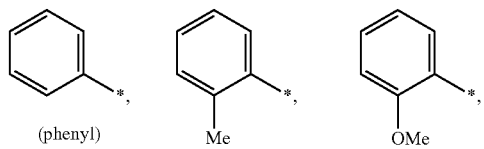

(phenyl)      Me           OMe
         (2-methylphenyl)  (2-methoxyphenyl)

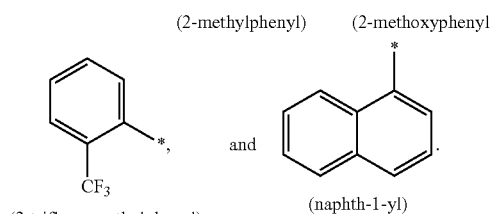

(2-trifluoromethylphenyl)      (naphth-1-yl)

12. The compound of claim 9, wherein the compound is selected from the group consisting of

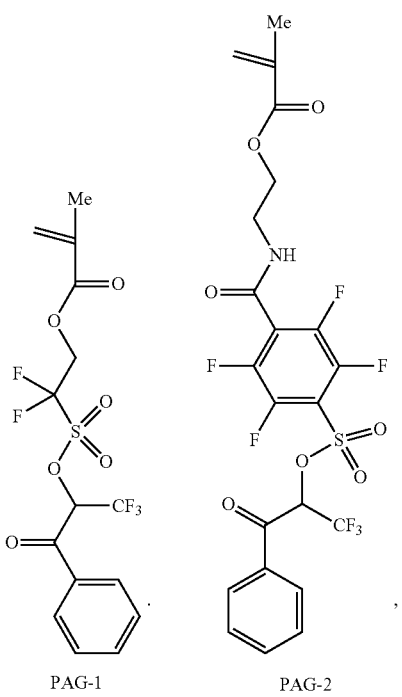

PAG-1, PAG-2

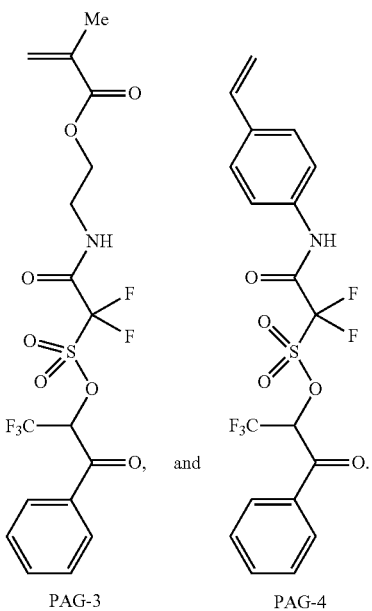

PAG-3, PAG-4

13. A photo-acid generating polymer (PAG polymer), comprising a non-ionic PAG repeating unit of formula (8):

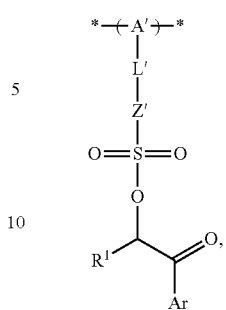

(8)

wherein
the PAG polymer has a polymer backbone,
A' is a trivalent radical comprising a pair of covalently linked carbons which are carbons of the polymer backbone,
Ar is a monovalent aryl radical comprising one or more aromatic rings,
L' is a single bond or a divalent $C_0$-$C_{10}$ linking group,
$R^1$ is a monovalent perfluorinated $C_1$-$C_{10}$ radical, wherein $R^1$ has a molecular formula consisting of elements carbon and fluorine, and
Z' is a divalent $C_1$-$C_{10}$ radical consisting of elements carbon, fluorine, and optionally hydrogen.

14. The PAG polymer of claim 13, wherein A' is

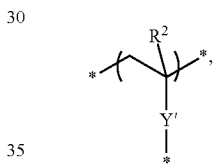

wherein
$R^2$ is a monovalent radical selected from the group consisting of hydrogen, methyl, and trifluoromethyl,
Y' is a divalent radical selected from the group consisting of

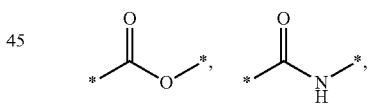

and aromatic groups comprising one or more aromatic rings, and
Y' is linked to L'.

15. The PAG polymer of claim 14, wherein Y' is

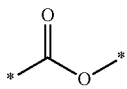

wherein the oxygen is linked to L'.

16. The PAG polymer of claim 14, wherein Y' is benzene-1,4-diyl.

17. The PAG polymer of claim 14, wherein the PAG polymer is thermally stable in a lithographic process up to at least 130° C.

18. The PAG polymer of claim 14, wherein the PAG repeating unit is selected from the group consisting of:

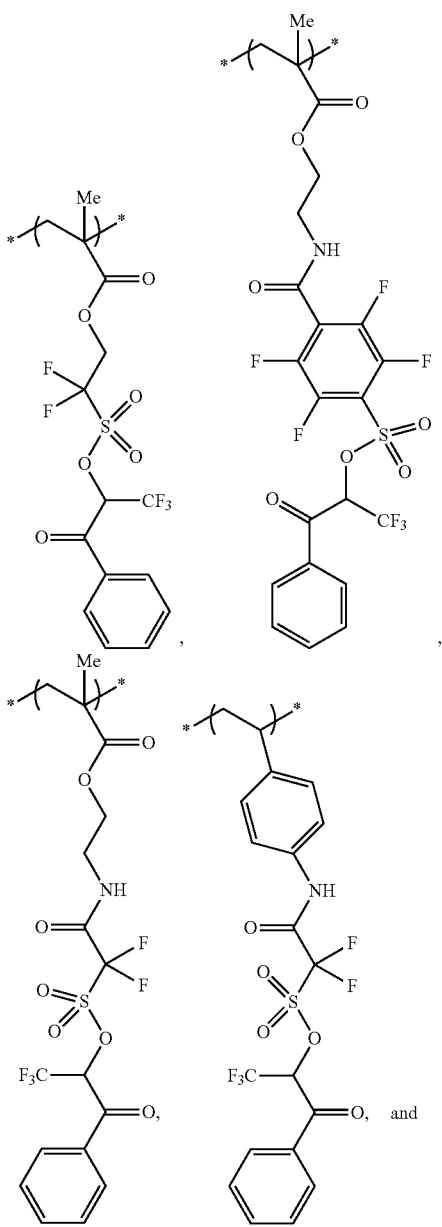

and combinations thereof.

19. The PAG polymer of claim 14, wherein the PAG polymer comprises a second repeating unit comprising an acid labile group, the acid labile group comprising a protected carboxylic acid group capable of being deprotected by an acid, and the PAG polymer is capable of chemical amplification in a lithographic process.

20. The PAG polymer of claim 19, wherein the acid labile group of the protected carboxylic acid group is protected with an acid-labile functionality selected from the group consisting of tertiary esters, acetals, ketals, carbonates, and orthoesters.

21. A resist composition, comprising:
the PAG polymer of claim 13; and
an organic solvent, wherein the PAG polymer is dissolved in the organic solvent, and the resist composition is suitable for forming a resist pattern in a lithographic process.

22. A method, comprising:
providing a layered structure comprising a resist layer disposed on a surface of a substrate, the resist layer comprising the PAG polymer of claim 13;
pattern-wise exposing the resist layer to radiation, thereby forming an exposed resist layer;
baking the exposed resist layer at about 90° C. to about 130° C. for at least 1 second, thereby forming a treated resist layer; and
selectively removing a region of the treated resist layer using a developer, thereby forming a patterned resist layer.

23. The method of claim 22, wherein the developer is an aqueous alkaline developer that selectively removes an exposed region of the treated resist layer, leaving a positive tone patterned resist layer.

24. The method of claim 22, wherein the developer is an organic solvent developer that selectively removes a non-exposed region of the treated resist layer, leaving a negative tone patterned resist layer.

25. The method of claim 22, wherein the radiation has a wavelength less than 300 nm.

* * * * *